US006329497B1

(12) United States Patent
Boger

(10) Patent No.: US 6,329,497 B1
(45) Date of Patent: Dec. 11, 2001

(54) SANDRAMYCIN ANALOGS

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/381,883

(22) PCT Filed: Mar. 27, 1998

(86) PCT No.: PCT/US98/06058

§ 371 Date: Dec. 3, 1999

§ 102(e) Date: Dec. 3, 1999

(87) PCT Pub. No.: WO98/43663

PCT Pub. Date: Oct. 8, 1998

Related U.S. Application Data

(60) Provisional application No. 60/042,241, filed on Mar. 28, 1997, and provisional application No. 60/042,242, filed on Mar. 28, 1997.

(51) Int. Cl.[7] .............................. A61K 38/14; A61K 38/16

(52) U.S. Cl. ........................ 530/322; 514/8; 536/24.31; 435/6

(58) Field of Search ........................ 530/322; 514/8; 536/24.31; 435/6

(56) References Cited

U.S. PATENT DOCUMENTS 4,582,639 * 4/1986 Matson et al. .

OTHER PUBLICATIONS

Denny, et al., "Potential Antitumor Agents. 44. Synthesis and Antitumor Activity of New Classes of Diacridines: Importance of Linker Chain Rigidity for DNA Binding Kinetics and Biological Activity", *J. Med. Chem.* 28: 1568–1574 (1985).

Rance, et al., "UK–63,052 Complex, New Quinomycin Antibiotics from *Streptomyces Braegensis* Subsp. Japonicus; Taxonomy, Fermentation, Isolation, Characterisation and Antimicrobial Activity", *J. Antibiotics* 42: 206–217 (1989).

Matson, et al., "Sandramycin, A Novel Antitumor Antibiotic Produced by a *Nocardiodes* Sp. Product Isolation, Characterization and Biological Properties", *J. Antibiotics* 42: 1763–1767 (1989).

Fox, "Footprinting Studies of the Interaction of Quinomycin Antibiotic UK63052 with DNA: Comparison with Echinomycin", *J. Antibiot.* 43: 1307–1315 (1990).

Matson, et al., "Sandramycin, a Novel Antitumor Antibiotic Produced by A *Nocardiodes* sp. II. Structure Determination", *J. Antibiot.* 46: 162–166 (1993).

Boger, et al., "(–)-Sandramycin: Total Synthesis and Preliminary DNA Binding Properties", *J. Am. Chem. Soc.* 115: 11624–11625 (1993).

(List continued on next page.)

*Primary Examiner*—Ralph Gitomer
*Assistant Examiner*—Devesh Khare
(74) *Attorney, Agent, or Firm*—Donald G. Lewis

(57) ABSTRACT

Analogs of sandramycin (1) are synthesized and shown to have cytoxicity against various tumor cell types. The relative cytotoxic properties of the sandramycin analogs are approximately parallel tp their relative DNA binding affinities. An exception to this generalization is compound (4) which completely the sandramycin chromophore phenol. Although typically 4–10× less potent than sandramycin against leukemia cell lines, compound (4) proved to be 1–10,000× more potent against melanomas, carcinomas, and adenocarcinomas exhibiting $IC_{50}$ values of 1 pM–10 nM. This activity places compound (4) amongst the most potent agents identified to date.

33 Claims, 26 Drawing Sheets

OTHER PUBLICATIONS

Boger, et al., "A Modified Friedlander Condensation for the Synthesis of 3–Hydroxyquinoline–2–carboxylates", *J. Org. Chem. 60*: 7369–7371 (1995).

Boger, et al., "(–)–Sandramycin: Total Synthesis and Characterization of DNA Binding Properties", *J. Am. Chem. Soc. 118*: 1629–1644 (1996).

Lingham, et al., "Quinoxapeptins: Novel Chromodepsipeptide Inhibitors of HIV–1 and HIV–2 Reverse Transcriptase I. The Producing Organism and Biological Activity", *J. Antibiot. 49*: 253–259 (1996).

Boger, et al., "An Exceptionally Potent Analog of Sandramycin", *Bioorg. Med. Chem. Lett. 7*: 919–922 (1997).

* cited by examiner

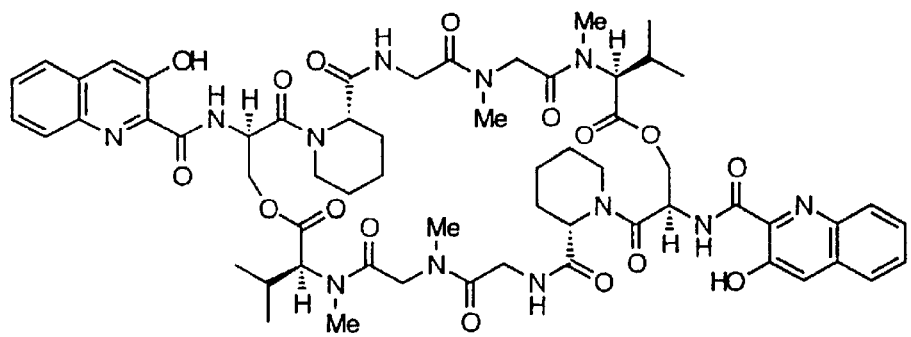
1, sandramycin
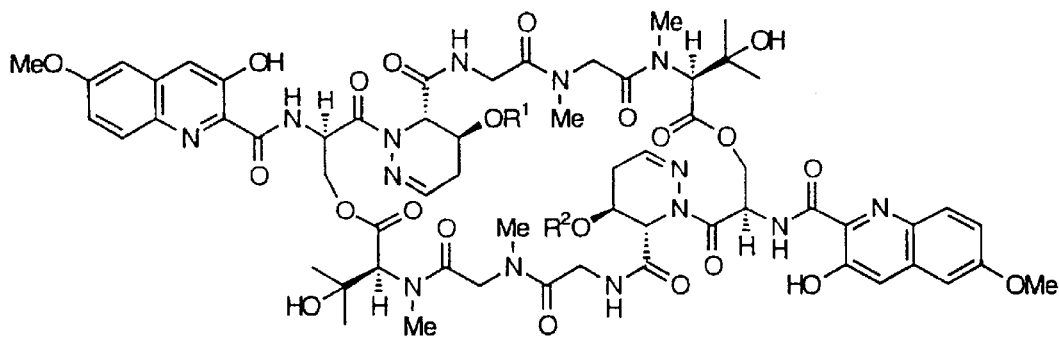
luzopeptin A  R¹ = R² = COCH₃
luzopeptin B  R¹ = H, R² = COCH₃
luzopeptin C  R¹ = R² = H
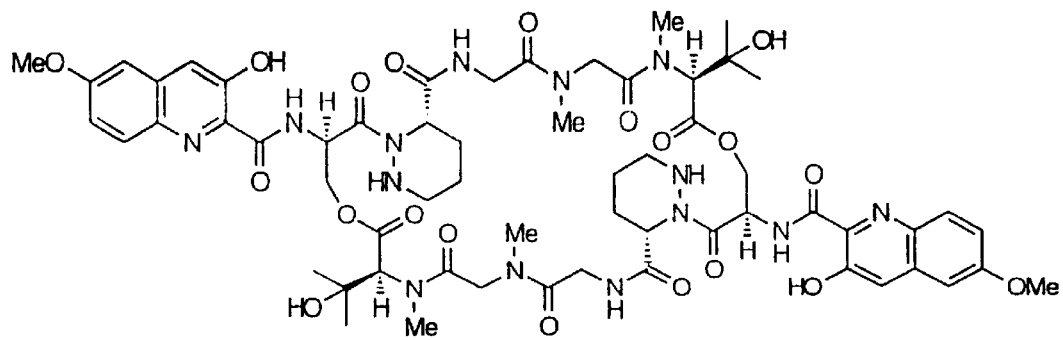
luzopeptin E₂
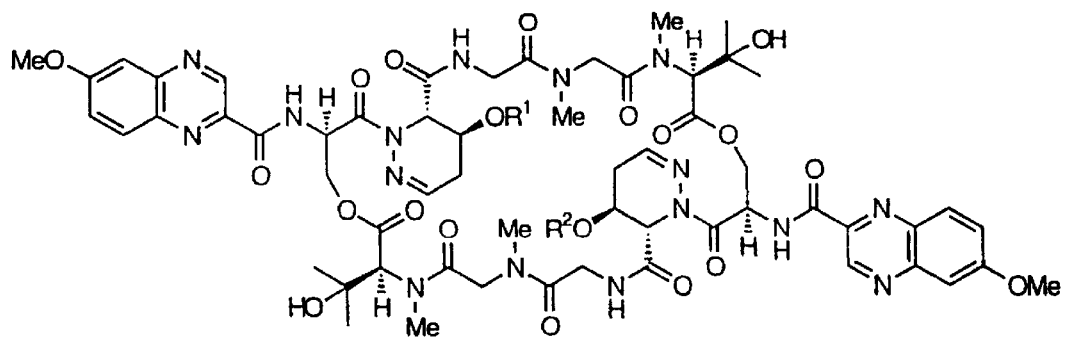
quinoxapeptin A  R¹ = R² = ∞-◁
quinoxapeptin B  R¹ = COCH₃, R² = ∞-◁
FIG. 1

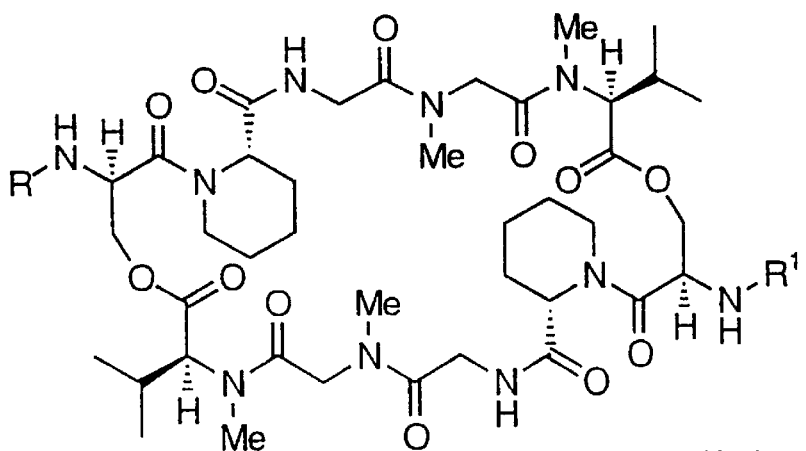
1, R = R¹ = 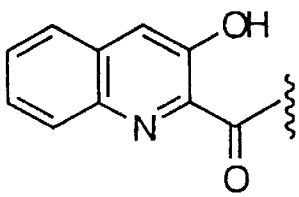
23, R = R¹ = BOC
24, R = SES, R¹ = 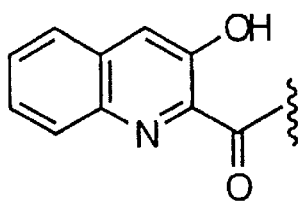
calf thymus DNA
$K_a = 3.4 \times 10^7$ M$^{-1}$
$DG° = -10.2$ kcal/mol
$K_a = 2.4 \times 10^4$ M$^{-1}$
$DG° = -6.0$ kcal/mol
$K_a = 5.7 \times 10^6$ M$^{-1}$
$DG° = -9.2$ kcal/mol
FIG. 3

| analog | excitation (nm) | emission (nm) | % quenching[a] |
|---|---|---|---|
| 1 | 364 | 532 | 76<br>89[b]<br>80[c]<br>91[d] |
| 3 | 339 | 418 | 89 |
| 4 | 286 | 410 | 79 |
| 8 | 311 | 411 | 60 |
| 11 | 341 | 532 | 75 |
| 13 | 335 | 422 | 81 |
| 14 | 358 | 534 | 69 |
| 16 | 368 | 536 | 83 |
| 17 | 345 | 412 | 52 |
| 21 | 324 | 420 | 92 |
| 22 | 325 | 420 | 84 |
| 24 | 360 | 511 | 60 |

FIG. 6

[a] With 5'-d(GCATGC)$_2$- [b] 5'-d(GCGCGC)$_2$- [c] 5'-d(GCTAGC)$_2$- [d] 5'-d(GCGCGC)$_2$-

| Analog | Calf Thymus DNA | | 5'-d(GCATGC)$_2$ | | | |
|---|---|---|---|---|---|---|
| | $K_b$ (M$^{-1}$)$^a$ | $\Delta G°$ (kcal/mol) | $K_b$ (M$^{-1}$)$^a$ | $\Delta G°$ (kcal/mol) | $K_b$ (M$^{-1}$)$^b$ | $\Delta G°$ (kcal/mol) |
| 1 | 1.6 × 10$^7$ | −9.8 | 6.4 × 10$^7$ | −10.6 | 2.3 × 10$^8$ | −11.4 |
| 2 | nd | | | | | |
| 3 | 3.7 × 10$^6$ | −9.0 | 1.3 × 10$^7$ | −9.7 | 1.7 × 10$^7$ | −9.9 |
| 4 | 3.2 × 10$^6$ | −8.9 | 1.4 × 10$^7$ | −9.7 | 2.5 × 10$^7$ | −10.1 |
| 5 | ns$^c$ | | | | | |
| 6 | ns$^c$ | | | | | |
| 7 | ns$^c$ | | | | | |
| 8 | 8.3 × 10$^5$ | −8.1 | 1.3 × 10$^6$ | −8.3 | 3.0 × 10$^6$ | −8.8 |
| 9 | nd$^d$ | | | | | |
| 10 | nd$^d$ | | | | | |
| 11 | 8.3 × 10$^6$ | −9.4$^e$ | 2.6 × 10$^7$ | −10.1 | 5.1 × 10$^7$ | −10.5 |
| 12 | nd | | | | | |
| 13 | 4.8 × 10$^6$ | −9.3$^f$ | 6.4 × 10$^6$ | −9.3 | 1.6 × 10$^7$ | −9.8 |
| 14 | 5.8 × 10$^6$ | −9.2$^e$ | 2.5 × 10$^7$ | −10.1 | 2.9 × 10$^7$ | −10.2 |
| 15 | nd | | | | | |
| 16 | 7.6 × 10$^6$ | −9.4 | 3.6 × 10$^7$ | −10.3 | 7.3 × 10$^7$ | −10.7 |
| 17 | 1.3 × 10$^5$ | −7.0 | 3.5 × 10$^5$ | −7.6 | nd | |
| 18 | ns$^c$ | | | | | |
| 19 | ns$^c$ | | | | | |
| 20 | ns$^c$ | | | | | |
| 21 | na$^g$ | | 3.5 × 10$^6$ | −8.9 | 4.3 × 10$^5$ | −7.7$^e$ |
| 22 | 3.2 × 10$^6$ | −8.9$^e$ | 3.4 × 10$^6$ | −8.9 | 8.0 × 10$^6$ | −9.4 |
| 23 | 2.4 × 10$^4$ | −6.0$^6$ | | | | |
| 24 | 5.7 × 10$^6$ | −9.2$^6$ | | | | |

$^a$Linear fit of high affinity sites. $^b$Non-linear fit of all sites. $^c$Not soluble. $^d$No fluorescence. $^e$Background fluorescence decrease subtracted out, see text. $^f$Data less reliable. $^g$Data not reproducible.

FIG. 8

| deoxyoligonucleotide | $K_b$ (M$^{-1}$)[a] | $\Delta G°$ (kcal/mol) |
|---|---|---|
| d(GC<u>A</u><u>T</u>GC)$_2$ | 23.0 × 10$^7$ | −11.4 |
| d(GC<u>G</u><u>C</u>GC)$_2$ | 14.5 × 10$^7$ | −11.1 |
| d(GC<u>C</u><u>G</u>GC)$_2$ | 8.5 × 10$^7$ | −10.8 |
| d(GC<u>T</u><u>A</u>GC)$_2$ | 8.0 × 10$^7$ | −10.8 |
| d(C<u>G</u><u>T</u>ACG)$_2$ | 1.6 × 10$^7$ | −9.8 |

[a]Calculated by non-linear fit of all sites

FIG. 9

| XX | $k_a$ (M⁻¹s⁻¹)[a] | $k_d$ (s⁻¹)[b] | $K_b$ (M⁻¹)[c] | $\Delta G°$ (kcal/mol) | $K_b$ (M⁻¹)[d] | $\Delta G°$ (kcal/mol) | n[e] |
|---|---|---|---|---|---|---|---|
| AT | 7400 | $6.2 \times 10^{-5}$ | $1.2 \times 10^8$ | −11.0 | $7.8 \times 10^7$ | −10.8 | 1.2 |
| GC | 4300 | $1.1 \times 10^{-4}$ | $3.9 \times 10^7$ | −10.3 | $4.0 \times 10^7$ | −10.4 | 1.2 |
| CG | 2200 | $1.6 \times 10^{-4}$ | $1.4 \times 10^7$ | −9.7 | $1.5 \times 10^7$ | −9.8 | 1.0 |
| TA | 1600 | $1.7 \times 10^{-4}$ | $9.4 \times 10^6$ | −9.5 | $1.8 \times 10^7$ | −9.9 | 1.0 |

[a]Association rate constant. [b]Dissociation rate constant. [c]Binding constant calculated as $k_a/k_d$. [d]Steady state binding constant calculated as $R_A/c = K_b R_{max} - K_b R_A$.[28] [e]Stoichiometry of binding.

FIG. 11

| Analog | $k_a^a$ (M$^{-1}$s$^{-1}$) | $k_d^b$ (s$^{-1}$) | $K_b^c$ (M$^{-1}$) | $\Delta G°$ (kcal/mol) | $K_b^d$ (M$^{-1}$) | $\Delta G°$ (kcal/mol) |
|---|---|---|---|---|---|---|
| 1 | 7400 | $6.2 \times 10^{-5}$ | $1.2 \times 10^8$ | −11.0 | $7.8 \times 10^7$ | −10.8 |
| 2 | 170 | $1.6 \times 10^{-4}$ | $1.1 \times 10^6$ | −8.2 | $5.7 \times 10^6$ | −9.2 |
| 3 | 3000 | $6.6 \times 10^{-5}$ | $4.6 \times 10^7$ | −10.4 | $3.9 \times 10^6$ | −9.0 |
| 4 | 7300 | $1.0 \times 10^{-4}$ | $7.3 \times 10^7$ | −10.7 | $2.4 \times 10^7$ | −10.1 |
| 8 | 280 | $9.4 \times 10^{-5}$ | $3.0 \times 10^6$ | −8.8 | $6.4 \times 10^6$ | −9.3 |
| 10 | 95 | $1.2 \times 10^{-4}$ | $8.3 \times 10^5$ | −8.1 | $2.0 \times 10^4$ | −5.9 |
| 11 | 2600 | $5.7 \times 10^{-5}$ | $4.5 \times 10^7$ | −10.4 | $3.8 \times 10^7$ | −10.3 |
| 13 | 2100 | $2.4 \times 10^{-5}$ | $8.8 \times 10^7$ | −10.8 | $1.1 \times 10^7$ | −9.6 |
| 14 | 630 | $5.1 \times 10^{-5}$ | $1.2 \times 10^7$ | −9.7 | $5.6 \times 10^7$ | −10.6 |
| 16 | 6300 | $3.2 \times 10^{-5}$ | $2.0 \times 10^8$ | −11.3 | $5.6 \times 10^7$ | −10.6 |
| 17 | 230 | $1.5 \times 10^{-3}$ | $1.5 \times 10^5$ | −7.1 | $2.0 \times 10^5$ | −7.2 |
| 21 | 11000 | $1.7 \times 10^{-3}$ | $6.5 \times 10^6$ | −9.3 | $2.1 \times 10^6$ | −8.6 |
| 22 | 820 | $1.2 \times 10^{-4}$ | $6.8 \times 10^6$ | −9.3 | $6.5 \times 10^6$ | −9.3 |
| 23 | | | | | $2.0 \times 10^4$ | −5.9 |
| 24 | | $>5 \times 10^{-4}$ | | | | |

[a] Rate constants determined from plots of $k_s$ versus analog concentration (c) according to the following equation: $k_s = k_a c + k_d$. [b] Dissociation rate constants determined from dissociation of bound analogs in buffer flow according to the following equation: $\ln(R_{Ai}/R_n) = k_d (t_n - t_i)$. [c] Binding constants $K_b$ calculated as $k_a/k_d$. [d] Binding constants determined from steady state binding according to the following equation: $R_A/c = K_b R_{max} - K_b R_A$.[28]

FIG. 12

| Agent | IC$_{50}$, nM | | | | |
|---|---|---|---|---|---|
| | L1210 | Molt-4 | 786-O | Ovcar-3 | B-16 |
| luzopeptin A | 0.02 | 0.08 | 0.2 | 6 | 0.07 |
| sandramycin (1) | 0.02 | 0.08 | 4 | 2 | 0.4 |
| 2 | 20-2 | 4 | 120 | 60 | 8 |
| 24 | 500 | 400 | nt | nt | nt |
| 23 | >10$^5$ | >10$^5$ | 80000 | 80000 | nt |

[a]L1210 (mouse leukemia), Molt-4 (human T-cell leukemia), 786-O (human perirenal cell carcinoma), Ovcar-3 (human ovarian carcinoma), B-16 (melanoma).

FIG. 14

| | |
|---|---|
| 1 (sandramycin) | 0.02 |
| 2 | 20 |
| 3 | 20 |
| 4 | 0.2 |
| 5 | 200 |
| 6 | >10$^5$ |
| 7 | 400 |
| 8 | 80 |
| 9 | 80000 |
| 10 | 80000 |
| 11 | 0.04 |
| 12 | 15 |
| 13 | 0.4 |
| 14 | 0.02 |
| 15 | nt |
| 16 | 0.01 |
| 17 | nt |
| 18 | 3 |
| 19 | 1000 |
| 20 | 7000 |
| 21 | 20 |
| 22 | 20 |

FIG. 15

| Cell line (tumor type) | luzopeptin A | sandramycin | 4 |
| --- | --- | --- | --- |
| L1210 (mouse leukemia) | 0.02 | 0.02 | 0.2 |
| Molt-4 (human T-cell leukemia) | 0.7 | 0.7 | 3 |
| HL-60 (human promyelomic leukemia) | 0.2 | 80 | 0.001 |
| luzopeptin A = sandramycin > 4 | | | |
| B16 (melanoma) | 0.06 | 0.4 | 0.06 |
| SK-MEL28 (human melanoma) | 0.0005 | 1 | 0.001 |
| M24-MET (human metastatic melanoma) | 0.02 | 0.4 | 0.04 |
| 4 = luzopeptin A > sandramycin | | | |
| BT-549 (human breast carcinoma) | 0.5 | 1 | 0.01 |
| MCF-7 (human breast carcinoma) | 20 | 300 | 0.04 |
| OVCAR-3 (human ovarian carcinoma) | 6 | 4 | 1 |
| PC-3 (human prostrate carcinoma) | 0.09 | 0.2 | 0.001 |
| SIHA (human squamous cervix carcinoma) | 0.005 | 0.3 | 0.001 |
| 786-0 (human perirenal cell carcinoma) | 0.02 | 8 | 0.01 |
| 4 > luzopeptin A > sandramycin | | | |
| H322 (human lung adenocarcinoma) | 10 | 20 | 10 |
| UCLA-P3 (human lung adenocarcinoma) | 2 | 10 | 0.002 |
| HT-29 (human colon adenocarcinoma) | 0.5 | 1 | 0.01 |
| 4 > luzopeptin A > sandramycin | | | |
| U251 (human CNS cancer) | 0.9 | 6 | 0.001 |

FIG. 17

| Agent Name/Type | off rate (s⁻¹) (mono-intercalators) | off rate (s⁻¹) (bis-intercalators) | Reference |
|---|---|---|---|
| ethidium bromide | 0.5-30 | | 1 |
| anthracene-9,10-diones | 0.6-150 | | 2 |
| mitoxanthrene | 0.8-40 | | 3 |
| ametantrone | 2.7-17 | | 3 |
| daunorubicin | 1.0-2.2 | | 3,4 |
| doxorubicin | 2.1 | | 4 |
| amsacrine | 167 | | 5 |
| actinomycin D | $2.8 \times 10^{-4} - 0.001$ | | 6 |
| bis-duanomycin | 0.005 | | 6 |
| echinomycin | | 0.003-0.01 | 7,8 |
| quinomycin | | 0.0015-0.04 | 8 |
| triostin A | | 0.03-0.2 | 8 |
| triostin C | | 0.01-0.04 | 8 |
| luzopeptin A | | $(10^{-5})$ | 9 |
| acridines | 56 | 0.02-0.002 | 10 |
| acridines | 41 | $0.067-4 \times 10^{-5}$ | 11 |
| fluorinated acridines | 28-71 | $0.0026 - 9.2 \times 10^{-5}$ | 12 |
| quinolines | 46 | 111-333 | 13 |

FIG. 19

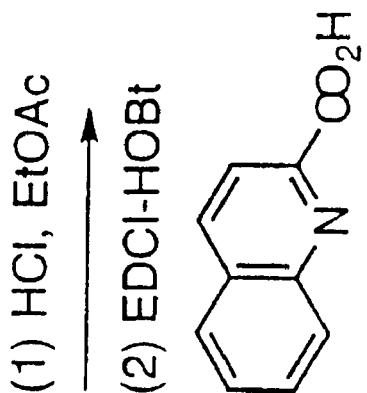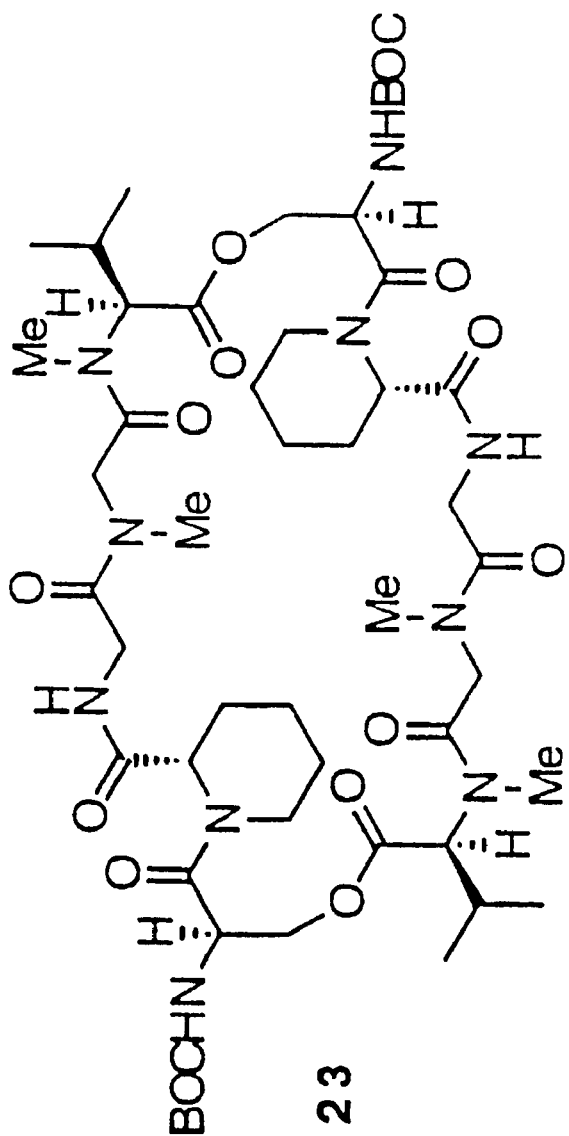
FIG. 20

| cell line | sandramycin | 4 |
|---|---|---|
| L1210 (mouse leukemia) | 0.02 | 0.2 |
| Molt-4 (human T-cell leukemia) | 0.7 | 3 |
| HL-60 (human promyelomic leukemia) | 80 | 0.001 |
| B16 (mouse melanoma) | 0.4 | 0.06 |
| SK-MEL28 (human melanoma) | 1 | 0.001 |
| M24-MET (human metastatic melanoma) | 0.4 | 0.04 |
| BT-549 (human breast carcinoma) | 1 | 0.01 |
| MCF-7 (human breast carcinoma) | 300 | 0.04 |
| OVCAR-3 (human ovarian carcinoma) | 4 | 1 |
| PC-3 (human prostate carcinoma) | 0.2 | 0.001 |
| SIHA (human cervix carcinoma) | 0.3 | 0.001 |
| 786-O (human perirenal carcinoma) | 8 | 0.01 |
| H322 (human lung adenocarcinoma) | 20 | 10 |
| UCLA-P3 (human lung adenocarcinoma) | 10 | 0.002 |
| HT-29 (human colon adenocarcinoma) | 1 | 0.01 |

FIG. 21

SANDRAMYCIN ANALOGS

This application is a 371 of PCT/US98/06058 filed Mar. 27, 1998 which claims priority of Prov. Nos. 60/042,241 and 60/042,242 both filed Mar. 28, 1997.

FIELD OF THE INVENTION

The invention relates to analogs of sandramycin, to the synthesis of analogs of sandramycin, and to their use as anti-cancer and anti-HIV agents. More particularly, the invention relates to analogs of sandramycin having deep-seated structural changes in the chromophore including the deletion of key functional groups or core structural elements, to the synthesis of these compounds the penultimate introduction of substitution chromophores on a key intermediate, and to the use of these compounds against various leukemia, melanoma, carinoma, and adenocarcinomas. Furthermore, some of the analogs possess the ability to inhibit HIV-1 reverse transcriptase.

BACKGROUND

Sandramycin (1) is a natural product having potent antitumor antibiotic activity. Sandramycin has been structurally characterized through spectroscopic and chemical degradation studies. Sandramycin constitutes one of the newest members of a growing class of cyclic decadepsipeptides including luzopeptins A–C and $E_2$, quinaldopeptin and guinoxapeptins A and B which possess potent antitumor, antiviral, and antimicrobial activity (FIG. 1; Matson, et al. *J. Antibiot.* 1989, 42, 1763; Matson et al. *J. Antibiot.* 1993, 46, 162; Ohkuma et al. *J. Antibiot.* 1980, 33, 1087; Tomita et al. *J. Antibiot.* 1980, 33, 1098; *J. Antibiot.* 1981, 34, 148; Konishi et al. *J. Am. Chem. Soc.* 1981, 103, 1241; Arnold et al. *J. Am. Chem. Soc.* 1981, 103, 1243; Toda et al. *J. Antibiot.* 1990, 43, 796). Characteristic of this class of agents, sandramycin possesses a two-fold axis of symmetry and two heteroaromatic chromophores that results in sequence-selective DNA bis-intercalation spanning two base-pairs preferentially at 5'-AT sites. In this respect, the agents are functionally related to the quinoxaline antitumor antibiotics including echinomycin and triostin A which also bind to DNA by bis-intercalation but with a substantially different sequence selectivity (5'-CG versus 5'-AT).

The cytotoxic activity of luzopeptin A and sandramycin has been shown to be 100–300 times greater than echinomycin and smoothly declines in the series with luzopeptin A>B>C. A reverse order of antiviral activity was observed with luzopeptin C>B>A in inhibiting human immunodeficiency virus (HIV) replication in vitro. Notably, this is observed at noncytotoxic concentration for luzopeptin C through inhibition of HIV reverse transcriptase (Take et al. *J. Antibiot.* 1989, 42, 107; Inouye et al. *J. Antibiot.* 1987, 40, 100). The recent disclosure of the quinoxapeptins as potent inhibitors of HIV-1 and HIV-2 reverse transcriptase that are equally active against two resistant single mutants and a double mutant of HIV-1 reverse transcriptase has increased the interest in this class of agents especially since they were found not to inhibit human DNA polymerase $\alpha$, $\beta$, $\gamma$, and $\delta$ at comparable concentrations (Lingham et al. *J. Antibiot.* 1996, 49, 253).

What is needed are analogs of sandramycin having enhanced cytotoxic activities against various tumor cell lines and sandramycin analogs having inhibitatory activity against reverse transcriptase. Furthermore, what is needed are active analogs of sandramycin which can be synthesized from economically accessable sources.

BRIEF SUMMARY OF THE INVENTION

The invention is directed to sandramycin analogs which possesses unique and specific properties against various leukemia, melanoma, carinoma, and adenocarcinoma cells. The invention is also directed to analogs having inhibitory activity with respect to HIV-1 reverse transcriptase. The synthesis of a series of these analogs is carried out by the penultimate introduction of substitution chromophores on a key intermediate (23). Each analog contains a deep-seated structural change in the chromophore including the deletion of key functional groups or core structural elements which reveals each functional groups role in the high affinity bis-intercalation binding of sandramycin.

One aspect of the invention is directed to Sandramycin analogs following structure:

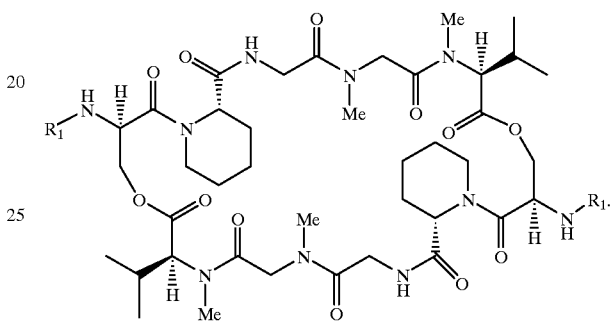

In the above structure, $R_1$ is a radical represented by any of the following structures:

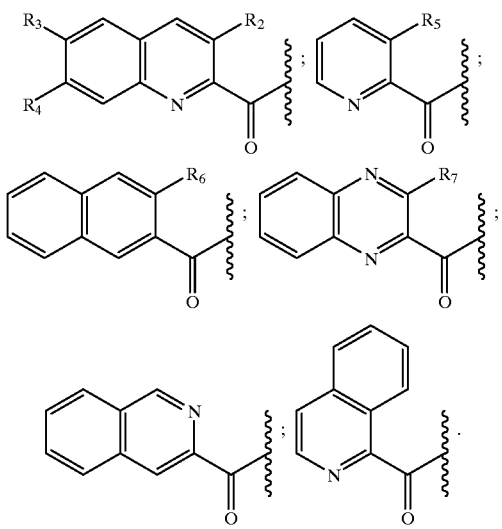

$R_2$ is a radical selected from hydrogen, —OH, —OBenzyl, and —Omethyl. $R_3$ is a radical selected from hydrogen, —OMethyl, and Methyl. $R_4$ is a radical selected from hydrogen and —Cl.

$R_5$ is a radical selected from hydrogen, —OH, and O-Benzyl.

$R_6$ is a radical selected from hydrogen, —OH, and O-Benzyl.

$R_7$ is a radical selected from hydrogen, —OH, and O-Benzyl.

Preferred sandramycin analogs are represented by the following structures:

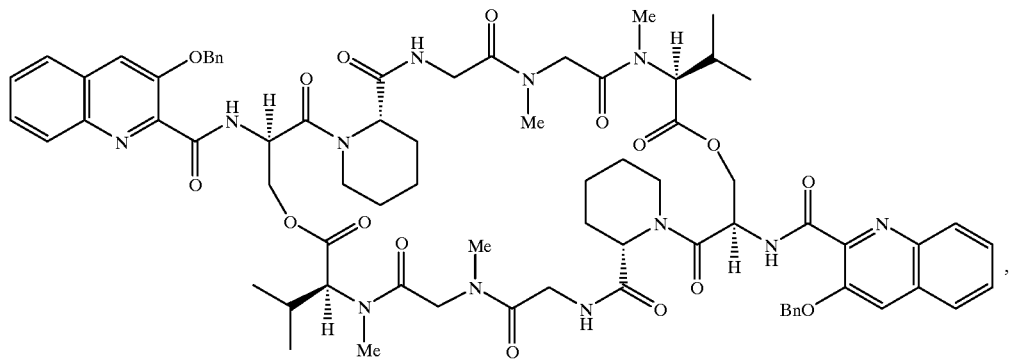
2
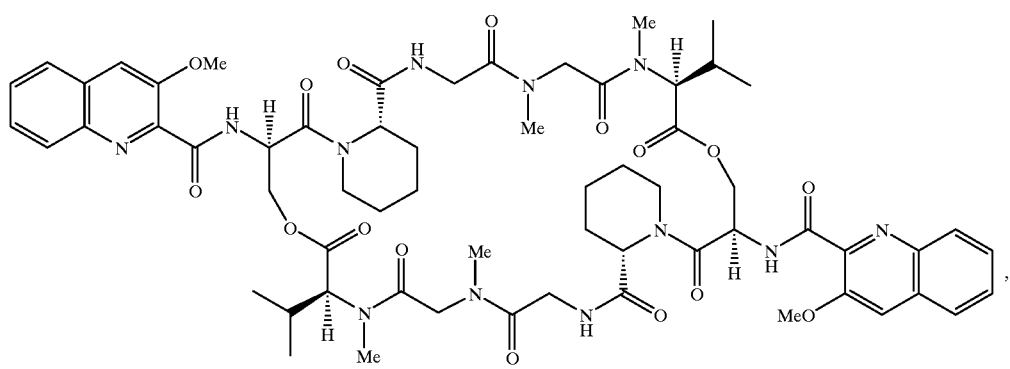
3
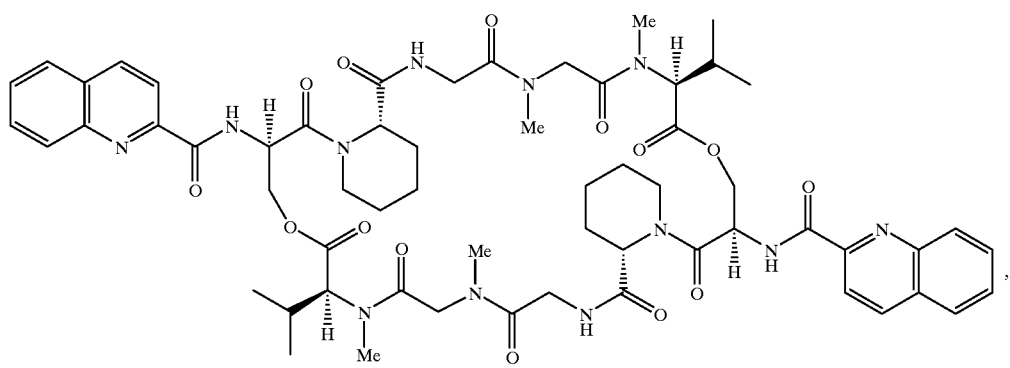
4
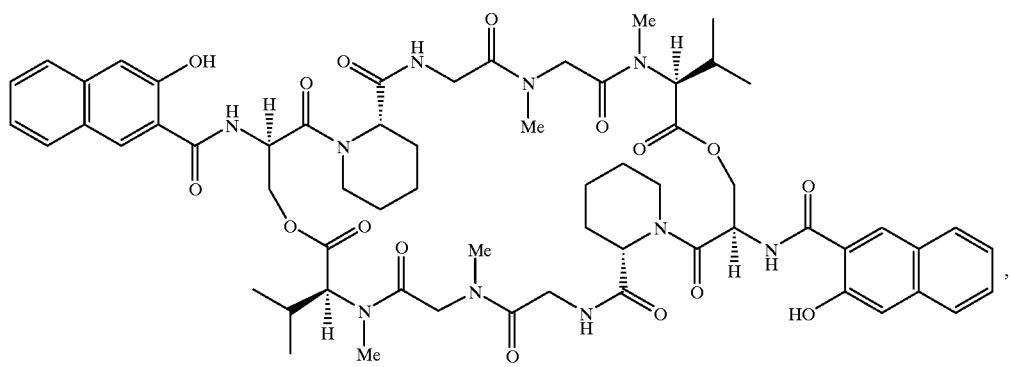
5

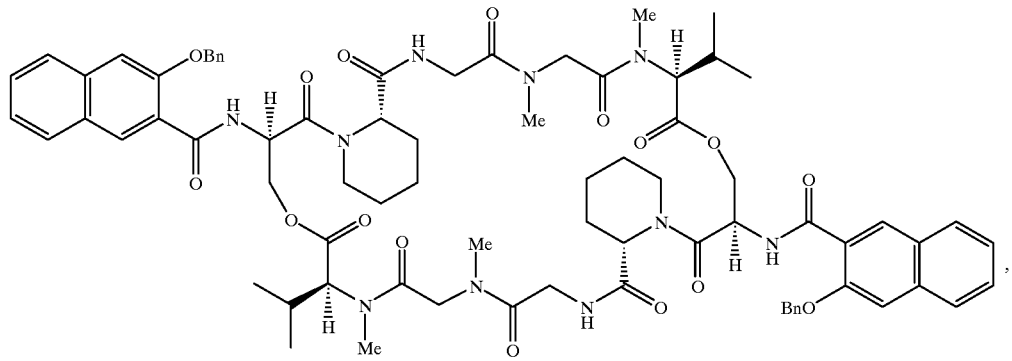
6
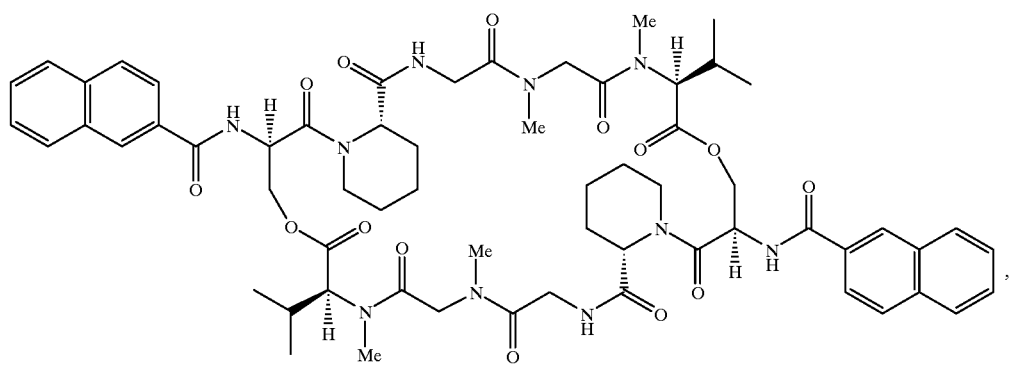
7
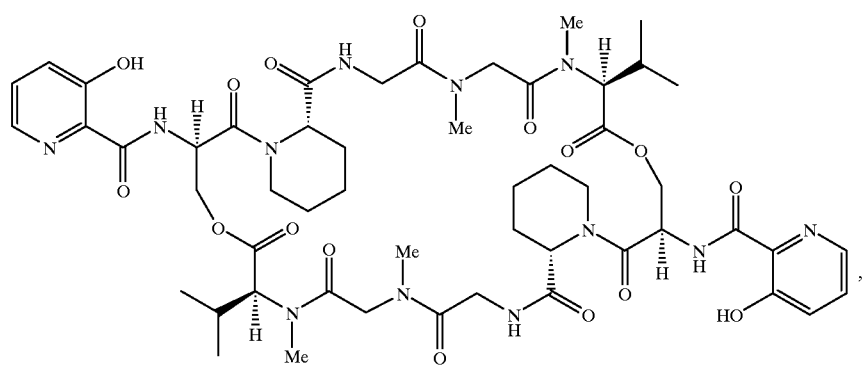
8
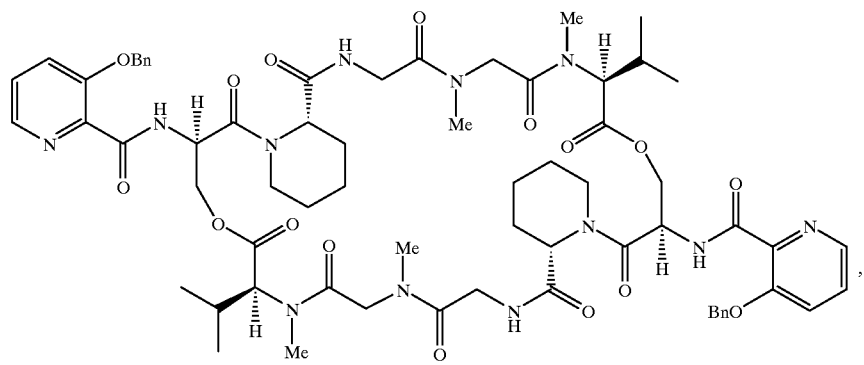
9

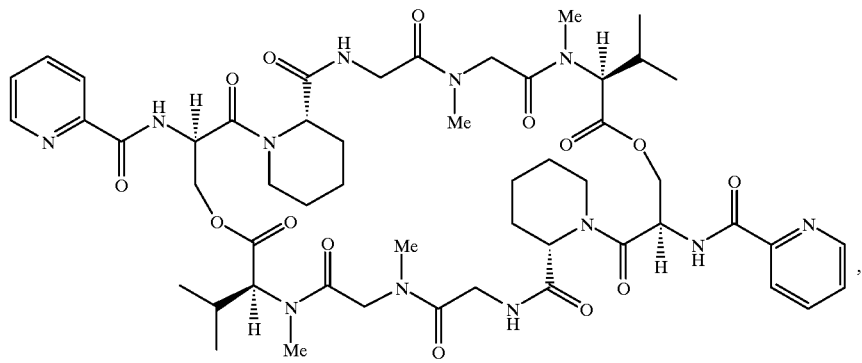
10
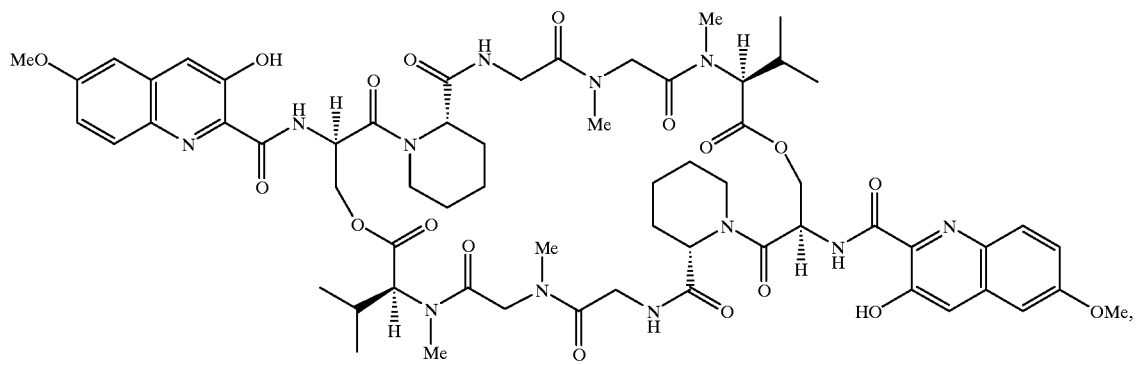
11
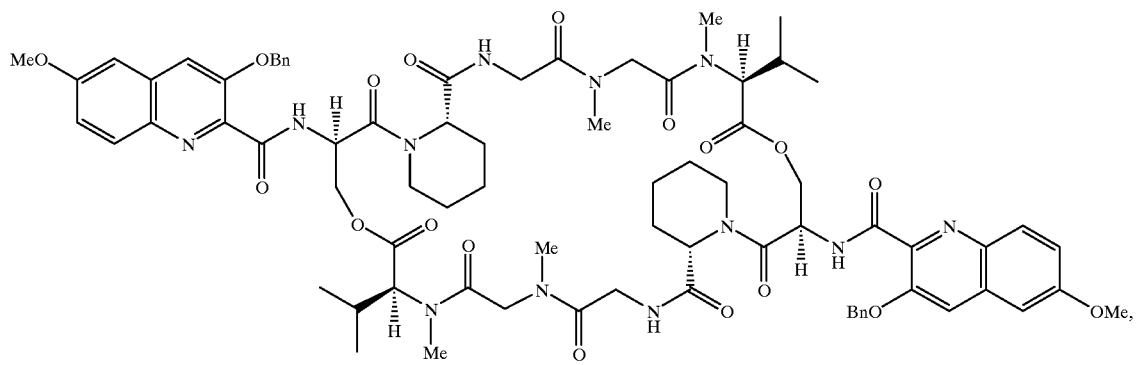
12
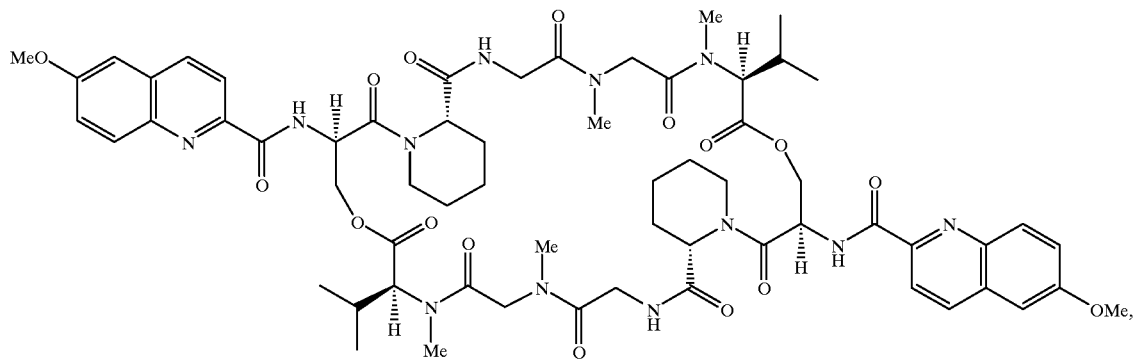
13

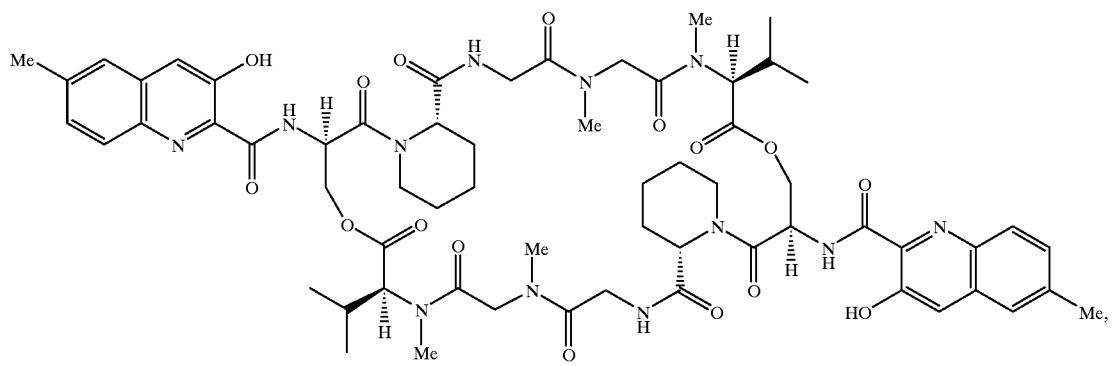
14
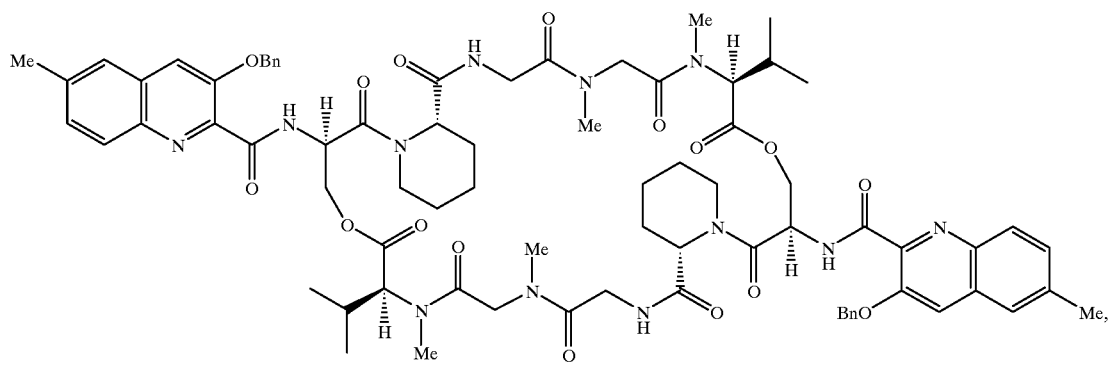
15
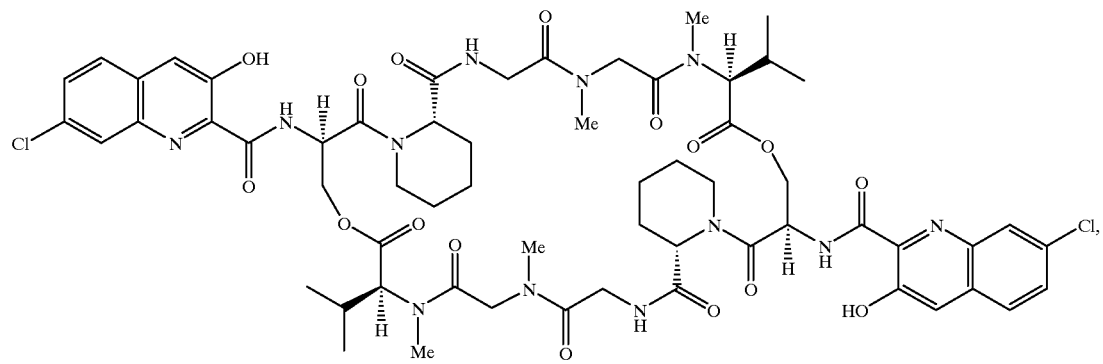
16
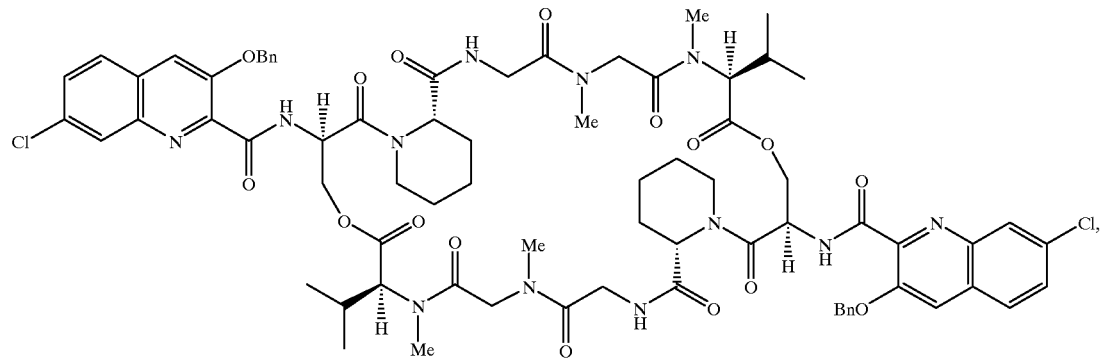
17

-continued
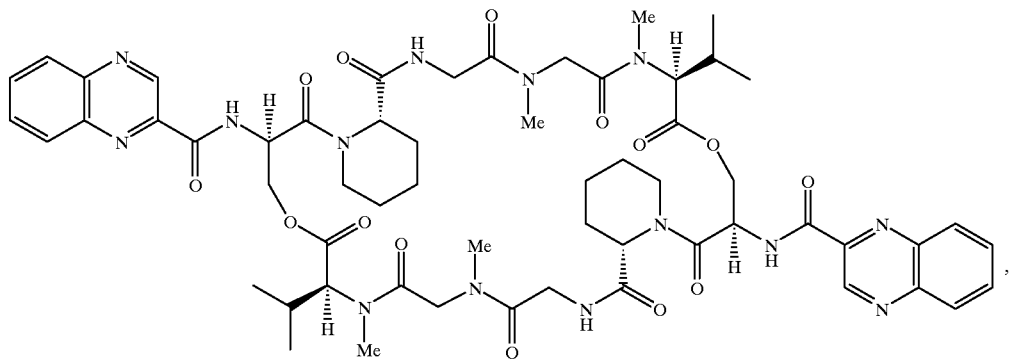
18
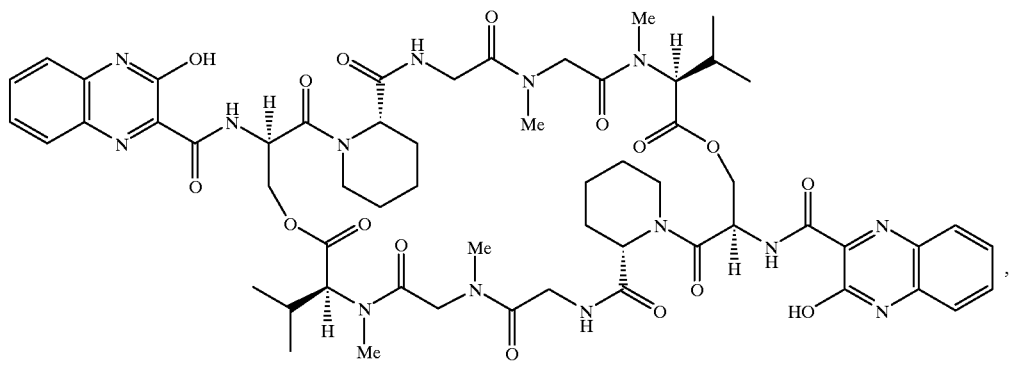
19
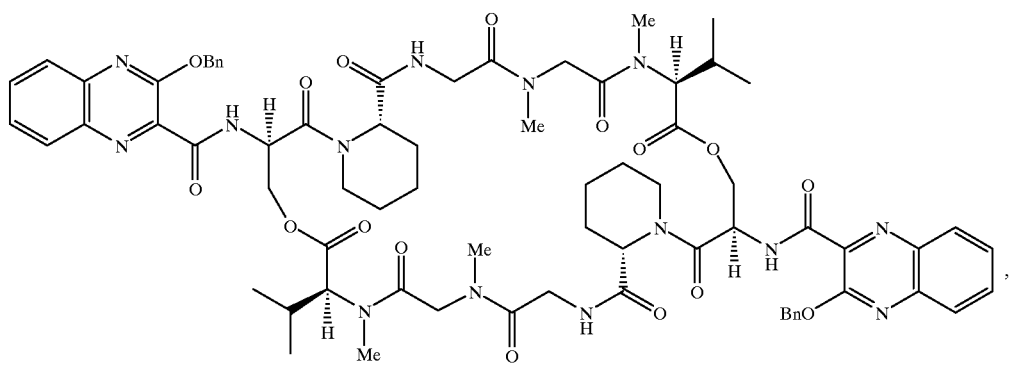
20
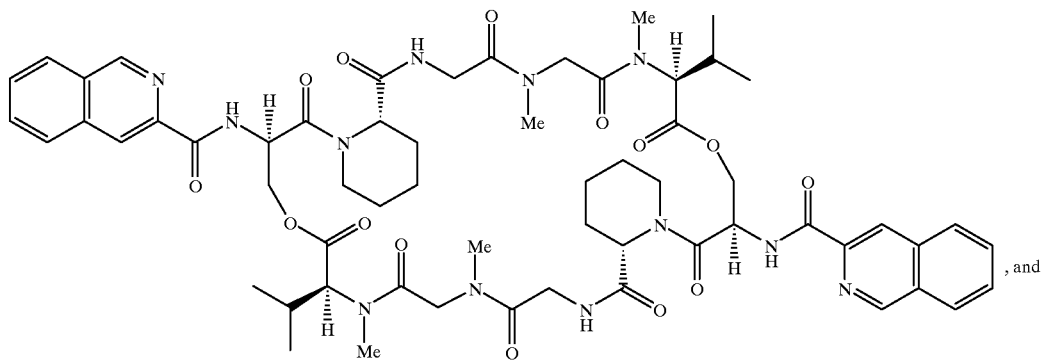
21
, and

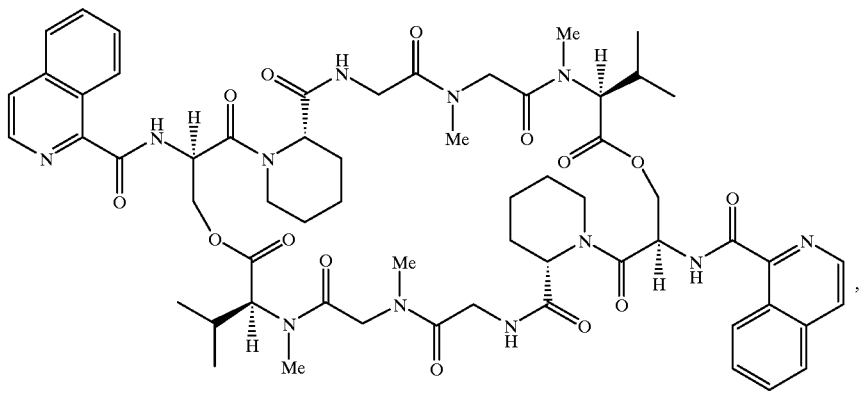

Another aspect of the invention is directed to a topical formulation comprising a sandramycin analog admixed with a pharmaceutically acceptable carrier for treating melanoma. Preferred sandramycin analog are indicated above. A preferred topical formulation for treating melanoma employs a sandramycin analog is represented by the following structure:

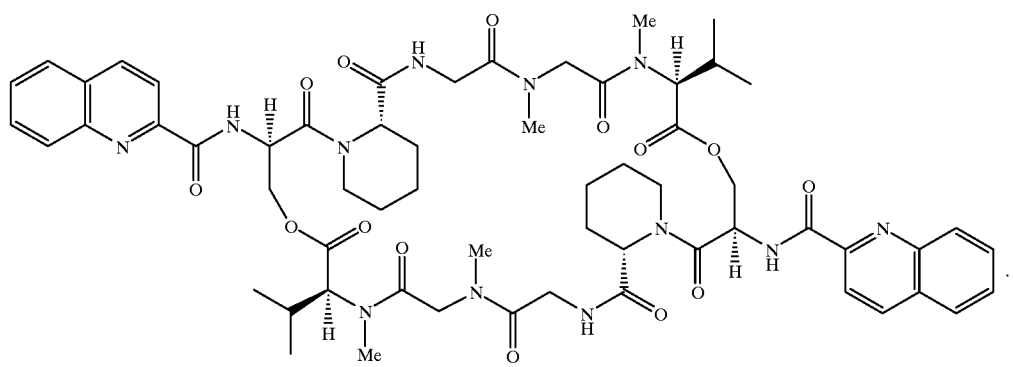

Another aspect of the invention is directed to a method for treating melanoma. The method employs the step of applying the above topical formulation to the melanoma.

BRIEF DESCRIPTION OF THE DRAWINGS

FIG. 1 illustrates sandramycin (1), a potent antitumor antibiotic structurally characterized through spectroscopic and chemical degradation studies; other molecules within the family include luzopeptins A–C and $E_2$, quinaldopeptin and quinoxapeptins A and B which possess potent antitumor, antiviral, and antimicrobial activity.

FIG. 3 illustrates the binding affinity of 23 and 24 with calf thymus DNA which is established to be 2.4 ($10^4$ $M^{-1}$ and 5.7 ($10^6$ $M^{-1}$, respectively). The incremental addition of the chromophores to 23 (G°=−6.0 kcal/mol) increase the binding by 3.2 and 1.0 kcal/mol, respectively.

FIG. 6 illustrates fluorescent excitation wavelengths, emission wavelengths and percent quenching of analog fluorescence.

FIG. 8 illustrates calf thymus DNA and 5'-d(GCATGC)$_2$ binding: fluorescence quenching.

FIG. 9 illustrates sandramycin binding to deoxyoligonucleotides: fluorescence quenching.

FIG. 11 illustrates Sandramycin rate and binding constants for 5'-d(GCXXGCTTTTGCXXGC): surface plasmon resonance.

FIG. 12 illustrates the rate and affinity constants determined for matrix bound 5'-d(GCXXGCTTTTGCXXGC) binding surface plasmon resonance: the figure summarizes the comparison of luzopeptin A, sandramycin (1), and 2 with the chromophore analogs 3–22 in the single L1210 cell line.

FIG. 14 illustrates in vitro cytotoxic activity of key substructure analogs.

FIG. 15 illustrates in vitro cytotoxic activity against L1210 tumor cell lines ($IC_{50}$, nM).

FIG. 17 illustrates in vitro cytotoxic acitivity of 4 against the indicated tumor cell lines ($IC_{50}$, nM) in comparison with the natural products.

FIG. 19 illustrates representative off rates of mono- and bis-intercalators.

FIG. 20 shows the synthesis of 4 from N-BOC deprotection of 23 ($[\alpha]23_D$ –53 (c 1.5, CHCl$_3$), 3 M HCl-EtOAc, 25° C., 30 min) and coupling of the resulting bis amine with quinoline-2-carboxylic acid (4 equiv of EDCI, 6.0 equiv of HOBt, 10 equiv of NaHCO3, DMF, 25° C., 48–72 h, 76–94%).

FIG. 21 illustrates in vitro cytotoxic acitivity of 4 against the indicated tumor cell lines ($IC_{50}$, nM) in comparison with sandramycin.

DETAILED DESCRIPTION OF THE INVENTION

Figure 2:
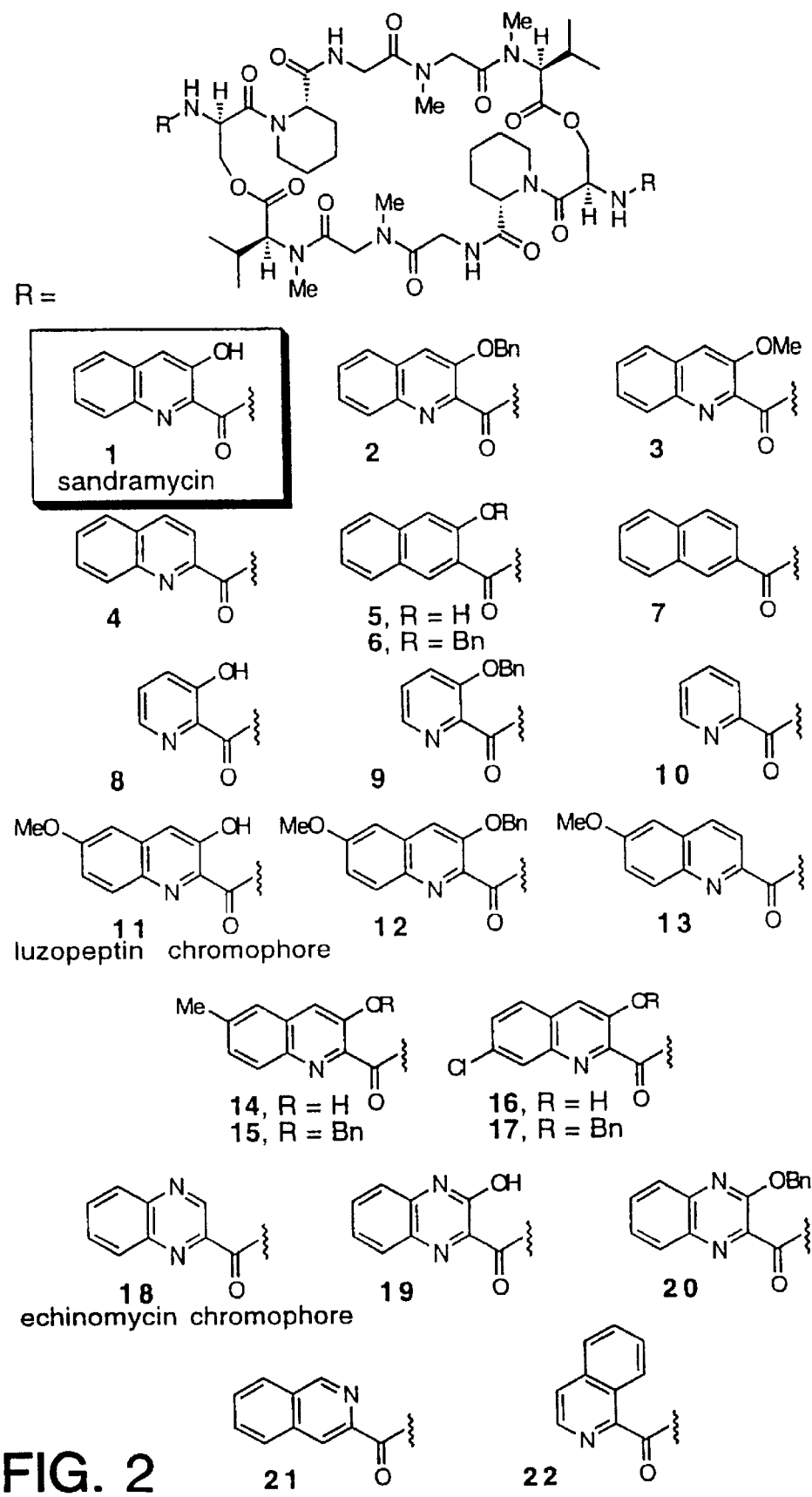
FIG. 2 illustrates the preparation of analogs 2–22 differing only in the structure of the pendant chromophore. Using this approach, incremental changes in the chromophore were used to assess the role of each of its structural components.

The invention relates to the synthesis of a series of analogs of sandramycin (1) accomplished by the penultimate introduction of substitution chromophores on a key intermediate (23). The synthesis of a series of analogs of sandramycin (1) was accomplished by the penultimate introduction of substitution chromophores on the key intermediate 23. Each analog contained a deep-seated structural change in the chromophore including the deletion of key functional groups or core structural elements capable of revealing its role in the high affinity bis-intercalation binding of sandramycin.

Fluorescence quenching studies were employed to establish the DNA binding affinity of sandramycin and the chromophore analogs 2–24 for calf thymus DNA and 5'-d (GCXXGC)$_2$ where XX=AT, TA, GC, and CG. With the latter studies, the determination of absolute binding constants within a single high affinity bis-intercalation site permitted a quantitative assessment of the sequence selectivity of sandramycin (1) as 5'-d(GCATGC)$_2$>5'-d (GCGCGC)$_2$, G°=0.3 kcal/mol>5'-d(GCTAGC)$_2$, 5'-d (GCCGGC), G°=0.6 kcal/mol and a quantitative assessment of the chromophore structural features contributing to binding at a single high affinity bis-intercalation site. The two highest affinity sequences constitute repeating 5'-PuPy motifs with each intercalation event occurring at a 5'-PyPu step. The highest affinity sequence of the pair constitutes the less stable duplex, possesses the sterically most accessible minor groove central to the bis-intercalation site, and the ability to accept the two gly-NH/T C2 carbonyl H-bonds identified in NMR studies. Whether these features, or more subtle features, are responsible for the binding preference will be the subject of continued examination. The chromophore nitrogen inherent in the quinoline-2-carboxylate structure is essential for binding affinity (>1 kcal/mol per chromophore), the fused benzene ring contributes substantially (ca. 1.1 kcal/mol per chromophore) while the C3 phenol only slightly enhances binding (0.5 kcal/mol per chromophore). The addition of C6 or C7 substituents only slightly diminishes binding affinity and the luzopeptin chromophore incorporating a C6 methoxy substituent was established to be slightly less effective than the sandramycin chromophore. These studies suggest substantial modifications may be made at both the C6 and C7 positions without adversely affecting binding affinity but none to date have been observed to enhance binding.

To a first approximation, the cytotoxic properties of the agents and their ability to inhibit HIV-1 reverse transcriptase were found to follow trends established in the DNA binding affinities. The exception to this generalization was 4 which lacks the chromophore phenol. Although it was found to be typically 4–10(less potent than luzopeptin A or sandramycin against leukemia cell lines, it proved to be equipotent or more potent against melanomas, carcinomas, and adenocarcinomas. In these latter tumor types, it was found to exhibit cytotoxic potencies ranging from 1 pM to 10 nM which was 1–10,000× more potent than luzopeptin A or sandramycin placing it among the most potent agents identified to date. Although many explanations may account for such observations, one of the most obvious is that the removal of the acidic phenol may lead to better target delivery without adversely affecting the DNA binding affinity or selectivity.

EXAMPLE 1

Synthesis and Evaluation of Key Sandramycin Analogs: Systematic Examination of the Intercalation Chromophore In this example, the preparation and examination of 2–22 constituting a systematic study of the chromophore of sandramycin (1) are detailed. Fluorescence quenching studies were used to establish binding constants for 1–24 within calf thymus DNA, within a single high affinity bis-intercalation binding site 5'-d(GCATGC)$_2$, and to establish the preference for sandramycin binding to 5'-d(GCXXGC)$_2$ where XX=AT, TA, GC, and CG. From the latter studies, sandramycin was found to exhibit a preference that follows the order: 5'-d (GCATGC)$_2$>5'-d(GCGCGC)$_2$, G°=0.3 kcal/mol>5'-d (GCTAGC)$_2$, 5'-d(GCCGGC)$_2$, G°=0.6 kcal/mol although it binds with high affinity to all four deoxyoligonucleotides. The two highest affinity sequences constitute repeating 5'-PuPy motifs with each intercalation event occurring at a 5'-PyPu step. The most effective sequence constitutes the less stable duplex, contains the sterically most accessible minor groove central to the bis-intercalation site, and the ability to accept two gly-NH/T C2 carbonyl H-bonds identified in prior NMR studies. Similarly, the contribution of the individual structural features of the chromophore were assessed with the high affinity duplex sequence 5'-d (GCATGC)$_2$. To a first approximation, the cytotoxic properties were found to parallel trends established in the DNA binding affinities.

The exception to this generalization was 4 which lacks the sandramycin chromophore phenol. Although typically 4–10 (less potent than sandramycin against leukemia cell lines, it proved to be 1–10,000(more potent against melanomas, carcinomas, and adenocarcinomas exhibiting IC$_{50}$ values of 1 pM–10 nM placing it among the most potent agents identified to date.

Another embodiment of the invention is the finding of HIV-1 reverse transcriptase inhibitory activity of sandramycin (1) as well as that of its key analogs and which define the chromophore structural features required for their exceptional potency. Two analogs, 18 and 3, roughly maintain the HIV-1 reverse transcriptase inhibitory potency of 1 but exhibit substantially diminished cytotoxic activity ($10^2$–$10^3$).

We recently disclosed a convergent total synthesis of sandramycin in which the heteroaromatic chromophores were introduced in the final stages (Boger et al. *J. Am. Chem. Soc.* 1996, 118, 1629; Boger et al. *J. Am. Chem. Soc.* 1993, 115, 11624). This not only provided sufficient quantities of the natural product to define its DNA binding properties, but also the key partial structures lacking one or both of the pendant chromophores.

This has now been extended to the preparation of 2–22 differing only in the structure of the pendant chromophore (FIG. 2). Using this approach, incremental changes in the chromophore were used to assess the role of each of its structural components.

DNase I footprinting experiments have demonstrated that sandramycin, like the luzopeptins, shows a slight preference for regions of DNA containing alternating A and T residues with a perceptible preference for 5'-AT dinucleotide sequences most often preceded by a 5'-C, i.e. 5'-CAT. As with the luzopeptins, the binding mode was confirmed by $^1$H NMR studies of a C$_2$-symmetric 1:1 complex of sandramycin with 5'-d(GCATGC)$_2$ in which the agent was found to bind by bis-intercalation about the central 5'-AT base-pairs. DNA binding affinity established by fluorescence quenching of the agent with calf thymus DNA revealed that sandramycin (3.4 ($10^7$ M$^{-1}$) exhibited a slightly higher apparent binding constant than luzopeptin A (1.2 ($10^7$ M$^{-1}$). A larger base-pair:agent ratio was also found for sandramycin, 1:6.7 versus 1:4.5, implying an increased selectivity.

Although these studies demonstrated effective bis-intercalation at 5'-AT, they did not exclude the possibility of binding at other sites. This possibility was supported by footprinting experiments which showed that at low agent concentrations, 5'-AT and especially 5'-CAT sites were protected but at moderate agent concentrations, the DNA was almost evenly protected from digestion. In order to probe this binding selectivity, herein we provide details of the comparative binding of sandramycin with 5'-d(GCXXGC)$_2$ where XX=AT, TA, GC, and CG.

The binding affinity of 23 and 24 with calf thymus DNA was established to be 2.4 ($10^4$ M$^{-1}$ and 5.7 ($10^6$ M$^{-1}$, respectively (FIG. 3). Thus, the incremental addition of the chromophores to 23 (G°=–6.0 kcal/mol) increase the binding by 3.2 and 1.0 kcal/mol, respectively. This is consistent with the representation of sandramycin and the luzopeptins as minor groove binding cyclic decadepsipeptides incrementally stabilized by mono- and bis-intercalation. To further define the role of the chromophores, the binding affinity of 2–22 with both calf thymus DNA and 5'-d(GCATGC)$_2$ are also described. In these studies, the correlation of structural changes in the chromophore with the resulting changes in the binding affinity not only permitted the determination of the structural features contributing to the high affinity bis-intercalation binding, but their absolute magnitude as well. Preparation of 3–22.

Figure 4:
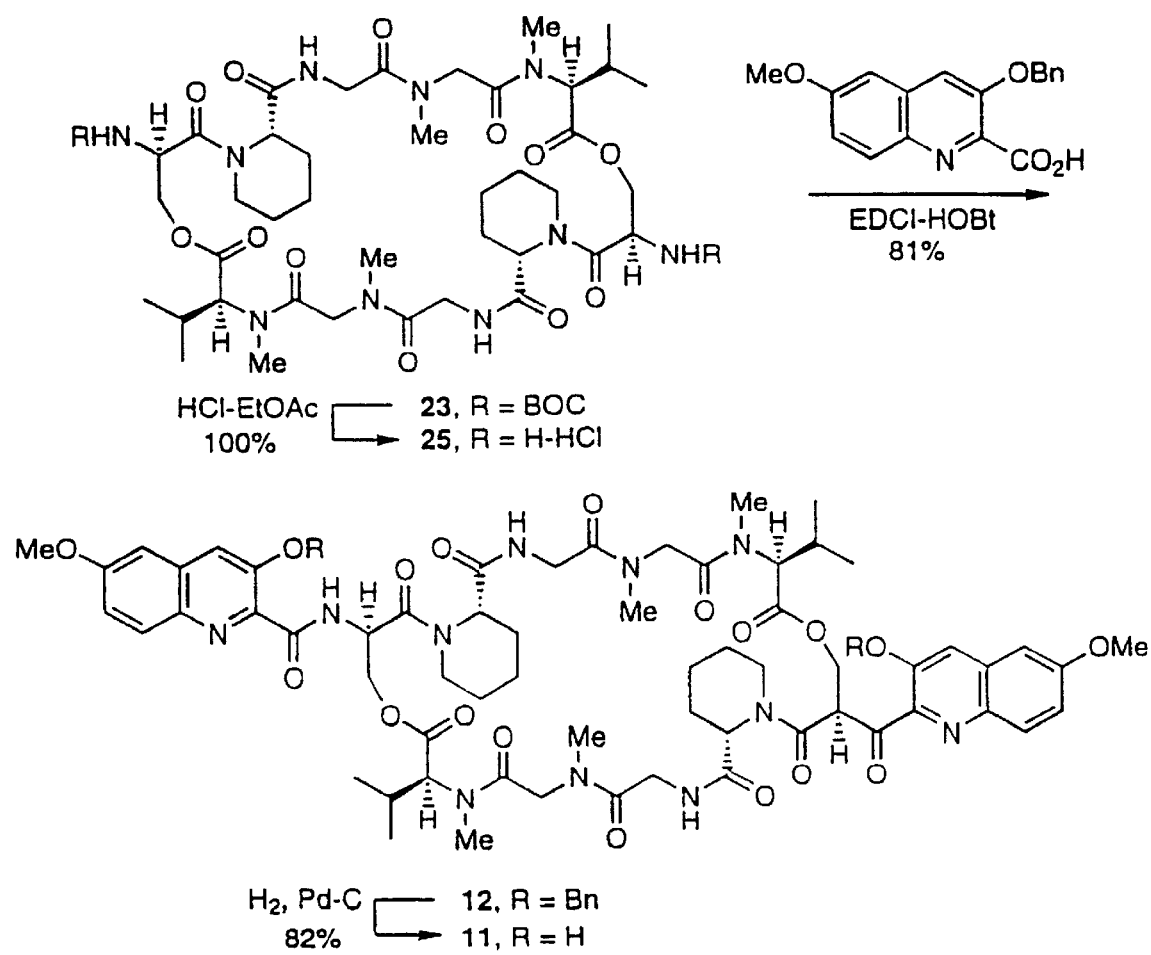
FIG. 4 illustrates the preparation of 11 and 12 which constitutes the incorporation of the luzopeptin chromophore into the sandramycin structure.

The synthesis of the agents including those that contain the luzopeptin or echinomycin chromophores required N-BOC deprotection of 23 ([$\alpha$]$^{23}$D –53 (c 0.15, CHCl$_3$), 3 M HCl-EtOAc, 25° C., 30 min), coupling of the resulting bis amine 25 with the appropriate carboxylic acids (4 equiv of EDCI, 6.0 equiv of HOBt, 10 equiv of NaHCO$_3$, DMF, 25° C., 48–72 h, 76–94%) and, when required, final deprotection of the bis-O-benzyl derivatives 6, 9, 12, 15, 17 or 20 (H$_2$, 10% Pd—C, EtOAc, 25° C., 14–24 h, 78–94%). This is illustrated in FIG. 4 with the preparation of 11 and 12 which constitutes the incorporation of the luzopeptin chromophore into the sandramycin structure.

Figure 5:
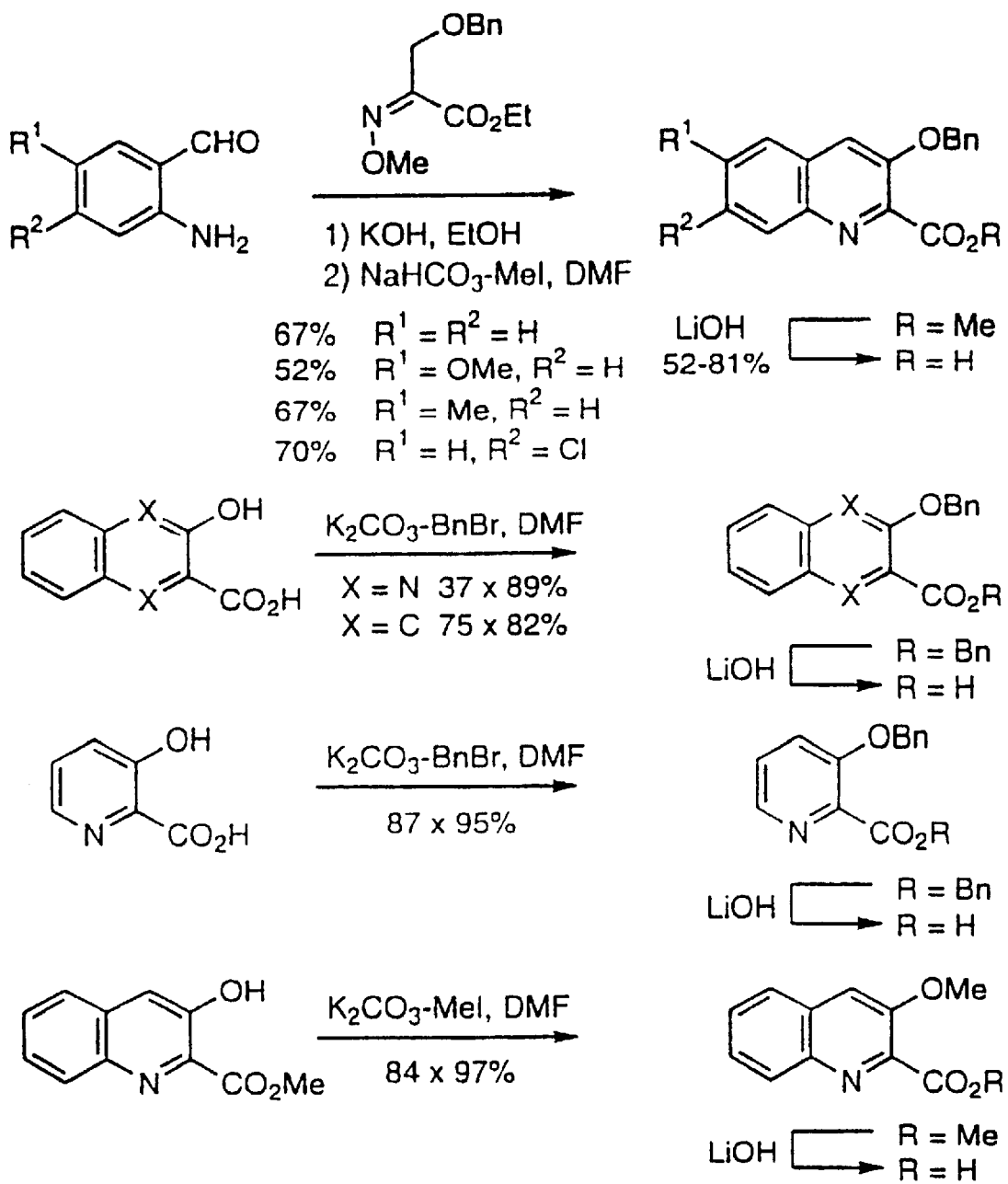
FIG. 5 illustrates the synthesis of carboxylic acids for the introduction of the chromophores of 1–2, 11–12, 14–15, and 16–17 which were derived through use of a modified Friedlander condensation employing the readily accessible O-methyloxime.
Figure 7A:
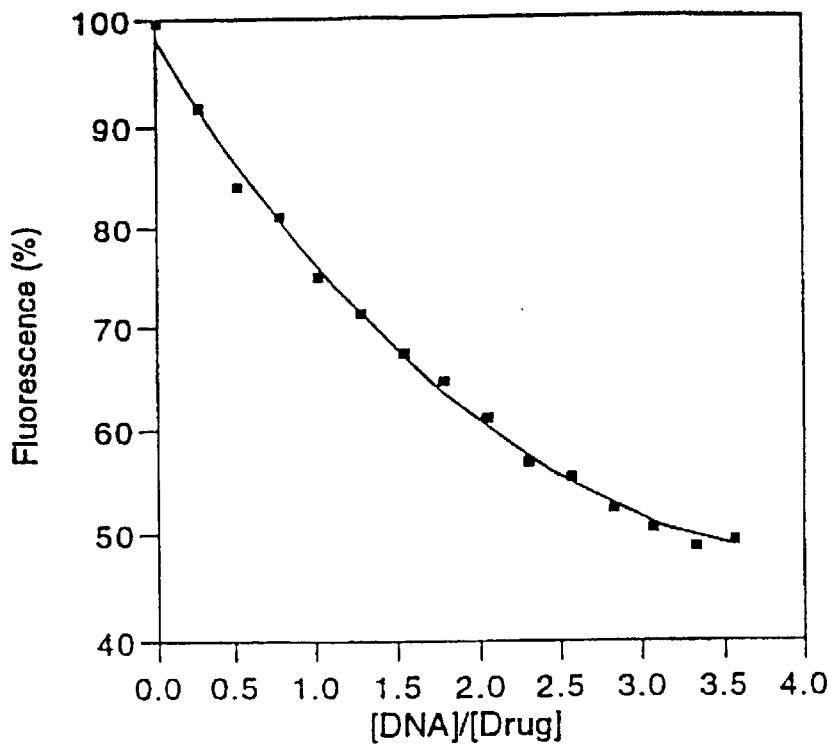
FIG. 7 illustrates fluorescence quenching of agent 4 (excitation at 286 nm and emission at 410 nm in 10 mM Tris-HCl (pH 7.4) and 75 mM NaCl buffer solution) with increasing (a) calf thymus DNA concentration and (b) increasing 5'-d(GCATGC)$_2$ concentrations. Scatchard plots of fluorescent quenching of agent 4 with (c) calf thymus DNA (linear fit of high affinity sites) and (d) 5'-d (GCATGC)$_2$ (non-linear fit).
Figure 7B:
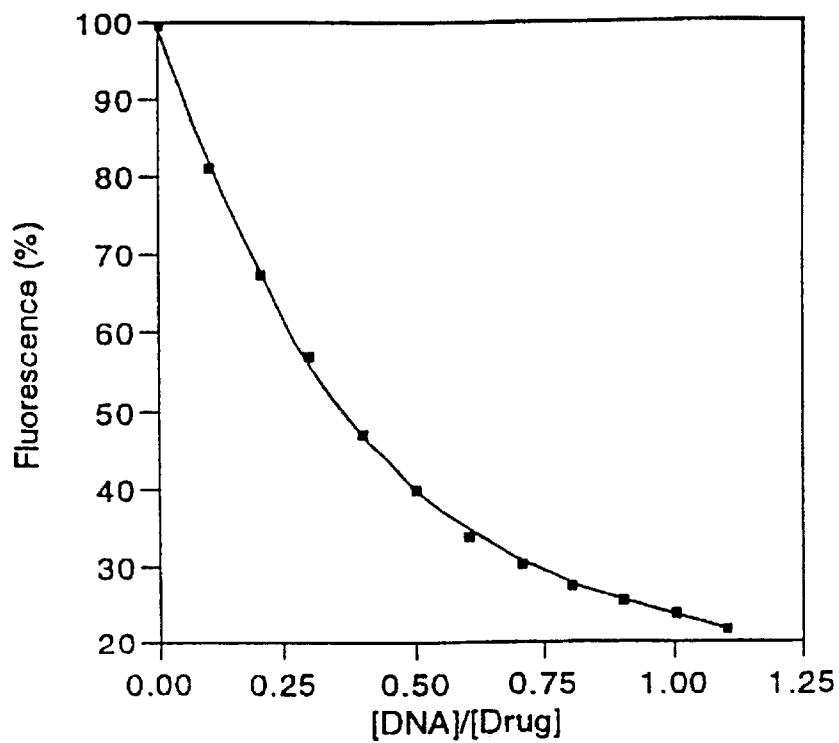
Figure 7C:
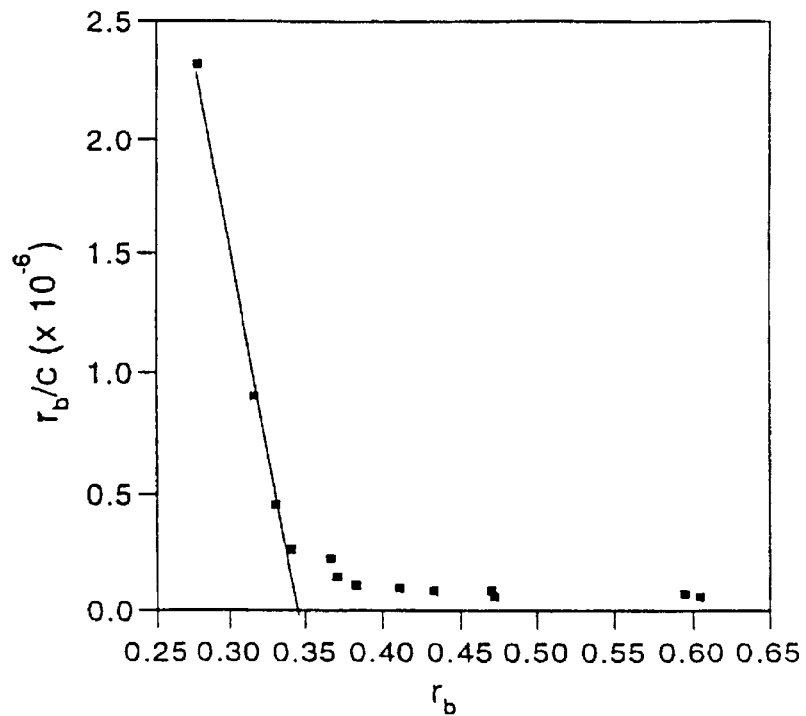
Figure 7D:
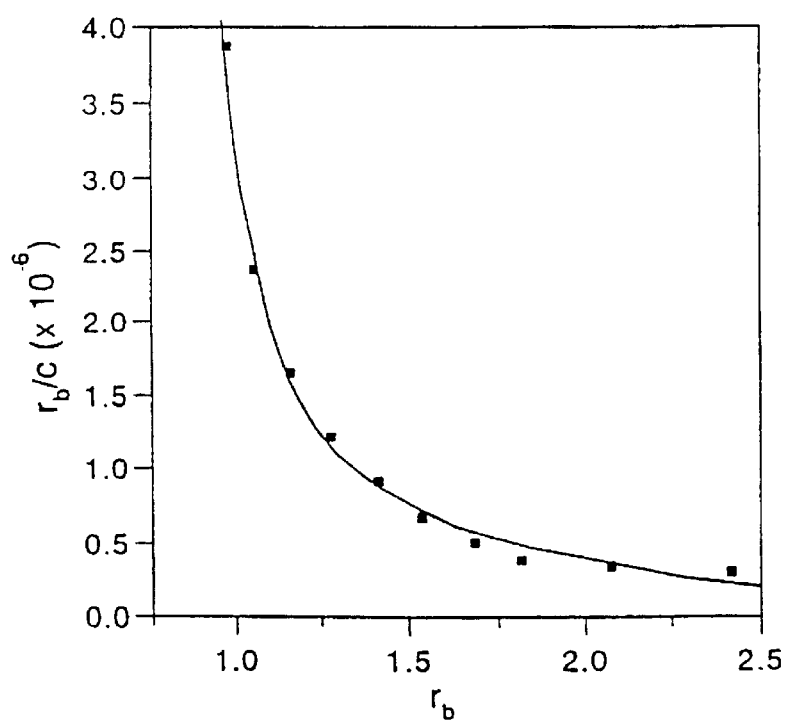

The required four carboxylic acids for the introduction of the chromophores of 1–2, 11–12, 14–15, and 16–17 were derived through use of a modified Friedlander condensation employing the readily accessible O-methyloxime (FIG. 5).

The aryl 3-benzyloxy-2-carboxylic acids required for introduction of the chromophores for 5–6, 8–9, and 19–20 were prepared by perbenzylation of the corresponding 3-hydroxy-2-carboxylic acids (3 equiv BnBr, K$_2$CO$_3$, DMF, 25° C., 4 h) followed by hydrolysis of the resulting benzyl ester (LiOH, THF—CH$_3$OH—H$_2$O, 25° C.). Similarly, the chromophore for 3 was prepared by O-methylation of methyl 3-hydroxyquinoline-2-carboxylate (CH$_3$I, K$_2$CO$_3$, DMF, 25° C., 84%) followed by methyl ester hydrolysis. 6-Methoxy-quinoline-2-carboxylic acid was obtained by hydrolysis of 2-cyano-6-methoxyquinoline (25% aqueous NaOH, CH$_3$OH, 80%, 4 h, 77%). The remainder of the carboyxlic acids used for the chromophore introduction were commercially available.

Conformational Properties of 1 and the Related Cyclic Decadepsipeptides.

The single crystal X-ray structure determination of 23 (Boger et al. *J. Am. Chem. Soc.* 1996, 118, 1629. Boger et al. *J. Am. Chem. Soc.* 1993, 115, 11624). Revealed a backbone conformation nearly identical to that of luzopeptin A. The most significant perturbation of the two structures was the twisted orientation of the linking esters. The relative placement of the ring nitrogens and the backbone conformation of the pentapeptides excluding the ester atoms are even more similar in the two structures. The overall shape of the agent is rectangular with a two-fold axis of symmetry. The long sides of the rectangle consist of antiparallel and twisted-extended chains capped on either end by the two decadepsipeptide ester linkages. Each of the amides including the three tertiary amides adopt a trans or extended stereochemistry and the two decadepsipeptide esters adopt the preferred syn conformation. The two symmetrical secondary amide NH's of glycine are engaged in tight transannular H-bonds (2.08 Å, gly-NH—O=C-gly) to the glycine carbonyl oxygen across the ring and cap two reverse peptide turns induced in part by the incorporation of unnatural D-serine at one corner of each turn. The pipecolic acid residue adopts a classical chair conformation with the -carboxylate adopting an axial position and skewed by approximately 48° from the optimal anti relationship of the carbonyl to the C—H. In this conformation the D-ser-NH/D-ser-NH distance is 15.1 Å. The comparable luzopeptin A D-ser-NH/D-ser-NH distance is 14.8 Å and the distance between the centers of the two chromophores in this X-ray is 17.4–19.9 Å. The 1D $^1$H NMR of 2–22 indicate that they adopt a single, rigid solution conformation comparable to that observed with sandramycin and 23. In all solvents except DMSO-$d_6$, the agents adopted a single, rigid solution conformation comparable to that observed in the X-ray. This conformation is inherent in the cyclic depsidecapeptide and independent of the pendant chromophore.

The bis-intercalation spans two base-pairs and requires the adoption of a conformation in which the two chromophores are separated by 10.1–10.2 Å. However, the X-ray conformation and the related solution phase conformation of 1–22 adopt a more extended conformation in which the interchromophore distance is 17–19.5 Å. Thus, the agents must adopt an altered conformation upon bis-intercalation DNA binding that is substantially different than its preferred native X-ray or solution conformation. Both the pip-gly secondary amides and the tertiary gly-sar amides adopt cis versus trans amide stereochemistries in order to accommodate this shorter distance and the bound conformations of the agent maintains its 2-fold axis of symmetry. The gly NH's are reoriented to form intermolecular H-bonds with the thymine C2 carbonyls and nicely explain the preference for the 5'-AT sequence. Complementary intermolecular hydrophobic contacts extend over much of the interacting surface. These observations have suggested that the relatively low contribution to the binding affinity attributable to the second intercalation is due to an accompanying destabilizing conformational change in the cyclic decapeptide that offsets much of the gains derived from a second intercalation.

DNA Binding Affinity and Selectivity.

Apparent absolute DNA binding constants for 1–22 and related agents including luzopeptin A were obtained by measurement of the fluorescence quenching upon titration addition of calf thymus DNA or the deoxyoligonucleotides 5'-d(GCXXGC)$_2$ where XX=AT, TA, GC, and CG. For each agent, the characteristic fluorescence excitation and emission spectra were recorded in 10 mM Tris-HCl, 75 mM NaCl (pH 7.4) buffer, FIG. 6. For the DNA binding assays which quantitate the fluorescence quenching, excitation outside the absorbance range of DNA was employed and the most intense fluorescence emission at a longer wavelength monitored. For assay of the DNA-induced fluorescence quenching of the agents, a 2 mL buffer solution of Tris-HCl (pH 7.4) and 75 mM NaCl was employed. For titration, small aliquots of DNA were added to solutions of the agents in Tris-HCl buffer (pH 7.4).

The addition of DNA caused a marked quenching effect on the fluorescence of the agents. The DNA quenching of fluorescence ranged from 52–92% as summarized in FIG. 6. The analogs 5, 7, 18, and 19 were not sufficiently soluble to examine in this assay. Due to the inner filter effect, choosing the excitation wavelength at a UV absorbance peak maximum may lead to non-linear Beer's law plots of intensity versus concentration affecting the results of the fluorescence quenching studies. However, plots of fluorescence versus intensity proved to be linear throughout the concentration ranges in our study. To minimize fluorescence decrease due to dissolution or photobleaching, the solutions were stirred in 4 mL quartz cuvettes shielded from light in a darkened room with the minimum exposure to the excitation beam necessary to obtain a reading.

Despite these precautions, the fluorescence for a number of the analog solutions decreased for several of analogs (11, 14, 17, 21 and 22) and the quality of the binding constants for these should be viewed with caution. The fluorescence decreases were not effected by taking multiple readings indicating that the observations are not due to photobleaching. This effect was less significant in the quartz versus plastic cuvettes and could be minimized by increasing the concentration of DMSO suggesting the effects may be due to aggregate formation. The titrations were carried out with 15 min time intervals between DNA additions to allow binding equilibration. Notable differences have not been detected with different time intervals (10–30 min) indicating that tight binding equilibration is rapid and the results of the study are summarized in FIG. 8. The titration fluorescence quenching was analyzed by Scatchard analysis (Scatchard, G. *Ann. N. Y. Acad. Sci.* 1949, 51, 660) with the following equation: $r_b/c=K_bn-K_br_b$, where $r_b$ is the number of agent molecules bound per DNA base-pair, c is the free drug concentration, $K_b$ is the apparent association constant, and n is the number of agent binding sites per base-pair. From a plot of $r_b/c$ versus $r_b$, as shown in FIG. 7 for 4, association constants ($K_b$) for 1–22 and luzopeptin A were derived from the slope and the binding site sizes determined from the x-intercept values (n) for the number of agent binding sites per base-pair. The results are summarized in FIG. 8.

Typical of such studies, the Scatchard plots exhibited a downward convex curvature which reduced to straight lines at the extremes indicating high and low affinity binding. A pronounced downward curvature in an infinite lattice such as calf thymus DNA is recognized to arise in part from neighbor exclusion where the binding of an agent excludes the subsequent binding at nearby sites. This exclusion manifests itself in the plot by a reduction in the apparent binding constant as the DNA lattice approaches saturation and the probability of finding a free site is diminished. In the calf thymus DNA studies, the binding also entails multiple classes of independent binding sites or modes. For simplicity, a linear fit of the high affinity binding sites was used to determine the binding constant attributable to bis-intercalation. For the deoxyoligonucleotides, the curvature can be more simply attributed to multiple classes of independent binding sites or binding modes. There are a number of mathematical methods to deconvolute the curved plot into such individual binding events. In the deoxyoligonucleotide studies, a non-linear fit described by Feldman was also used to deconvolute the curves. The model assumes one ligand with two binding types or sites. Since the number of binding sites is limited, we have interpreted this to indicate a high affinity bis-intercalation and a lower affinity binding potentially involving mono-intercalation. The formula was fit using the JMP[22] statistical fitting program using an initial approximation of the two n values and fitting for $K_1$ and $K_2$. Regardless of the interpretation, the results obtained taking into account the lower affinity binding with the second method provides a slightly higher binding constant for the high affinity binding event but, in general, did not alter the overall qualitative or relative quantitative trends in binding.

Figure 10:
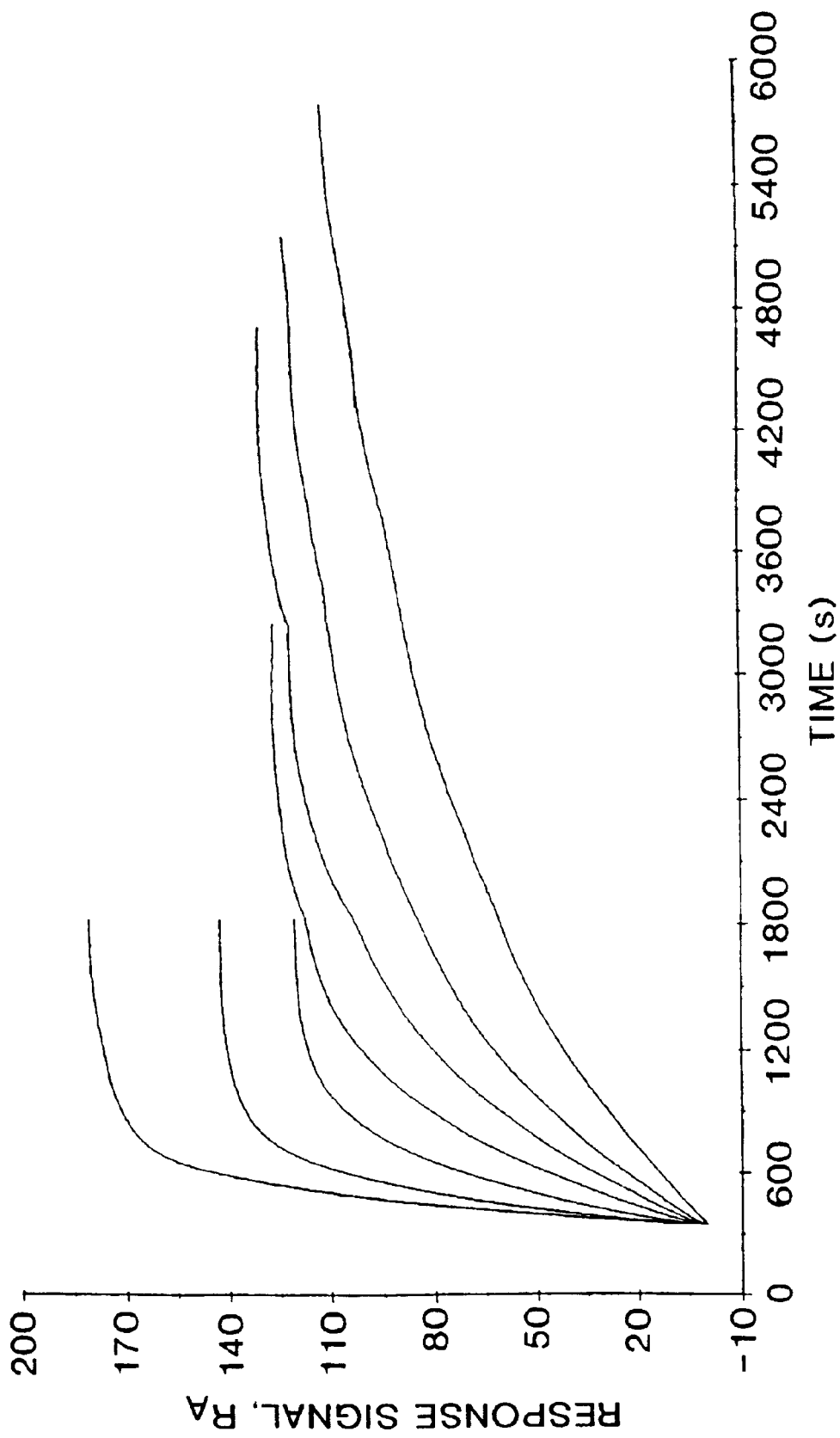
FIG. 10 illustrates data obtained from one of the four flow cells of a Pharmacia Biosensor chip containing immobilized streptavidin at a volume concentration of 23 mg/mL with a 2:1 ratio of bound 5'-biotinylated 5'-d (GCATGCTTTTGCATGC) to streptavidin. Sandramycin (1), dissolved in a 10 mM Tris-HCl (pH 7.4) buffer solution containing 75 mM NaCl was passed through the flow cell at a rate of 10 micro-liter/min at 25° C. (a) Plot of slope value k, versus sandramycin concentration c according to equation 4. (b) Analysis of steady state binding according to equation 3. (c) Sensorgram illustrating affinity and kinetic measurements of sandramycin. The concentrations of the agent, c, are as follows beginning with the maximum response signal: $5\times10^{-6}$, $1\times10^{-6}$; $7.5\times10^{-7}$, $5\times10^{-7}$, $3\times10^{-7}$, $1\times10^{-7}$; and $5\times10^{-8}$ M corresponding to the lowest response signal. (Instrument noise at each 250 µL injection was removed and the resulting curves were spliced together).
Figure 10A:
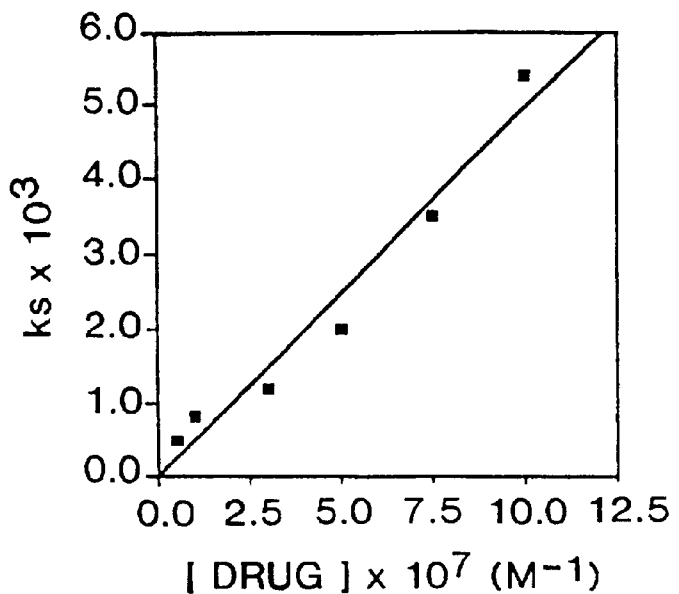
Figure 10B:
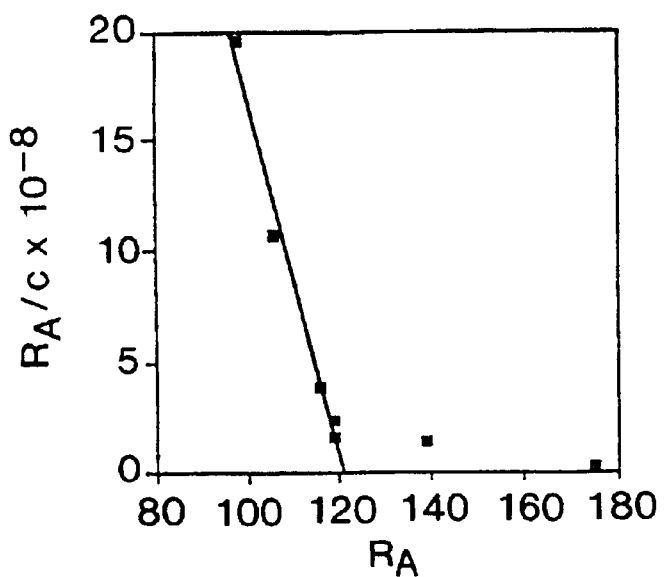

The studies with calf thymus DNA and 5'-d(GCATGc)$_2$ provided comparable results. Both the relative trends in binding affinity and the quantitative differences were comparable regardless of the DNA employed although the deoxyoligonucleotide typically provided higher binding constants. We attribute this to the difference in measuring the absolute binding constant at a single high affinity site within 5'-d(GCATGC)$_2$ versus the apparent absolute binding constant for the composite of sites within calf thymus DNA. Several important trends emerged from these studies, (FIG. 10). First, either O-methylation of the chromophore phenol or its removal altogether resulted in a comparable reduction of the binding affinity. This typically proved to be worth 1.5–0.8 kcal/mol (1 versus 3 and 4). This suggests that each hydroxyl group contributes approximately 0.5 kcal/mol toward the binding affinity of sandramycin. Similar trends were observed in comparing 11 and 13. In contrast to this modest effect, O-benzylation of the chromophore phenol had a much larger effect reducing the binding affinity by 2.4–2.7 kcal/mol (16 versus 17). Thus, significant perturbations including the complete removal of the phenol may be well tolerated while more substantial changes including the substitution with large groups (i.e., O-benzylation) substantially reduces the binding affinity providing agents that are only comparable to 23 which lacks both chromophores altogether. Secondly, the luzopeptin chromophore proved slightly less effective illustrating that the C6 methoxy group is not contributing significantly or productively to the DNA binding affinity (1 versus 11). Similar observations were made in the comparisons of 4 with 13. Likewise, the introduction of a C6 methyl group (14) or C7 chlorine substituent (16) did not have a substantial effect on the DNA binding affinity although 16 typically was nearly indistinguishable from 1 while 14 was consistently slightly less effective. Thus, significant perturbations at the C6 and C7 positions are tolerated although none were found to productively contribute to DNA binding affinity. The reduction of the chromophore to the 3-hydroxypyridine-2-carboxylate with removal of the fused benzene ring with 8 resulted in a large drop in DNA binding affinity costing 1.7 kcal/mol in calf thymus DNA and 2.3–2.6 kcal/mol with 5'-d(GCATGC)$_2$. Finally, the behavior of 21 and 22 relative to 1 and 4 proved interesting. Although 22 proved comparable to 4 with calf thymus DNA, both 21 and 22 were substantially less effective at binding with 5'-d(GCATGC)$_2$. This suggests that the quinoline-2-carboxylate linkage conveys a significant amount of the sandramycin selectivity for the 5'-CAT sequence which in turn is lost with the isoquinoline-1- or -3-carboxylate linkage even though high affinity binding with calf thymus DNA is maintained. Since the binding affinities of 21 and 22 are comparable to that of the monointercalator 24, it also suggests they may simply be acting as mono-intercalators. Although we were not able to accurately assess the DNA binding affinity of 5, 7, 18 or 19 because of their limited solubility and 9–10 because of their lack of fluorescence, the attempted measurements with 5 and 7 revealed they were substantially less effective than all agents in the series indicating that the quinoline nitrogen is important for high affinity binding.

The binding of sandramycin to five self-complementary deoxyoligonucleotides is summarized in FIG. 9. Using the fluorescence quenching to measure of binding and the curve fitting analysis of the data, sandramycin was found to bind to 5'-d(GCATGC)$_2$ more effectively than the remaining four deoxyoligonucleotides. In each case, Scatchard plots revealed a 1:1 stoichiometry for the high affinity binding event. This proved consistent with expectations based the bis-intercalation complex of sandramycin sandwiching the central two AT base-pairs of 5'-d(GCATGC)$_2$ defined by $^1$H NMR However, the distinctions were small and high affinity binding was observed with all five deoxyoligonucleotides. The two highest affinity sequences, 5'-(GCATGC)$_2$ and 5'-d(GCGCGC)$_2$, constitute repeating 5'-PuPy sequences such that each intercalation event occurs at a 5'-PyPu step. The highest affinity sequence of the pair constitutes the less stable duplex, contains the deeper and sterically most accessible minor groove central to the bis-intercalation site, and the ability to accept the two gly-NH/T C2 carbonyl H-bonds identified in NMR studies. The two lower affinity sequences involve intercalation at both a 5'-PyPy step and 5'-PuPu step if it occurs about the central two base-pairs. The intercalation event interrupting the 5'-PuPu step would seem energetically more costly while that interrupting the 5'-PyPy step would provide less energetic stabilization. The exception to this generalization is 5'-d(CGTACG)$_2$ which differs in the full length sequence from the other four and constitutes the reverse sequence of 5'-d(GCATGC)$_2$. This sequence has the weakest affinity of the five deoxyoligonucleotides despite the 5'-PuPy motif. The significance of these observations are not immediately interpretable but suggest that the surrounding sequence context and directional orientation can have a large impact on the observed binding affinity. The affinity of sandramycin for 5'-d(GCATGC)$_2$ relative to that of the remaining four deoxyoligonucleotides and the confirmed bis-intercalation about the central 5'-AT base-pairs provided the basis for its use to compare the analogs 2–22 (FIG. 8).

In Vitro Cytotoxic Activity.

The in vitro cytotoxic activities secured in initial studies provided the basis for examining the chromophore analogs detailed herein. These included the comparisons of luzopeptin A and sandramycin (1) with sandramycin bis-O-benzyl ether (2), 24 containing a single attached aromatic chromophore, and 23 lacking both aromatic chromophores (FIG. 11). Throughout the five cell lines, luzopeptin A and sandramycin exhibited comparable and exceptionally potent cytotoxic activity (6–0.02 nM IC$_{50}$). The bis benzyl ether 2 was typically 20–1000(less potent than 1. The agent 24 possessing a single chromophore was found to be 5000–10000(less potent than 1 and the cyclic decadepsipeptide 23 lacking both chromophores was approx 10$^5$(less potent than 1.

Figure 13:
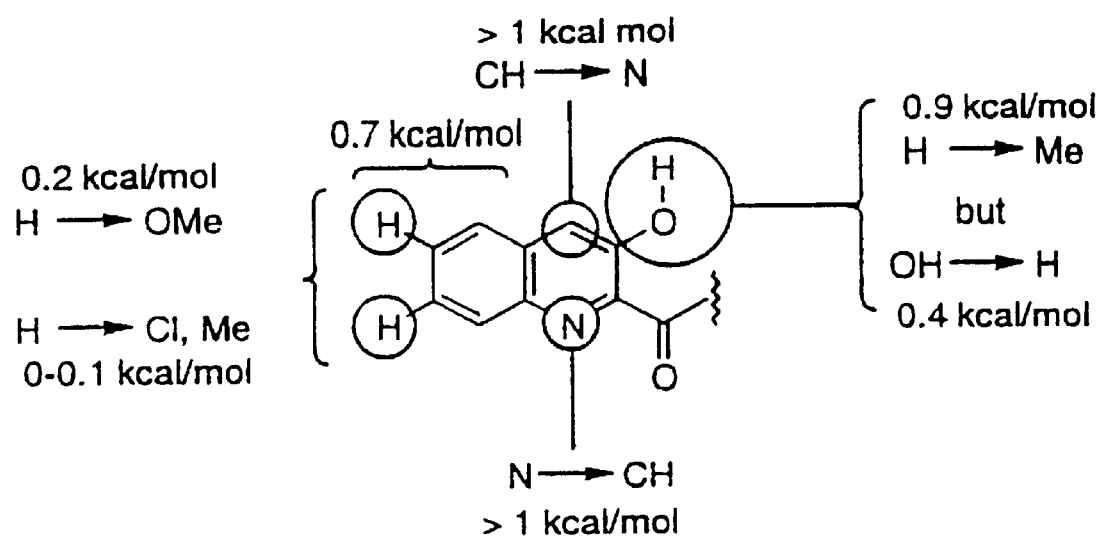
FIG. 13 illustrates trends in the comparison of luzopeptin A, sandramycin (1), and 2 with the chromophore analogs 3–22 in the single L1210 cell line.

FIG. 12 summarizes the comparison of luzopeptin A, sandramycin (1), and 2 with the chromophore analogs 3–22 in the single L1210 cell line. Several trends are clear in these comparisons (FIG. 13).

C3-Hydroxy Group. First, O-alkylation of the chromophore 3-hydroxy group typically reduced the cytotoxic potency 500–1000×. This is clear in the comparisons of both 2 and 3 with 1 (1000(×), 12 with 11 (400(×), 6 with 5 (>500(×), 9 with 8 (1000(×), and 20 with 19 (7(×). Significantly, even O-methylation of the sandramycin phenol (3) reduced the cytotoxic potency 1000× providing an agent that was equipotent with the benzyl ether 2. Despite this substantial reduction in potency by O-alkylation, removal of the phenol altogether had a much more modest effect. This is clear in the comparisons of 4 with 1 (10(×), 7 with 5 (2(×), and 13 with 11 (10(×). The exception is the comparison of 10 with 8 (1000(×) where the removal of the hydroxy group had a much larger effect. In addition, 18 was found to be more potent than 19 (300(×) even though the former agent lacks the hydroxyl group of 19. Although this effect may be unique to the quinoxaline chromophore, this was also observed with 4 in additional cell lines. Thus, the removal of the chromophore phenol has only a modest effect and, in some instances, results in more potent cytotoxic activity.

Quinoline Nitrogen (N1). The quinoline nitrogen proved especially important and its removal resulted in a substantial loss of cytotoxic potency ($10^4$–$10^3(\times)$). This is clear in the comparisons of 5 with 1 (10000($\times$)), 7 with 4 (2000($\times$)) and 6 with 2 (>5000($\times$)).

Extended Chromophore: Pyridine versus Quinoline. The quinoline versus pyridine comparisons embodied in 8 versus 1 (4000($\times$)), 9 versus 2 (4000($\times$)) and 10 versus 4 (4$\times 10^5$) clearly highlight the importance of the fused benzene ring ($10^4$–$10^5\times$).

Quinoline versus Isoquinoline. The analogous comparisons of 21 and 22 with 4 highlight the optimal quinoline-2-carboxylic acid linkage versus isoquinoline-3-carboxylic or isoquinoline-1-carboxylic acid linkage (100$\times$). However, both 21 and 22 were 4000(($10^3$–$10^4\times$) more effective than pyridine-2-carboxylic acid (10) illustrating that both are more effective than might be initially anticipated.

Quinoline Substitution. The incorporation of the luzopeptin chromophore into the sandramycin structure had no impact on the cytotoxic potency (11 versus 1, 2$\times$) and simply constitutes the introduction of a quinoline C6 methoxy substituent. An analogous comparison of 13 with 4 (2$\times$) and 12 with 2 (0.8$\times$) indicates that the relative lack of impact of the introduction of the C6 methoxy group is general and that it has little effect on the cytotoxic potency of the resulting agent. The addition comparisons of 14 (1$\times$) and 16 (0.5$\times$) with 1 illustrate that the analogous introductions of a C6 methyl group or C7 chlorine substituent maintain or perhaps enhance the cytotoxic potency, respectively. Clear from the comparisons, is the relatively small impact of C6 and C7 substituents regardless of their electronic and steric features, at least within the limited range examined. This series of agents including 11, 14, and 16 constitute exceptionally potent cytotoxic agents worthy of more detailed examination. Similarly, 4 and 13 possess a level of cytotoxic potency against L1210 and chemical properties (nonacidic) that make them alternative and attractive agents for further examination.

Quinoxaline versus Quinoline. Finally, 18 which incorporates the echinomycin chromophore and is analogous to that found in the recently isolated quinoxapeptins lacking only the C6 methoxy group proved to be approximately 100$\times$less potent than 1 and approximately 10$\times$ less potent than 4 and 13.

Figure 16:
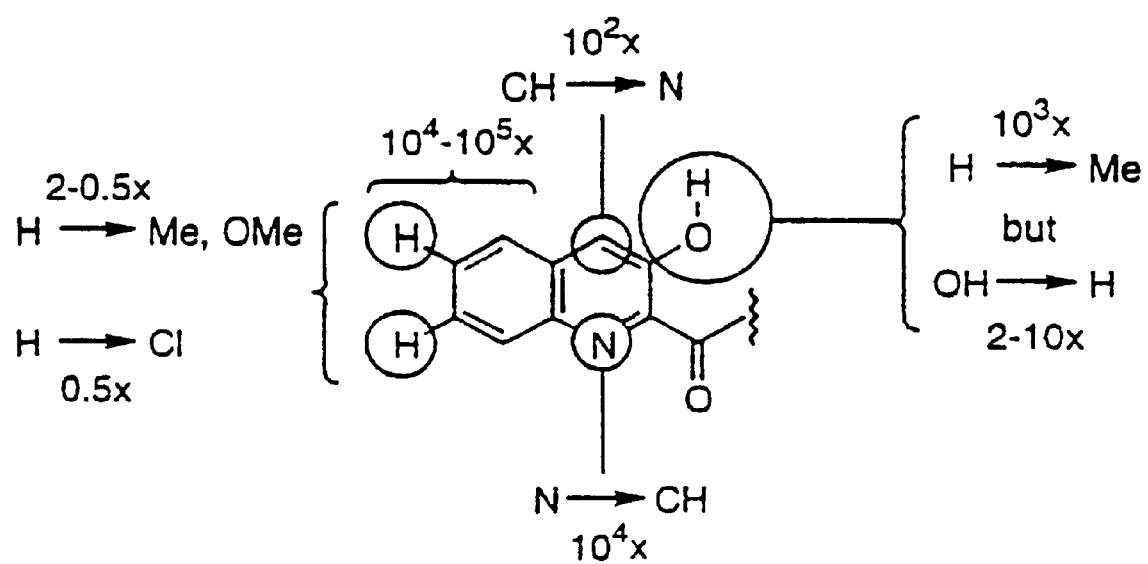
FIG. 16 illustrates further trends in the comparison of luzopeptin A, sandramycin (1), and 2 with the chromophore analogs 3–22 in the single L1210 cell line; wherein removal of the C3 hydroxy group has only a small effect (2–10×) while its conversion to a methyl or benzyl ether has a pronounced diminishing effect (1000×).
Figure 18:
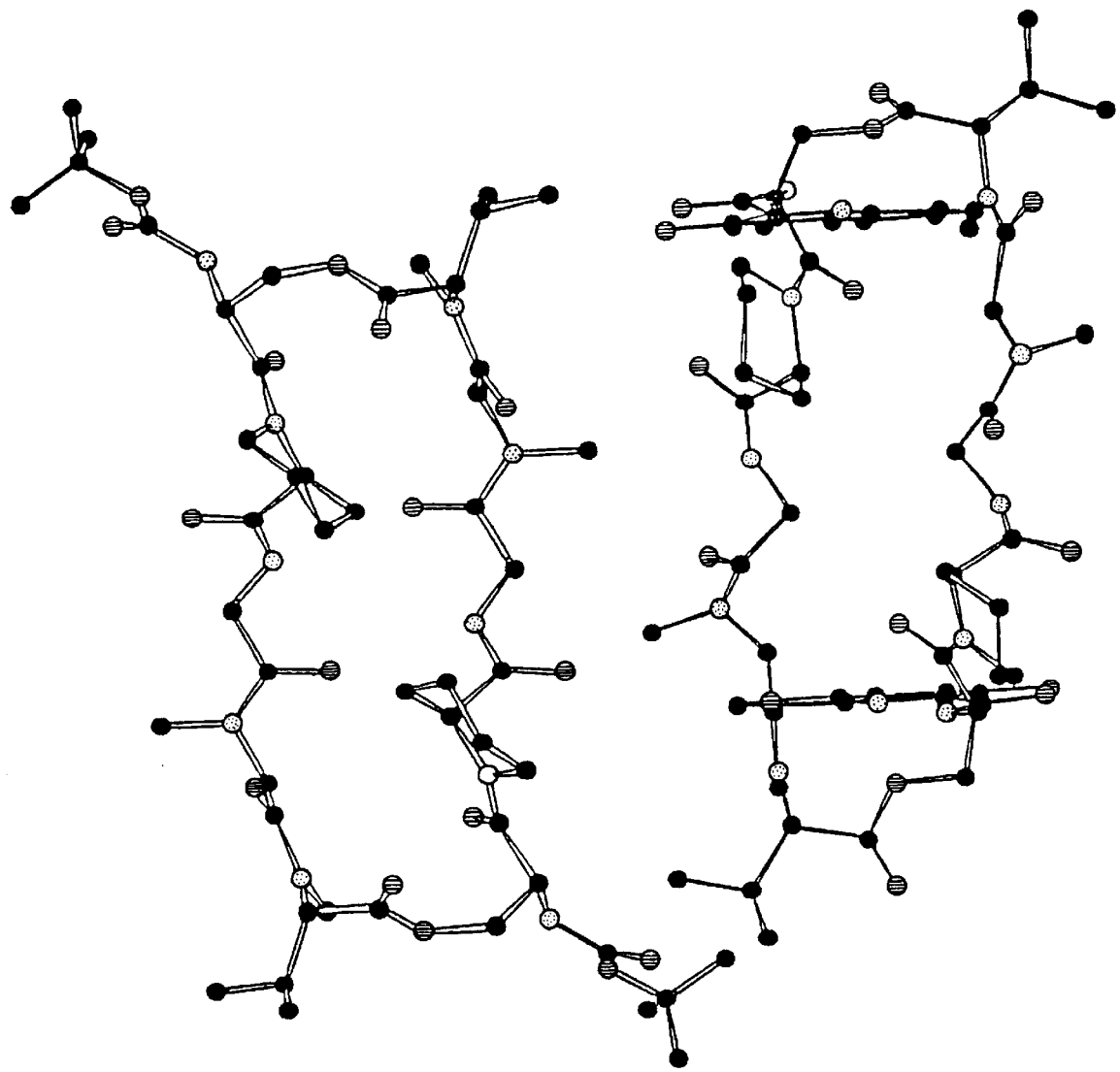
FIG. 18 shows a chemdraw 3D representation illustrating the differences in amide conformation between the X-ray structure of 23 (left) and the minimized structure of the 5'-GCATGC)$_2$ bound conformation of sandramycin (1) based on 2D $^1$H NMR solution studies (right).
Figure 22:
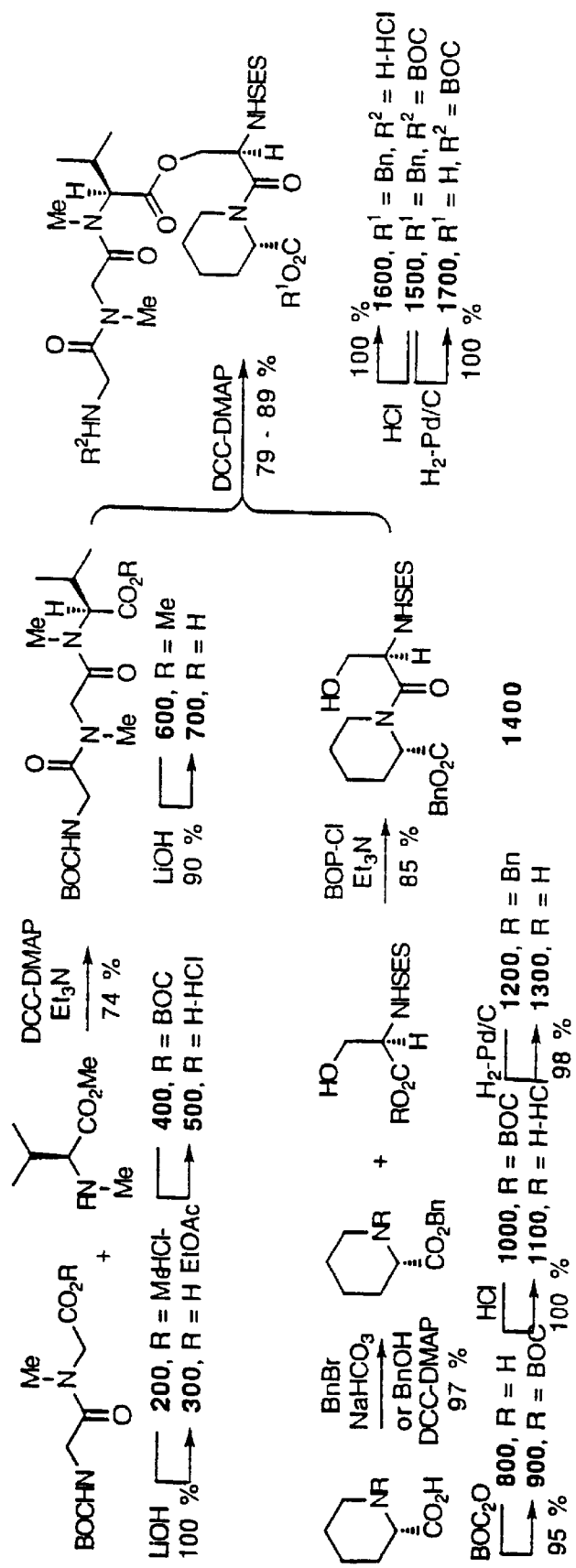
FIG. 22 shows the synthesis of intermediate compounds 700 and 1400–1700.
Figure 23:
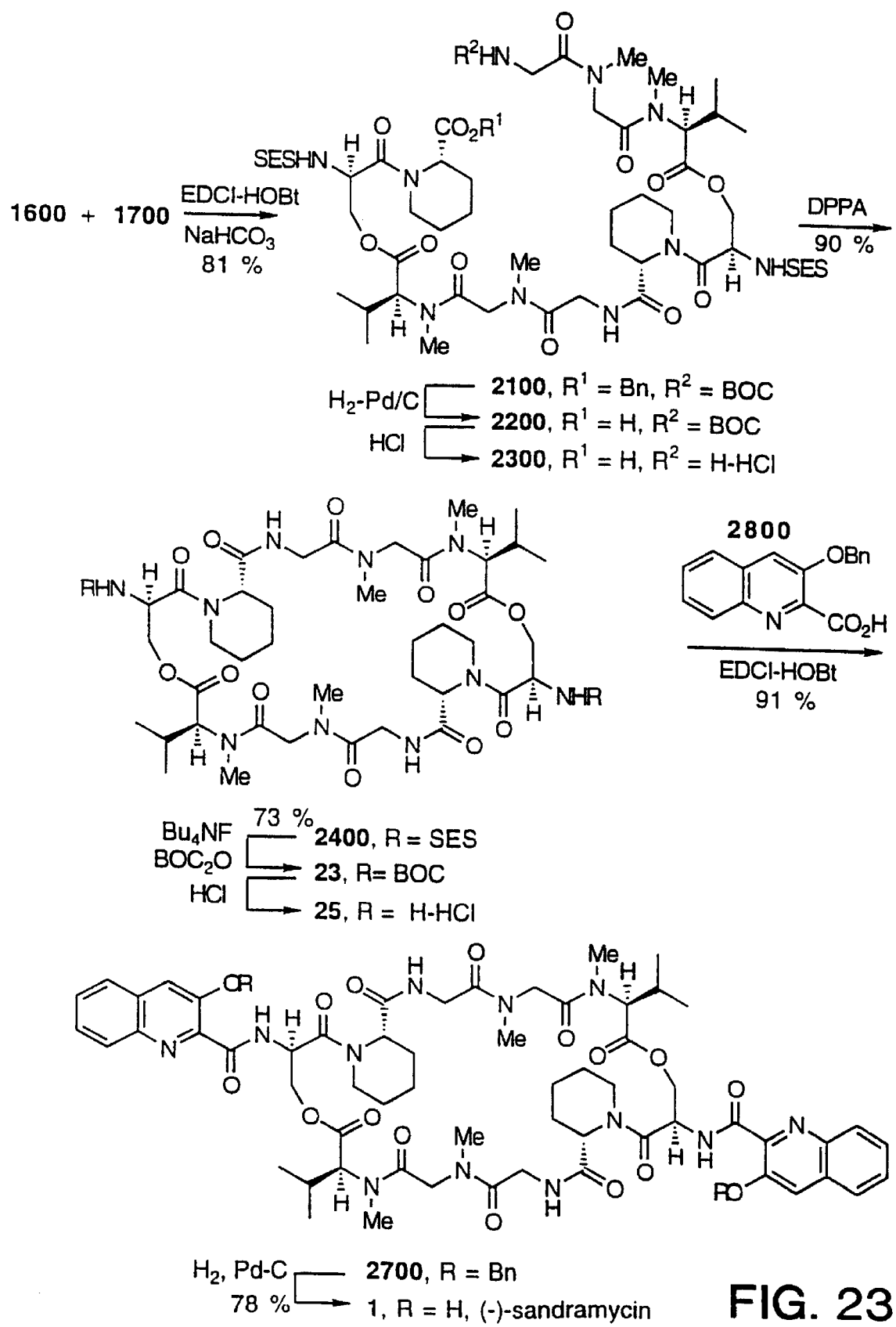
FIG. 23 shows the synthesis of the natural product, (−)-sandramycin (1) and precursor intermediates 23 and 25.
Figure 24:
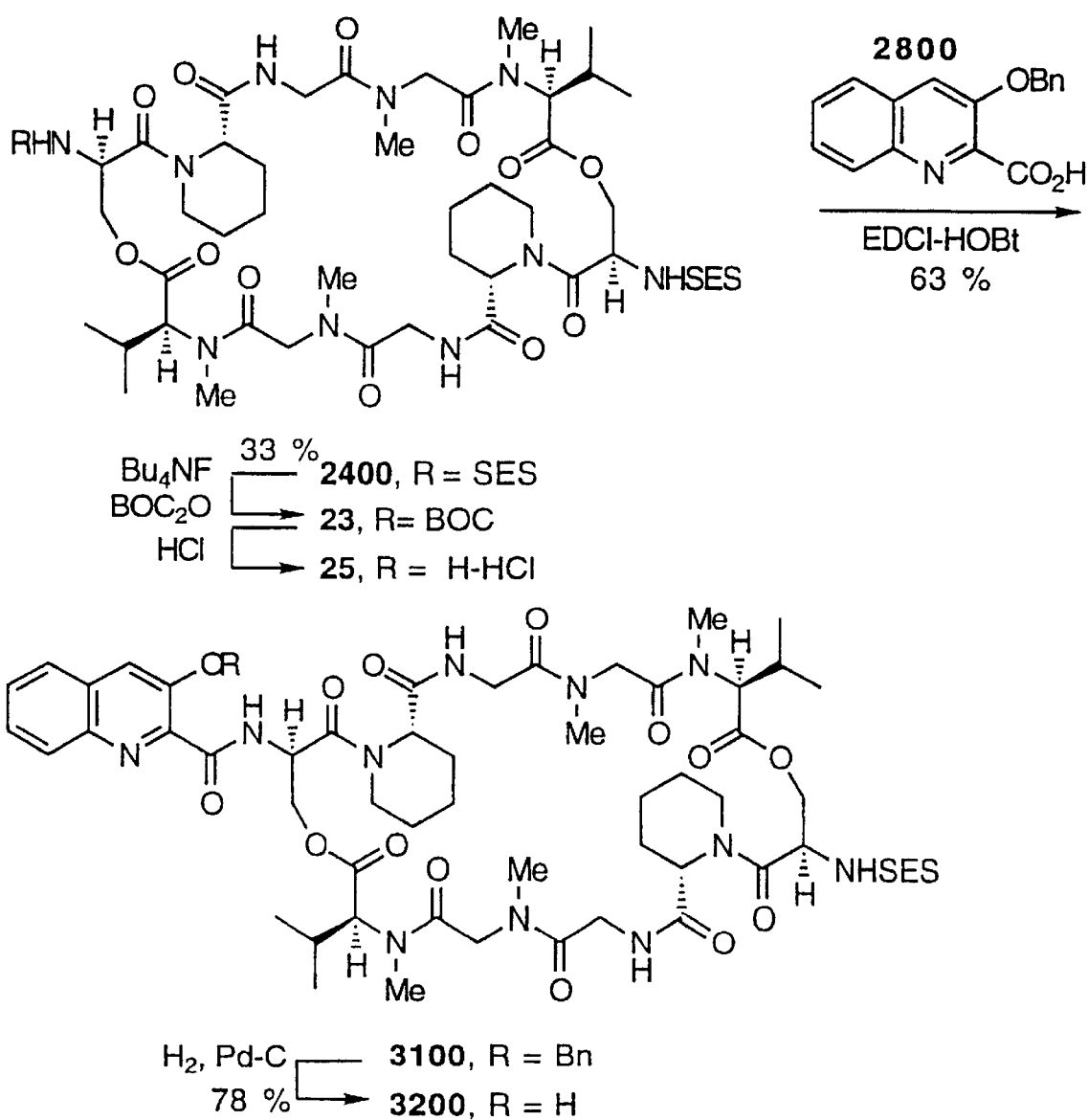
FIG. 24 illustrates the synthesis of compound 3200.

Thus, sandramycin was found to be equipotent to luzopeptin A, the most potent member of the luzopeptins. Removal of the C3 hydroxy group has only a small effect (2–10$\times$) while its conversion to a methyl or benzyl ether has a pronounced diminishing effect (1000$\times$), FIG. 16. One of the largest effects observed was removal of the chromophore nitrogen which reduced the cytotoxic potency 10000$\times$. Substitution of a pyridine versus quinoline chromophore reduced the potency by approximately 1000$\times$ and the use of the isomeric 1- or 3-isoquinoline chromophore reduced the potency by approximately 100$\times$ relative to 2-quinoline. Interestingly, incorporation of the echinomycin chromophore provided agents 100$\times$ less potent while incorporation of the luzopeptin chromophore provided agents equipotent with sandramycin. Importantly, the nature of the C6 or C7 chromophore substituents had essentially no effect on the cytotoxic properties of the agents.

In order to establish the role and subtle importance of the key substituents more carefully, a detailed comparison of luzopeptin A, sandramycin (1) and 4 was conducted (FIG. 14). Several interesting observations were made in these additional comparisons. In the leukemia cell lines, typically it was found that luzopeptin A and sandramycin were equipotent and more potent than 4 with one notable exception where 4 was found to be exceptionally potent (HL-60). In the remaining cell lines, 4 proved to be equipotent or more potent than either luzopeptin A and sandramycin: carcinomas and adenocarcinomas, 4>luzopeptin A>sandramycin (1); melanomas, 4=luzopeptin A>sandramycin (1). Thus, the removal of the acidic phenol from the chromophore of sandramycin providing 4 afforded an agent that typically exhibits more potent cytotoxic activity in a range of cell lines. In many instances, the cytotoxic potency of 4 is exceptional and it was found to typically exhibit $IC_{50}$ values in the range of 200–1 pM. This places it among the most potent agents defined to date.

Inhibition of HIV-1 Reverse Transcriptase.

Sandramycin and its analogs were also examined for their ability to inhibit HIV-1 reverse transcriptase analogous to the quinoxapeptins and luzopeptin A. In these prior studies, quinoxapeptin A and luzopeptin A exhibited comparable inhibitory potency while quinoxapeptin B was approximately 2$\times$ less potent. All three were several orders of magnitude more potent (5000$\times$) than the most potent natural products defined in a screen of >150 candidate natural products. Moreover, quinoxapeptin A was found to be nearly equally effective (1–3$\times$) against two single mutant and one double mutant of HIV-1 reverse transcriptase by a mechanism that involves template-primer binding and noncompetitive enzyme inhibition. Thus, their use in combination with non-nucleoside inhibitors subject to mutation resistance may prove especially important.

The assay was performed following a slight modification of an established procedure and the results are summarized in FIG. 15. Sandramycin proved slightly more effective than luzopeptin A and both exhibit $IC_{50}$ values of 130–190 nM. For luzopeptin A, this is 20–30(higher than values reported elsewhere (7 nM) and may be attributed to differences in the assay. A similar potency was observed with 11 which incorporates the luzopeptin chromophore into the sandramycin structure. Comparable but slightly less potent inhibition was observed with 4, 13, 14, 16, and 18. Within this potent series, the agents possessing a C3 phenol were found to be 3–6$\times$ more potent than the corresponding agents lacking the phenol (C3-H). Interestingly, the analog 18, which incorporates the echinomycin chromophore, and 4 proved equipotent and only 3$\times$ less potent than sandramycin itself. O-Alkylation of the C3 phenol with 3 and 17 resulted in a marked reduction in the inhibitory potency and the extent of the reduction approx. 10$\times$ versus >500$\times$ correlates with the size of the substituent and its relative effect on DNA binding affinity. The alternative analogs 5, 7, 8, 10, 21, and 22 were much less effective and follow affinity trends established in the DNA binding studies. These results are summarized in FIG. 16. Because of their differential cytotoxicity (18<1, 150$\times$; 3<1, 1000$\times$) but their maintained ability to inhibit HIV-1 reverse transcriptase, both 3 and 18 merit further examination.

EXAMPLE 2

An Exceptionally Potent Analog of Sandramycin

The preparation and preliminary evaluation of 4, an analog of sandramycin, are highlighted in this example. Although 4 was typically 4–10$\times$ less potent than sandramycin against leukemia cell lines, it was found to be 1–10,000$\times$ more potent against melanomas, carcinomas, and adenocarcinomas exhibiting typical $IC_{50}$ values of 200–1 pM and placing it among the most potent agents identified to date.

Preparation of 4.

The synthesis of 4 is detailed in example 1 and required N-BOC deprotection of 23 ($[\alpha]^{23}D$ −53 (c 1.5, CHCl$_3$), 3 M HCl-EtOAc, 25° C., 30 min) and coupling of the resulting bis amine with quinoline-2-carboxylic acid (4 equiv of EDCI, 6.0 equiv of HOBt, 10 equiv of NaHCO3, DMF, 25° C., 48–72 h, 76–94%), FIG. 20.

In Vitro Cytotoxic Activity.

In preceding studies, sandramycin (1) and luzopeptin A were established to exhibit comparable cytotoxic potencies, luzopeptin A was determined to be 100–300× more potent than echinomycin, and the potency of the luzopeptins smoothly declined in the series A>B>C. Removal of one chromophore from sandramycin reduced the cytotoxic potency 500–1000× and 23 in which both chromophores of sandramycin were removed was inactive. These latter studies established the essential role of the chromophores for observation of the potent cytotoxic activity. The examination of 4 (FIG. 21) further established this important and remarkable role. Removing the chromophore acidic phenol from sandramycin provided an exceptionally potent cytotoxic agent. In the leukemia cell lines, it was found that sandramycin was typically 4–10× more potent than 4 with the notable exception of HL-60 where 4 was unusually potent. In the remaining cell lines, 4 was found to be equipotent or more potent than sandramycin (1–10,000×). Thus, the removal of the acidic phenol from the chromophore of sandramycin provided an agent that is substantially more potent than the natural product in a range of tumor cell lines. This cytotoxic potency is exceptional and typically 4 exhibits IC$_{50}$ values in the 200–1 pM range placing it among the most potent agents defined to date.

Although many explanations may account for such observations, it is not due to discernible differences in the relative DNA binding affinity or selectivity of 4 and sandramycin. Rather, it may likely be due to removal of the acidic phenol providing better target delivery without adversely affecting the DNA binding properties of the agent.

EXAMPLE 3

Topical Formulations of Inhibitor 4 and Others for the Treatment of Melanomas

For treament, the candidate inhibitor (eg. inhibitor 4) is administered topically. For topical administration to the skin, the compound is preferably providied in association with a pharmaceutically/dermatologically acceptable carrier. The inhibitor is admixed with the dermatologically acceptable carrier in the desired concentration. Preferred pharmaceutically/dermatologically acceptable carriers include but are not restricted to: 1) a hydrophobic ointment base consisting of 95% mineral oil and 5% polyethylene (or any percent combination thereof); 2) an emollient cream consisting of white petrolatum USP, purified water USP, isopropyl myristate NF, lanolin alcohols NF, mineral oil USP, cetostearyl alcohol NF, aluminum starate and magnesium stearate; and 3) white petrolatum USP.

Liposomes can also be used as acceptable carriers. Liposomes, which are artificial phospholipid vesicles, have been successfully used for delivery of different low-molecular-weight water-soluble and oil-soluble compounds into different cells. See, for example, G. Gregoriadis, *Trends in Biotechnology*, 3:235–241 (1985) and K. H. Schmidt, ed., Liposomes as drug carriers, Stuttgart: George Thieme Verlag (1986). Liposomes are typically formed by mixing dry phospholipids with aqueous solutions giving rise to bilayers of phospholipid molecules which arrange themselves spontaneously to form close multilayered spherules. As they form, the liposomes entrap liquid and any soluble solutes that are present. A large number of substances that do not interfere with the formation of the liposomes can be incorporated, regardless of solubility, electrical charge, size and other structural characteristics. These characteristics may, however, have adverse affects in some environments limiting the use of liposomes.

For treament, the candidate inhibitor is administered topically, or the like routes with or without liposomic formulations. For topical administration to the skin, the compound is preferably providied in association with an dermatologically acceptable carrier. Other dermatological modalities are provided in U.S. Pat. Nos. 5,401,880, 5,422, 376, 5,519,054, 5,578,578 and 5,628,801, the disclosures of which are hereby incorporated by reference. In the case of using liposomic formulations, the analog inhibitor of interest (eg. compound 4) is first encapsulated inside the liposome using standard methods and then suspended in a medium as described below and applied topically to the skin.

Thus, the compounds of this invention, including compound 4, may be employed in a conventional manner for the treatment of melanoma. Such methods of treatment, their dosage levels and requirements may be selected by those of ordinary skill in the art from available methods and techniques and as stated herein. For example, a compound of this invention may be combined with an acceptable pharmaceutical carrier for a time period and in an amount effective to affect melanoma cell growth in a subject.

Alternatively, the inhibitors of this invention may be used in compositions and methods for treating or protecting a subject against melanoma over extended periods of time. An inhibitor may be employed in such compositions either alone or together with other inhibitors of this invention in a manner consistent with the conventional utilization of ICE inhibitors in pharmaceutical compositions.

Pharmaceutical compositions of this invention comprise any of the compounds of the present invention, and pharmaceutically acceptable salts thereof, with any pharmaceutically acceptable carrier, adjuvant or vehicle. As used herein, the terms "pharmaceutically acceptable", "opthalmalogically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as burning, irritation, shock, nausea, dizziness, gastric upset and the like. The preparation of a pharmacological composition that contains active ingredients dissolved or dispersed therein is well understood in the art and need not be limited based on formulation.

Pharmaceutically/dermatologically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride-mixtures of saturated vegetable fatty acids, water, salts or electrolytes, such as protamine sulfate, disodium hydrogen phosphate, potassium hydrogen phosphate, sodium chloride, zinc salts,colloidal silica, magnesium trisilicate, polyvinyl pyrrolidone, cellulose-based substances, polyethylene glycol, sodium carboxy-methylcellulose, polyacrylates, waxes, polyethylene-polyoxypropylene-block polymers, polyethylene glycol and wool fat.

Synthetic Protocals

General: $^1$HNMR spectra were recorded on a Bruker AMX-500 NMR spectrometer. Mass spectra were recorded on an API III PE Sciex triple-quadrupole mass spectrometer. All reactions were carried out under an argon atmosphere with dry, freshly distilled solvents under anhydrous conditions, unless otherwise noted. Tetrahydrofuran (THF), toluene and ethyl ether (ether) were distilled from sodium-benzophenone, and methylene chloride (Methylene chloride), from calcium hydride. Anhydrous solvents were also obtained by passing them through commercially available alumina column. Yields refer to chromatographically and spectroscopically ($^1$H NMR) homogeneous materials, unless otherwise stated. Reagents were purchased at highest commercial quality and used without further purification unless otherwise stated. Reactions were monitored by thin layer chromatography carried out on 0.25 mm E. Merck silica gel plates (60F-254) using UV light as visualizing agent and 7% ethanolic phosphomolybdic acid or p-anisaldehyde solution and heat as developing agents. E. Merck silica gel (60, particle size 0.040–0.063 mm) was used for flash column chromatography. Preparative thin-layer chromatography (PTLC) separations were carried out on 0.25, 0.50 or 1 mm E. Merck silica gel plates (60F-254). NMR spectra were recorded on Brucker AMX-600 or AMX-500 instruments and calibrated using residual undeuterated solvent as an internal reference. The following abbreviations were used to explain the multiplicities: s=singlet, d=doublet, t=triplet, q=quartet, m=multiplet, b=broad. IR spectra were recorded on a Perkin-Elmer 1600 series FT-IR spectrometer. Optical rotations were recorded on a Perkin-Elmer 241 polarimeter. High resolution mass spectra (HRMS) were recorded on a VG ZAB-ZSE mass spectrometer under fast atom bombardment (FAB) conditions with NBA as the matrix. Melting points (mp) are uncorrected and were recorded on a Thomas Hoover Unimelt capillary melting point apparatus.

General Procedure for the Coupling of Chromophore

Carboxylic Acids with 23: (N-(3-Benzyloxy-6-methoxy-quinolinyl-2-carbonyl)-D-Ser-Pip-Gly-Sar-NMe-Val)$_2$ (Serine Hydroxyl) Dilactone (12) as Illustrated in FIG. 4.

A solution 23 (18.8 mg, 0.017 mmol; Boger et al. *J. Am. Chem. Soc.* 1996, 118, 1629; Boger et al. *J. Am. Chem. Soc.* 1993, 115, 11624; For a preliminary disclosure of 4: see Boger et al. *Bioorg. Med. Chem. Lett.* 1997, 7, 919) in 3 M HCl-EtOAc (1 mL) at 25° C. was stirred for 30 min. The solvent was removed in vacuo to afford the hydrochloride salt 25 (17.1 mg, 16.6 mg theoretical, 100%) as a white powder which was used directly in next reaction.

A solution of the hydrochloride salt 25 (16.6 mg, 0.017 mmol) and 3-benzyloxy-6-methoxyquinoline-2-carboxylic acid (Boger et al. *J. Org. Chem.* 1995, 60, 7369) (21.5 mg, 0.07 mmol, 4.0 equiv) in DMF (2 mL) was treated sequentially with NaHCO$_3$ (14.6 mg, 0.17 mmol, 10.0 equiv), HOBt (14.1 mg, 0.10 mmol, 6.0 equiv), and EDCI (13.4 mg, 0.07 mmol, 4.0 eguiv) and the reaction mixture was stirred at 25° C. for 72 h. The reaction mixture was diluted with EtOAc (20 mL) and washed with H$_2$O (10 mL), saturated aqueous NaCl (10 mL), dried (Na$_2$SO$_4$), filtered, and concentrated in vacuo. Flash chromatography (SiO$_2$, 1 (16 cm, 0–5% EtOH—CH$_2$Cl$_2$ gradient) afforded 12 (20.6 mg, 25.5 mg theoretical, 81%) as a white powder: R$_f$=0.58 (20% CH$_3$CN-EtOAC); [α]$^{23}$D –113 (c 0.2, CHCl$_3$); $^1$H NMR (CDCl$_3$, 400 MHz) 9.04 (d, 2H, J=6.3 Hz, Ser-NH), 8.48 (d, 2H, J=4.4 Hz, Gly-NH), 7.80 (d, 2H, J=9.2 Hz, C8'—H), 7.55 (d, 4H, J=7.3 Hz, phenyl C2 and C6—H), 7.49 (s, 2H, C4'—H), 7.39 (t, 4H, J=7.3 Hz, phenyl C3 and C5—H), 7.29 (t, 2H, J=7.3 Hz, phenyl C4—H), 7.19 (dd, 2H, J=2.7, 9.2 Hz, C7'—H), 6.92 (d, 2H, J=2.7 Hz, C5'—H), 5.46 (d, 2H, J=4.1 Hz, Pip-—CH), 5.44 (d, 2H, J=16.6 Hz, Sar-—CH), 5.31 (m, 6H, PhCH$_2$ and Ser-—CH), 4.85 (dd, 2H, J=1.4, 11.5 Hz, Ser-—CH), 4.82 (d, 2H, J=11 Hz, Val-—CH), 4.57 (dd, 2H, J=2.5, 11.5 Hz, Ser-—CH), 4.42 (dd, 2H, J=5.7, 18.2 Hz, Gly-—CH), 4.03 (d, 2H, J=18.2 Hz, Gly-—CH), 3.99 (m, 2H, Pip-G-CH), 3.90 (s, 6H, OCH$_3$), 3.76 (d, 2H, J=13.2 Hz, Pip-G-CH), 3.46 (d, 2H, J=16.6 Hz, Sar-—CH), 3.07 (s, 6H, Val-NCH$_3$), 2.91 (s, 6H, Sar-NCH$_3$), 2.06 (d split septet, 2H, J=6.5, 11.0 Hz, Val-—CH), 1.80–1.45 (m, 12H, Pip-(CH$_2$)$_3$), 0.94 (d, 6H, J=6.5 Hz, Val-—CH$_3$), 0.80 (d, 6H, J=6.5 Hz, Val-—CH$_3$); $^{13}$C NMR (CDCl$_3$, 100 MHz) 172.7, 169.2, 169.1, 167.7, 167.1, 163.5, 159.4, 152.3, 139.5, 137.7, 136.1, 131.8, 131.0, 128.7, 127.9, 126.8, 120.7, 116.3, 103.6, 70.8, 62.9, 62.3, 55.6, 52.4, 50.7, 49.3, 43.8, 41.9, 34.9, 30.4, 28.7, 26.5, 24.8, 20.2, 19.4, 19.0; IR (KBr)$_{max}$ 3487, 3327, 2936, 1742, 1672, 1638, 1492, 1417, 1263, 1229, 1136, 1019, 832, 734 cm$^{-1}$; FABHRMS (NBA) m/z 1461.6770 (M+H$^+$, C$_{76}$H$_{92}$N$_{12}$O$_{18}$ requires 1461.6731).

General Procedure for Bis O-Benzyl Ether Deprotection: (N-(3-Hydroxy-6-Methoxy-quinolinyl-3-carbonyl)-D-Ser-Pip-Gly-Sar-NMe-Val)$_2$ (Serine Hydroxyl) Dilactone (11) as Illustrated in FIG. 4.

A sample of 10% Pd—C (3 mg) was added to a solution of 12 (14.3 mg, 0.0098 mmol) in EtOAc (4 mL) and the black suspension was stirred at 25° C. under an atmosphere of H$_2$ (1 atm) for 14 h. The catalyst was removed by filtration through Celite and the filtrate was concentrated in vacuo. Flash chromatography (SiO$_2$, 1 (16 cm, EtOAc eluent) afforded 11 (10.2 mg, 12.5 mg theoretical, 82%) as a white powder: R$_f$=0.31 (EtOAc); [α]$^{23}$D –118 (c 0.28, CHCl$_3$); $^1$H NMR (CDCl$_3$, 400 MHz) 11.76 (s, 2H, OH), 9.44 (d, 2H, J=5.0 Hz, Ser-NH), 8.52 (br s, 2H, Gly-NH), 7.68 (d, 2H, J=8.5 Hz, C7—H), 7.48 (s, 2H, C4—H), 7.14 (d, 2H, J=8.5 Hz, C8—H), 6.90 (d, 2H, J=2.7 Hz, C5—H), 5.56 (d, 2H, J=5.9 Hz, Pip-—CH), 5.53 (d, 2H, J=16.5 Hz, Sar-—CH), 5.25 (d, 2H, J=5.0 Hz, Ser-—CH), 4.96 (d, 2H, J=11.7 Hz, Ser-—CH), 4.87 (d, 2H, J=11.0 Hz, Val-—CH), 4.43 (d, 4H, J=11.7 Hz, Ser-—CH and Gly-—CH), 4.05 (m, 4H, Gly-—CH and Pip-G-CH), 3.92 (s, 6H, OCH$_3$), 3.74 (m, 2H, Pip-G-CH), 3.54 (d, 2H, J=16.5 Hz, Sar-—CH), 3.10 (s, 6H, Val-NCH$_3$), 2.93 (s, 6H, Sar-NCH$_3$), 2.04 (d split septet, 2H, J=11.0, 6.5 Hz, Val-—CH), 1.80–1.50 (m, 12H, Pip-(CH$_2$)$_3$), 0.93 (d, 6H, J=6.5 Hz, Val-—CH$_3$), 0.79 (d, 6H, J=6.5 Hz, Val-—CH$_3$); $^{13}$C NMR (CDCl$_3$, 100 MHz) 172.6, 169.4, 169.2, 168.0, 167.7, 166.3, 159.5, 154.4, 137.8, 133.4, 132.1, 130.9, 121.0, 118.9, 103.0, 62.4, 62.0, 55.6, 52.5, 50.5, 49.3, 43.9, 41.9, 34.9, 30.3, 28.7, 26.3, 24.9, 20.2, 19.4, 18.7; IR (KBr)$_{max}$ 3330, 2936, 1745, 1668, 1640 cm$^{-1}$; FABHRMS (NBA) m/z 1281.5890 (M+H$^+$, C$_{62}$H$_{80}$N$_{12}$O$_{18}$ requires 1281.5792).

Data for (N-(3-Methoxy-quinolinyl-2-carbonyl)-D-ser-Pip-Gly-Sar-NMe-Val)$_2$ (Serine Hydroxyl) Dilactone (3) Shown in FIG. 2:

Synthesized according to the general procedure outline above using 23 and 3-benzyloxy-6-methoxyquinoline-2-carboxylic acid except substituting 3-methoxyquinoline-2-carboxylic acid for 3-benzyloxy-6-methoxyquinoline-2-carboxylic acid: 0.0093 mmol scale; flash chromatography (SiO$_2$, 1 (16 cm, 0–5% EtOH—CH$_2$Cl$_2$ gradient) afforded 3 (9.7 mg, 11.6 mg theoretical, 84%) as white powder: R$_f$=0.49 (5% EtOH—CH$_2$Cl$_2$); [α]$^{23}$D –136 (c 0.2, CHCl$_3$); $^1$H NMR (CDCl$_3$, 400 MHz) 9.02 (d, 2H, J=6.2 Hz, Ser-NH), 8.48 (d, 2H, J=4.2 Hz, Gly-NH), 7.96 (m, 2H, C5'—H), 7.74 (m, 2H, C8'—H), 7.57 (s, 2H, C4'—H), 7.56 (m, 4H, C6' and C7'—H), 5.46 (d, 2H, J=16.5 Hz, Sar-—CH), 5.45 (d, 2H, J=7.3 Hz, Pip-—CH), 5.31 (d, 2H, J=6.2 Hz, Ser-—CH), 4.86 (dd, 2H, J=1.8, 12.0 Hz, Ser-—CH), 4.83

(d, 2H, J=11.0 Hz, Val—CH), 4.57 (dd, 2H, J=2.8, 12.0 Hz, Ser—CH), 4.42 (dd, 2H, J=5.7, 18.3 Hz, Gly—CH), 4.06 (m, 2H, Gly—CH), 4.03 (s, 6H, OCH$_3$), 4.01 (m, 2H, Pip-G-CH), 3.76 (d, 2H, J=14.0 Hz, Pip-G-CH), 3.49 (d, 2H, J=16.5 Hz, Sar—CH), 3.09 (s, 6H, Val-NCH$_3$), 2.92 (s, 6H, Sar-NCH$_3$), 2.07 (d split septet, 2H, J=6.5, 11.0 Hz, Val—CH), 1.80–1.45 (m, 12H, Pip-(CH$_2$)$_3$), 0.95 (d, 6H, J=6.5 Hz, Val—CH$_3$), 0.81 (d, 6H, J=6.5 Hz, Val—CH$_3$); $^{13}$C NMR (CDCl$_3$, 100 MHz) 172.6, 169.3, 169.2, 167.7, 167.0, 163.5, 152.9, 141.9, 141.5, 130.3, 129.6, 128.5, 127.4, 126.3, 115.1, 62.8, 62.1, 56.1, 52.5, 50.8, 49.3, 43.9, 41.9, 34.9, 30.4, 28.7, 26.5, 24.8, 20.2, 19.4, 19.0; IR (KBr)$_{max}$ 3324, 2939, 1741, 1672, 1636, 1491, 1467, 1417, 1344, 1286, 1201, 1137, 1097, 1013 cm$^{-1}$; FABHRMS (NBA) m/z 1249.5961 (M+H$^+$, C$_{62}$H$_{80}$N$_{12}$O$_{16}$ requires 1249.5894).

Data for (N-(Quinol-inyl-2-carbonyl)-D-Ser-Pip-Gly-Sar-NMe-Val)$_2$ (Serine Hydroxyl) Dilactone (4) Shown in FIG. 2:

Synthesized according to the general procedure outline above using 23 and 3-benzyloxy-6-methoxyquinoline-2-carboxylic acid except substituting quinoline-2-carboxylic acid for 3-benzyloxy-6-methoxyquinoline-2-carboxylic acid: 0.0056 mmol scale; flash chromatography (SiO$_2$, 1 (16 cm, 0–10% EtOH—CH$_2$Cl$_2$ gradient) afforded 4 (5.2 mg, 6.7 mg theoretical, 78%) as white powder: R$_f$=0.38 (10% CH$_3$CN-EtOAc); [α]$^{23}$D –139 (c 0.3, CHCl$_3$); $^1$H NMR (CDCl$_3$, 400 MHz) 9.42 (d, 2H, J=6.3 Hz, Ser-NH), 8.53 (d, 2H, J=4.6 Hz, Gly-NH), 8.29 (s, 4H, C3' and C4'—H), 7.97 (d, 2H, J=8.3 Hz, C5'—H), 7.87 (dd, 2H, J=1.0, 8.3 Hz, C8'—H), 7.72 (ddd, J=1.4, 7.1, 8.3 Hz, C7'—H), 7.60 (ddd, 2H, J=1.0, 7.1, 8.3 Hz, C6'—H), 5.56 (d, 2H, J=7.1 Hz, Pip—CH), 5.55 (d, 2H, J=16.3 Hz, Sar—CH), 5.31 (d, 2H, J=6.3 Hz, Ser—CH), 4.97 (dd, 2H, J=1.5, 12.0 Hz, Ser—CH), 4.86 (d, 2H, J=11.0 Hz, Val—CH), 4.46 (dd, 2H, J=2.9, 12.0 Hz, Ser—CH), 4.43 (dd, 2H, J=4.5, 12.8 Hz, Gly—CH), 4.08 (m, 2H, Pip-G-CH), 4.04 (d, 2H, J=16.8 Hz, Gly—CH), 3.76 (d, 2H, J=13.3 Hz, Pip-G-CH), 3.55 (d, 2H, J=16.3 Hz, Sar—CH), 3.14 (s, 6H, Val-NCH$_3$), 2.93 (s, 6H, Sar-NCH$_3$), 2.03 (d split septet, 2H, J=6.6, 11.0 Hz, Val—CH), 1.82–1.52 (m, 12H, Pip-(CH$_2$)$_3$), 0.92 (d, 6H, J=6.6 Hz, Val—CH$_3$), 0.78 (d, 6H, J=6.5 Hz, Val—CH$_3$); $^{13}$C NMR (CDCl$_3$, 100 MHz) 172.7, 169.3, 169.1, 167.7, 166.9, 163.8, 149.4, 146.6, 137.3, 129.9, 129.7, 129.4, 128.7, 127.8, 118.8, 62.7, 62.0, 52.4, 50.8, 49.3, 43.8, 41.9, 34.9, 30.4, 28.8, 26.3, 24.9, 20.2, 19.4, 18.8; IR (KBr)$_{max}$ 3328, 2939, 1743, 1669, 1636, 1497, 1425, 1286, 1136, 1015, 847, 777 cm$^{-1}$; FABHRMS (NBA) m/z 1189.5685 (M+H$^+$, C$_{60}$H$_{76}$N$_{12}$O$_{14}$ requires 1189.5682).

Data for (N-(3-Benzyl-oxynaphthyl-2-carbonyl)-D-Ser-Pip-Gly-Sar-NMe-Val)$_2$ (Serine Hydroxyl) Dilactone (6) Shown in FIG. 2:

Synthesized according to the general procedure outline above using 23 and 3-benzyloxy-6-methoxyquinoline-2-carboxylic acid except substituting 3-hydroxy-3-benzyloxynaphthalene-2-carboxylic acid for 3-benzyloxy-6-methoxyquinoline-2-carboxylic acid: 0.015 mmol scale; flash chromatography (SiO$_2$, 1 (16 cm, 0–5% EtOH—CH$_2$Cl$_2$ gradient) afforded 6 (18.5 mg, 21.7 mg theoretical, 85%) as white powder: R$_f$=0.36 (20% CH$_3$CN-EtOAc); [α]$^{23}$D –64 (c 0.6, CHCl$_3$); $^1$H NMR (CDCl$_3$, 400 MHz) 9.32 (d, 2H, J=5.8 Hz, Ser-NH), 8.76 (s, 2H, C1'—H), 8.47 (d, 2H, J=3.8 Hz, Gly-NH), 7.88 (d, 2H, J=8.1 Hz, C5'—H), 7.62 (d, 2H, J=8.1 Hz, C8'—H), 7.50–7.25 (m, 14H, C6', C7', and phenyl CH), 7.19 (s, 2H, C4'—H), 5.48–5.35 (m, 8H, Pip—CH, Ser—CH, and PhCH$_2$), 5.24 (d, 2H, J=16.6 Hz, Sar—CH), 4.75 (d, 2H, J=11.0 Hz, Val—CH), 4.74 (dd, 2H, J=3.1, 11.7 Hz, Ser—CH), 4.63 (dd, 2H, J=3.1, 11.7 Hz, Ser—CH), 4.41 (dd, 2H, J=5.5, 18.3 Hz, Gly—CH), 4.09 (d, 2H, J=18.3 Hz, Gly—CH), 3.98 (m, 2H, Pip-G-CH), 3.76 (d, 2H, J=12.8 Hz, Pip-G-CH), 3.24 (d, 2H, J=16.6 Hz, Sar—CH), 2.90 (s, 6H, Val-NCH$_3$), 2.88 (s, 6H, Sar-NCH$_3$), 1.98 (d split septet, 2H, J=6.5, 11.0 Hz, Val—CH), 1.75–1.40 (m, 12H, Pip-(CH$_2$)$_3$), 0.92 (d, 6H, J=6.5 Hz, Val—CH$_3$), 0.74 (d, 6H, J=6.5 Hz, Val—CH$_3$); $^{13}$C NMR (CDCl$_3$, 100 MHz) 172.8, 169.3, 169.2, 167.6, 166.7, 164.4, 154.1, 136.1, 135.6, 133.9, 129.1, 128.7, 128.3, 128.2, 128.0, 127.0, 126.2, 124.7, 122.5, 108.8, 71.2, 63.2, 62.2, 52.3, 51.4, 49.2, 43.9, 42.0, 34.9, 30.0, 28.8, 26.5, 24.8, 20.3, 19.4, 18.9; IR (KBr)$_{max}$ 3329, 2939, 1742, 1639, 1595, 1498, 1455, 1416, 1355, 1259, 1224, 1135, 1076, 1016, 920, 835, 732 cm$^{-1}$; FABHRMS (NBA) m/z 1399.6622 (M+H$^+$, C$_{76}$H$_{90}$N$_{10}$O$_{16}$ requires 1399.6615).

N-(Naphthyl-2-carbonyl)-D-Ser-Pip-Gly-Sar-NMe-Val)$_2$ (Serine Hydroxyl) Dilactone (7) Shown in FIG. 2:

Synthesized according to the general procedure outline above using 23 and 3-benzyloxy-6-methoxyquinoline-2-carboxylic acid except substituting naphthalene-2-carboxylic acid for 3-benzyloxy-6-methoxyquinoline-2-carboxylic acid: 0.0095 mmol scale; flash chromatography (SiO$_2$, 1 (16 cm, 0–5% EtOH—CH$_2$Cl$_2$ gradient) afforded 7 (10.3 mg, 11.3 mg theoretical, 91%) as white powder: R$_f$=0.24 (50% CH$_3$CN-EtOAc); [α]$^{23}$D –101 (c 0.34, CHCl$_3$); $^1$H NMR (CDCl$_3$, 400 MHz) 8.56 (d, 2H, J=4.3 Hz, Ser-NH), 8.33 (s, 2H, C1—H), 7.90 (d, 2H, J=4.3 Hz, Gly-NH), 7.86 (d, 4H, J=8.8 Hz, C5 and C8—H), 7.84 (dd, 2H, J=8.9, 1.6 Hz, C3—H), 7.54 (m, 4H, C6 and C7—H), 5.39 (d, 2H, J=16.5 Hz, Sar—CH), 5.38 (d, 2H, J=4.9 Hz, Pip—CH), 5.32 (m, 2H, J=16.5 Hz, Ser—CH), 4.83 (d, 2H, J=11.0 Hz, Val—CH), 4.81 (d, 2H, J=11.8 Hz, Ser—CH), 4.64 (dd, 2H, J=11.8, 3.2 Hz, Ser—CH), 4.45 (dd, 2H, J=18.3, 5.8 Hz, Gly—CH), 4.06 (d, 2H, J=18.3 Hz, Gly—CH), 4.00 (m, 2H, Pip-G-CH), 3.77 (m, 2H, Pip-G-CH), 3.47 (d, 2H, J=16.5 Hz, Sar—CH), 2.99 (s, 6H, Val-NCH$_3$), 2.94 (s, 6H, Sar-NCH$_3$), 2.08 (d split septet, 2H, J=6.5, 11.0 Hz, Val—CH), 1.80–1.45 (m, 12H, Pip(CH$_2$)$_3$), 0.95 (d, 6H, J=6.5 Hz, Val—CH$_3$), 0.81 (d, 6H, J=6.5 Hz, Val—CH$_3$); $^{13}$C NMR (CDCl$_3$, 100 MHz) 172.6, 169.3, 169.2, 167.6, 167.2, 166.4, 134.8, 132.6, 131.1, 129.0, 128.5, 127.7, 127.6, 126.7, 123.5, 63.1, 62.2, 52.7, 51.1, 49.3, 44.0, 41.9, 35.0, 30.1, 29.7, 28.5, 26.6, 24.7, 20.1, 19.3, 18.9; IR (KBr)$_{max}$ 3322, 2939, 1737, 1639, 1491, 1452, 1413, 1290, 1133, 1098, 1015, 916, 730 cm$^{-1}$; FABHRMS (NBA) m/z 1187.5779 (M+H$^+$, C$_{62}$H$_{78}$N$_{10}$O$_{14}$ requires 1187.5777).

Data for (N-(3-Benzyl-oxypyridyl-2-carbonyl)-D-Ser-Pip-Gly-Sar-NMe-Val)$_2$ (Serine Hydroxyl) Dilactons (9) as Shown in FIG. 2:

Synthesized according to the general procedure outline above using 23 and 3-benzyloxy-6-methoxyquinoline-2-carboxylic acid except substituting 3-benzyloxypyridine-2-carboxylic acid for 3-benzyloxy-6-methoxyquinoline-2-carboxylic acid: 0.0117 mmol scale; flash chromatography (SiO$_2$, 1 (16 cm, 0–5% EtOH—CH$_2$Cl$_2$ gradient) afforded 9 (13.0 mg, 15.2 mg theoretical, 85%) as white powder: R$_f$=0.4 (5% EtOH—CH$_2$Cl$_2$); [α]$^{23}$D –64 (c 0.13, CHCl$_3$); $^1$H NMR (CDCl$_3$, 400 MHz) 9.04 (d, 2H, J=5.8 Hz, Ser-NH), 8.47 (d, 2H, J=4.6 Hz, Gly-NH), 8.17 (dd, 2H, J=1.2, 4.2 Hz, C6'—H), 7.50–7.26 (m, 14H, C4', C5', and phenyl CH), 5.40 (d, 2H, J=16.5 Hz, Sar—CH), 5.31–5.20 (m, 6H, PhCH$_2$ and Ser—CH), 4.81 (d, 2H, J=11.0 Hz, Val—CH), 4.78 (d, 2H, J=12.0 Hz, Ser—CH), 4.58 (dd, 2H, J=2.7, 12.0 Hz, Ser—CH), 4.41 (dd, 2H, J=5.8, 18.3 Hz, Ser—CH), 4.01 (d; 2H, J=18.3 Hz, Ser—CH), 3.98 (m, 2H, Pip-G-CH), 3.74 (d, 2H, J=13.8 Hz, Pip-G-CH), 3.41 (d, 2H, J=16.5 Hz, Sar—CH), 2.97 (s, 6H, Val-NCH$_3$), 2.91 (s, 6H, Sar-NCH$_3$), 2.06 (d split septet, 2H, J=6.5, 11.0 Hz, Val—CH), 1.80–1.42 (m, 12H, Pip-(CH$_2$)$_3$), 0.95 (d, 6H, J=6.5 Hz, Val—CH$_3$), 0.80 (d, 6H, J=6.5 Hz, Val—CH$_3$); $^{13}$C NMR (CDCl$_3$, 100 MHz) 172.7, 169.3, 169.2, 167.7, 167.0, 163.4, 155.0, 140.8, 139.0, 135.9, 128.7, 128.0, 127.8, 126.9, 122.9, 71.0, 63.1, 62.2, 52.4, 50.6, 49.3, 43.8, 41.9, 34.9, 30.3, 28.7, 26.6, 24.8, 20.2, 19.4, 19.0; IR (KBr)$_{max}$ 3326, 2930, 1741, 1669, 1638, 1494, 1454, 1288, 1136, 1017, 739, 698 cm$^{-1}$; FABHRMS (NBA-CsI) m/z 1433.5160 (M+Cs$^+$, C$_{66}$H$_{84}$N$_{12}$O$_{16}$ requires 1433.5183).

Data for (N-(Pyridyl-2-carbonyl)-D-Ser-Pip-Gly-Sar-NMe-Val)$_2$ (Serine Hydroxyl) Dilactone (10) as Shown in FIG. 2:

Synthesized according to the general procedure outline above using 23 and 3-benzyloxy-6-methoxyquinoline-2-carboxylic acid except substituting pyridine-2-carboxylic acid for 3-benzyloxy-6-methoxyquinoline-2-carboxylic acid: 0.0076 mmol scale; flash chromatography (SiO$_2$, 1 (16 cm, 0–10% EtOH—CH$_2$Cl$_2$ gradient) afforded 10 (7.8 mg, 8.3 mg theoretical, 94%) as white powder: R$_f$=0.6 (10% EtOH—CH$_2$Cl$_2$); [α]$^{23}$D –103 (c 0.35, CHCl$_3$); $^1$H NMR (CDCl$_3$, 400 MHz) 9.23 (d, 2H, J=6.4 Hz, Ser-NH), 8.50 (m, 4H, Gly-NH and C5—H), 8.17 (d, 2H, J=7.8 Hz, C3—H), 7.82 (ddd, 2H, J=1.7, 7.6, 7.7 Hz, C4—H), 7.39 (ddd, 2H, J=1.2, 4.6, 7.6 Hz, C5—H), 5.47 (d, 2H, J=5.5 Hz, Pip—CH), 5.46 (d, 2H, J=16.6 Hz, Sar—CH), 5.24 (d, 2H, J=6.4 Hz, Ser—CH), 4.84 (d, 4H, J=11.0 Hz, Val—CH and Ser—CH), 4.49 (dd, 2H, J=2.8, 11.7 Hz, Ser—CH), 4.42 (dd, 2H, J=5.8, 18.2 Hz, Gly—CH), 4.02 (m, 2H, Pip-G-CH), 4.00 (d, 2H, J=17.0 Hz, Gly—CH), 3.73 (m, 2H, Pip-G-CH), 3.48 (d, 2H, J=16.6 Hz, Sar—CH), 3.03 (s, 6H, Val-NCH$_3$), 2.92 (s, 6H, Sar-NCH$_3$), 2.06 (d split septet, 2H, J=6.5, 11.0 Hz, Val—CH), 1.78–1.45 (m, 12H, Pip-(CH$_2$)$_3$), 0.93 (d, 6H, J=6.5 Hz, Val—CH$_3$), 0.80 (d, 6H, J=6.5 Hz, Val—CH$_3$); $^{13}$C NMR (CDCl$_3$, 100 MHz) 172.7, 169.3, 169.1, 167.8, 166.8, 163.8, 149.6, 148.3, 137.1, 126.2, 122.2, 62.8, 62.1, 52.4, 50.6, 49.3, 43.8, 41.8, 34.9, 30.3, 28.7, 26.4, 24.8, 20.1, 19.4, 18.8; IR (KBr)$_{max}$ 3327, 2936, 1744, 1672, 1637, 1571, 1462, 1426, 1288, 1136, 1017, 918, 731 cm$^{-1}$; FABHRMS (NBA) m/z 1089.5360 (M+H$^+$, C$_{52}$H$_{72}$N$_{12}$O$_{14}$ requires 1089.5369).

Data for (N-(6-Methoxyquinolinyl-2-carbonyl)-D-Ser-Pip-Gly-Sar-NMe-Val)$_2$ (Serine Hydroxyl) Dilactone (13) as Shown in FIG. 2:

Synthesized according to the general procedure outline above using 23 and 3-benzyloxy-6-methoxyquinoline-2-carboxylic acid except substituting 6-methoxyquinoline-2-carboxylic acid for 3-benzyloxy-6-methoxyquinoline-2-carboxylic acid: 0.0081 mmol scale; flash chromatography (SiO$_2$, 1 (16 cm, 0–5% EtOH—CH$_2$Cl$_2$ gradient) afforded 13 (9.0 mg, 10.1 mg theoretical, 89%) as white powder: R$_f$=0.5 (5% EtOH—CH$_2$Cl$_2$); [α]$^{23}$D –122 (c 0.2, CHCl$_3$); $^1$H NMR (CDCl$_3$, 400 MHz) 9.34 (d, 2H, J=6.4 Hz, Ser-NH), 8.52 (d, 2H, J=4.6 Hz, Gly-NH), 8.23 (d, 2H, J=8.5 Hz, C3'—H), 8.15 (d, 2H, J=8.5 Hz, C4'—H), 7.84 (d, 2H, J=9.2 Hz, C8'—H), 7.36 (dd, 2H, J=2.7, 9.2 Hz, C7'—H), 7.10 (d, 2H, J=2.7 Hz, C5'—H), 5.55 (d, 2H, J=5.4 Hz, Pip—CH), 5.54 (d, 2H, J=16.4 Hz, Sar—CH), 5.30 (d, 2H, J=6.4 Hz, Ser—CH), 4.94 (dd, 2H, J=1.5, 11.0 Hz, Ser—CH), 4.85 (d, 2H, J=11.0 Hz, Val—CH), 4.45 (m, 4H, Ser—CH and Gly—CH), 4.06 (m, 4H, Gly—CH and Pip-G-CH), 3.95 (s, 6H, OCH$_3$), 3.76 (d, 2H, J=13.2 Hz, Pip-G-CH), 3.54 (d, 2H, J=16.4 Hz, Sar—CH), 3.13 (s, 6H, Val-NCH$_3$), 2.93 (s, 6H, Sar-NCH$_3$), 2.04 (d split septet, 2H, J=6.5, 11.0 Hz, Val—CH), 1.82–1.50 (m, 12H, Pip-(CH$_2$)$_3$), 0.92 (d, 6H, J=6.5 Hz, Val—CH$_3$), 0.78 (d, 6H, J=6.5 Hz, Val—CH$_3$); $^{13}$C NMR (CDCl$_3$, 100 MHz) 172.7, 169.3, 169.1, 167.7, 167.0, 164.1, 158.8, 147.2, 142.7, 135.7, 131.2, 130.7, 123.2, 119.2, 104.8, 62.8, 62.1, 55.6, 52.4, 50.7, 49.3, 43.8, 41.9, 34.9, 30.4, 28.8, 26.3, 24.9, 20.2, 19.5, 18.8; IR (KBr)$_{max}$ 3329, 2937, 1743, 1672, 1638, 1495, 1462, 1416, 1255, 1136, 1019, 836 cm$^{-1}$; FABHRMS (NBA) m/z 1249.5890 (M+H$^+$, C$_{62}$H$_{80}$N$_{12}$O$_{16}$ requires 1249.5894).

Data for (N-(3-Benzyloxy-6-methylquinolinyl-2-carbonyl)-D-Ser-Pip-Gly-Sar-NMe-Val)$_2$ (Serine Hydroxyl) Dilactone (15) as Shown in FIG. 2:

Synthesized according to the general procedure outline above using 23 and 3-benzyloxy-6-methoxyquinoline-2-carboxylic acid except substituting 6-methyl-3-benzyloxyquinoline-2-carboxylic acid for 3-benzyloxy-6-methoxyquinoline-2-carboxylic acid and followed by general debenzylation as above: 0.012 mmol scale; flash chromatography (SiO$_2$, 1 (16 cm, 0–5% EtOH—CH$_2$Cl$_2$ gradient) afforded 15 (14.5 mg, 17.2 mg theoretical, 84%) as white powder: R$_f$=0.56 (40% CH$_3$CN-EtOAc); [α]$^{23}$D –124 (c 0.24, CHCl$_3$); $^1$H NMR (CDCl$_3$, 400 MHz) 9.03 (d, 2H, J=6.3 Hz, Ser-NH), 8.48 (d, 2H, J=4.5 Hz, Gly-NH), 7.81 (d, 2H, J=8.6 Hz, C7—H), 7.55 (d, 2H, J=7.4 Hz, C8—H), 7.50 (s, 2H, C4—H), 7.44 (s, 2H, C5—H), 7.41–7.35 (m, 8H), 7.32–7.26 (m, 2H, benzyl C4—H), 5.46 (d, 2H, J=6.0 Hz, Pip—CH), 5.45 (d, 2H, J=16.5 Hz, Sar—CH), 5.36–5.32 (m, 6H, Ser—CH and PhCH$_2$), 4.86 (dd, 2H, J=11.6, 1.5 Hz, Ser—CH), 4.83 (d, 2H, J=11.0 Hz, Val—CH), 4.58 (dd, 2H, J=11.6, 2.6 Hz, Ser—CH), 4.42 (dd, 2H, J=18.3, 5.6 Hz, Gly—CH), 4.10–3.98 (m, 4H, Gly—CH and Pip-G-CH), 3.78–3.72 (m, 2H, Pip-G-CH), 3.47 (d, 2H, J=16.5 Hz, Sar—CH), 3.07 (s, 6H, Val-NCH$_3$), 2.92 (s, 6H, Sar-NCH$_3$), 2.50 (s, 6H, CH$_3$), 2.06 (d split septet, 2H, J=11.0, 6.5 Hz, Val—CH), 1.80–1.45 (m, 12H, Pip(CH$_2$)$_3$), 0.95 (d, 6H, J=6.5 Hz, Val—CH$_3$), 0.81 (d, 6H, J=6.5 Hz, Val—CH$_3$); $^{13}$C NMR (CDCl$_3$, 100 MHz) 172.7, 169.2, 169.1, 167.8, 167.1, 163.6, 151.9, 141.5, 140.3, 138.6, 136.1, 130.3, 129.9, 129.2, 128.7, 127.9, 126.9, 125.2, 116.7, 70.8, 62.9, 62.3, 52.5, 50.7, 49.3, 43.8, 41.9, 34.9, 30.4, 28.7, 26.5, 24.8, 21.8, 20.2, 19.4, 19.0; IR (KBr)$_{max}$ 3328, 2928, 1743, 1675, 1639, 1491, 1415, 1352, 1261, 1190, 1136, 1017 cm$^{-1}$; FABHRMS (NBA-CsI) m/z 1561.5766 (M+H$^+$, C$_{76}$H$_{92}$N$_{12}$O$_{16}$ requires 1561.5809).

Data for (N-(3-Benzyloxy-7-chloroquinolinyl-2-carbonyl)-D-Ser-Pip-Gly-Sar-NMe-Val)$_2$ (Serine Hydroxyl) Dilactone (17) as Shown in FIG. 2:

Synthesized according to the general procedure outline above using 23 and 3-benzyloxy-6-methoxyquinoline-2-carboxylic acid except substituting 7-chloro-3-benzyloxyquinoline-2-carboxylic acid for 3-benzyloxy-6-methoxyquinoline-2-carboxylic acid followed by general debenzylation as outline above: 0.0112 mmol scale; flash chromatography (SiO$_2$, 1 (16 cm, 0–10% EtOH—CH$_2$Cl$_2$ gradient) afforded 17 (14.5 mg, 16.4 mg theoretical, 88%) as white powder: R$_f$=0.32 (20% CH$_3$CN-EtOAc); [α]$^{23}$D –138 (c 0.6, CHCl$_3$); $^1$H NMR (CDCl$_3$, 400 MHz) 8.93 (d, 2H, J=6.2 Hz, Ser-NH), 8.50 (d, 2H, J=4.4 Hz, Gly-NH), 7.91 (d, 2H, J=2.1 Hz, C8'—H), 7.63 (d, 2H, J=8.8 Hz, C5—H), 7.57 (s, 2H, C4—H), 7.55 (m, 4H, phenyl C2' and C6'—H), 7.47 (dd, 2H, J=2.1, 8.8 Hz, C6—H), 7.42–7.37 (m, 4H, phenyl C3' and C5'—H), 7.32–7.28 (m, 2H, phenyl C4'—H), 5.46 (d, 2H, J=3.1 Hz, Pip—CH), 5.44 (d, 2H, J=16.7 Hz, Sar—CH), 5.36–5.28 (m, 6H, D-Ser—CH and PhCH$_2$), 4.87 (dd, 2H, J=2.8, 11.6 Hz, Ser—CH), 4.84 (d, 2H, J=11.0 Hz, Val—CH), 4.58 (dd, 2H, J=2.8, 11.6 Hz, Ser—CH), 4.43 (dd, 2H, J=5.7, 18.3 Hz, Gly—CH), 4.03 (d, 2H, J=18.3 Hz, Gly—CH), 4.01 (m, 2H, Pip-G-CH), 3.75 (d, 2H, J=13.5 Hz, Pip-G-CH), 3.49 (d, 2H, J=16.7 Hz, Sar—CH), 3.07 (s, 6H, Val-NCH$_3$), 2.93 (s, 6H, Sar-NCH$_3$), 2.08 (d split septet, 2H, J=6.5, 11.0 Hz, Val—CH), 1.80–1.45 (m, 12H, Pip-(CH$_2$)$_3$), 0.95 (d, 6H, J=6.5 Hz, Val—CH$_3$), 0.82 (d, 6H, J=6.5 Hz, Val—CH$_3$); $^{13}$C NMR (CDCl$_3$, 100 MHz) 172.6, 169.3, 169.2, 167.8, 166.9, 163.1, 151.9, 143.6, 141.8, 135.8, 133.2, 129.4, 128.8, 128.6, 128.3, 128.0, 127.6, 126.9, 117.1, 70.9, 62.8, 62.2, 52.5, 50.8, 49.3, 43.9, 41.9, 34.9, 30.3, 28.7, 26.5, 24.8, 20.2, 19.4, 19.0; IR (KBr)$_{max}$ 3323, 2938, 1740, 1672, 1637, 1497, 1415, 1345, 1287, 1260, 1191, 1135, 1016, 940, 733 cm$^{-1}$; FABHRMS (NBA-CsI) m/z 1601.4828 (M+Cs$^+$, C$_{74}$H$_{86}$Cl$_2$N$_{12}$O$_{16}$ requires 1601.4716).

Data for (N-(Quinoxalyl-2-carbonyl)-D-Ser-Pip-Gly-Sar-NMe-Val)$_2$ (Serine Hydroxyl) Dilactone (18) as Shown in FIG. 2:

Synthesized according to the general procedure outline above using 23 and 3-benzyloxy-6-methoxyquinoline-2-carboxylic acid except substituting quinoxaline-2-carboxylic acid for 3-benzyloxy-6-methoxyquinoline-2-carboxylic acid: 0.0091 mmol scale; flash chromatography (SiO$_2$, 1 (16 cm, 0–5% EtOH—CH$_2$Cl$_2$ gradient) afforded 18 (9.3 mg, 10.8 mg theoretical, 86%) as white powder: R$_f$=0.58 (10% EtOH—CH$_2$Cl$_2$); [α]$^{23}$D −128 (c 0.44, CHCl$_3$); 1H NMR (CDCl$_3$, 400 MHz) 9.66 (s, 2H, C3'—H), 8.54 (d, 2H, J=4.7 Hz, Gly-NH), 8.18 (d, 2H, J=8.2 Hz, C5'—H), 7.99 (d, 2H, J=8.0 Hz, C8'—H), 7.90–7.79 (m, 4H, C6' and C7'—H), 5.54 (d, 2H, J=4.0 Hz, Pip—CH), 5.52 (d, 2H, J=16.5 Hz, Sar—CH), 5.31 (d, 2H, J=5.8 Hz, Ser—CH), 4.98 (d, 2H, J=11.3 Hz, Ser—CH), 4.86 (d, 2H, J=11.0 Hz, Val—CH), 4.49–4.40 (m, 4H, Ser—CH, and Gly—CH), 4.10–4.00 (m, 4H, Gly—CH and Pip-G-CH), 3.76 (d, 2H, J=13.3 Hz, Pip-G-CH), 3.53 (d, 2H, J=16.5 Hz, Sar—CH), 3.09 (s, 6H, Val-NCH$_3$), 2.94 (s, 6H, Sar-NCH$_3$), 2.03 (d split septet, 2H, J=6.5, 11.0 Hz, Val—CH), 1.82–1.50 (m, 12H, Pip-(CH$_2$)$_3$), 0.92 (d, 6H, J=6.5 Hz, Val—CH$_3$), 0.78 (d, 2H, J=6.5 Hz, Val—CH$_3$); $^{13}$C NMR (CDCl$_3$, 100 MHz) 172.6, 169.4, 169.2, 167.7, 166.6, 162.6, 144.0, 143.81 143.2, 140.4, 131.6, 130.7, 129.6, 129.5, 62.5, 62.0, 52.6, 50.8, 49.3, 43.9, 41.9, 34.9, 30.2, 28.7, 26.3, 24.9, 20.2, 19.4, 18.7; IR (KBr)$_{max}$ 3330, 2938, 1745, 1682, 1638, 1509, 1491, 1417, 1283, 1136, 1015, 916, 776, 731 cm$^{-1}$; FABHRMS (NBA) m/z 1191.5591 (M+H$^+$, C$_{58}$H$_{74}$N$_{14}$O$_{14}$ requires 1191.5587).

Data for (N-(3-Benzyl-oxyquinoxalyl-2-carbonyl)-D-Ser-Pip-Gly-Sar-NMe-Val)$_2$ (Serine Hydroxyl) Dilactone (20) as Shown in FIG. 2:

Synthesized according to the general procedure outline above using 23 and 3-benzyloxy-6-methoxyquinoline-2-carboxylic acid except substituting 3-benzyloxyquinoxaline-2-carboxylic acid for 3-benzyloxy-6-methoxyquinoline-2-carboxylic acid: 0.0118 mmol scale; flash chromatography (SiO$_2$, 1 (16 cm, 0–5% EtOH—CH$_2$Cl$_2$ gradient) afforded 20 (12.5 mg, 16.5 mg theoretical, 76%) as white powder: R$_f$=0.22 (20% CH$_3$CN-EtOAc); [α]$^{23}$D −128 (c 0.3, CHCl$_3$); $^1$H NMR (CDCl$_3$, 400 MHz) 10.82 (d, 2H, J=6.2 Hz, Ser-NH), 8.44 (d, 2H, J=4.8 Hz, Gly-NH), 8.19 (dd, 2H, J=1.3, 8.0 Hz, C8'—H), 7.57 (ddd, 2H, J=1.3, 7.8, 8.0 Hz, C6'—H), 7.40 (dd, 2H, J=7.4, 7.4 Hz, C7'—H), 7.33–7.18 (m, 12H, C5'-H and phenyl CH), 5.60–5.40 (m, 10H, Pip—CH, Sar—CH, Ser—CH, and PhCH$_2$), 4.87 (d, 2H, J=11.1 Hz, Ser—CH), 4.82 (d, 2H, J=11.0 Hz, Val—CH), 4.55 (dd, 2H, J=2.8, 11.7 Hz, Ser—CH), 4.41 (dd, 2H, J=5.8, 18.0 Hz, Gly—CH), 4.10–4.00 (m, 2H, Pip-G-CH), 3.94 (d, 2H, J=18.0 Hz, Gly—CH), 3.77–3.72 (m, 2H, Pip-G-CH), 3.43 (d, 2H, J=16.6 Hz, Sar—CH), 2.98 (s, 6H, Val-NCH$_3$), 2.89 (s, 6H, Sar-NCH$_3$), 2.05 (d split septet, 2H, J=6.5, 11.0 Hz, Val—CH), 1.80–1.40 (m, 12H, Pip-(CH$_2$)$_3$), 0.94 (d, 6H, J=6.5 Hz, Val—CH$_3$), 0.79 (d, 6H, J=6.5 Hz, Val—CH$_3$); $^{13}$C NMR (CDCl$_3$, 100 MHz) 172.6, 169.3, 169.0, 167.8, 166.3, 160.5, 155.0, 144.5, 134.7, 133.3, 133.2, 132.8, 132.6, 128.9, 127.8, 126.8, 124.6, 114.5, 62.8, 62.1, 52.4, 51.7, 49.3, 46.2, 43.9, 41.8, 34.9, 30.4, 28.9, 26.4, 24.9, 20.2, 19.4, 18.9; IR (KBr)$_{max}$ 3321, 2396, 1741, 1684, 1638, 1497, 1464, 1283, 1136, 1017, 733 cm$^{-1}$; FABHRMS (NBA) m/z 1403.6430 (M+H$^+$, C$_{72}$H$_{86}$N$_{14}$O$_{16}$ requires 1403.6424).

Data for (N-(Iso-quinolinyl-3-carbonyl)-D-Ser-Pip-Gly-Sar-NMe-Val)$_2$ (Serine Hydroxyl) Dilactone (21):

Synthesized according to the general procedure outline above using 23 and 3-benzyloxy-6-methoxyquinoline-2-carboxylic acid except substituting isoquinoline-3-carboxylic acid for 3-benzyloxy-6-methoxyquinoline-2-carboxylic acid: 0.0148 mmol scale; flash chromatography (SiO$_2$, 2×15 cm, 5% EtOH—CH$_2$Cl$_2$ gradient) afforded 21 (16.5 mg, 17.6 mg theoretical, 94%) as white powder: R$_f$=0.17 (10% CH$_3$CN-EtOAc); [α]$^{23}$D −111 (c 0.24, CHCl$_3$); $^1$H NMR (CDCl$_3$, 400 MHz) 9.42 (d, 2H, J=6.3 Hz, Ser-NH), 9.11 (s, 2H, C4'—H), 8.59 (s, 2H, C1'—H), 8.51 (d, 2H, J=4.6 Hz, Gly-NH), 7.99 (d, 2H, J=8.0 Hz, C5'—H), 7.97 (d, 2H, J=8.1 Hz, C8'—H), 7.74 (ddd, 2H, J=1.2, 6.9, 8.1 Hz, C7'—H), 7.68 (ddd, 2H, J=1.2, 6.9, 8.0 Hz, C6'—H), 5.50 (d, 2H, J=5.2 Hz, Pip—CH), 5.49 (d, 2H, J=16.5 Hz, Sar—CH), 5.31 (d, 2H, J=6.3 Hz, Ser—CH), 4.90 (dd, 2H, J=2.8, 11.7 Hz, Ser—CH), 4.84 (d, 2H, J=11.0 Hz, Val—CH), 4.52 (dd, 2H, J=2.8, 11.7 Hz, Ser—CH), 4.43 (dd, 2H, J=5.9, 18.2 Hz, Gly—CH), 4.03 (m, 2H, Pip-G-CH), 4.01 (d, 2H, J=18.2 Hz, Gly—CH), 3.76 (d, 2H, J=13.0 Hz, Pip-G-CH), 3.49 (d, 2H, J=16.5 Hz, Sar—CH), 3.06 (s, 6H, Val-NCH$_3$), 2.92 (s, 6H, Sar-NCH$_3$), 2.04 (d split septet, 2H, J=6.5, 11.0 Hz, Val—CH), 1.80–1.45 (m, 12H, Pip-(CH$_2$)$_3$), 0.92 (d, 6H, J=6.5 Hz, Val—CH$_3$), 0.79 (d, 6H, J=6.5 Hz, Val—CH$_3$); $^{13}$C NMR (CDCl$_3$, 100 MHz) 172.7, 169.3, 169.1, 167.8, 166.9, 164.3, 151.3, 143.4, 135.9, 130.9, 129.7, 128.8, 128.1, 127.5, 120.3, 62.9, 62.1, 52.4, 50.7, 49.3, 43.8, 41.8, 34.9, 30.4, 28.7, 26.4, 24.8, 20.2, 19.4, 18.8; IR (KBr)$_{max}$ 3497, 3328, 2938, 1742, 1639, 1505, 1436, 1287, 1136, 1095, 1016, 920 cm$^{-1}$; FABHRMS (NBA-CsI) m/z 1321.4670 (M+Cs$^+$, C$_{60}$H$_{76}$N$_{12}$O$_{14}$ requires 1321.4658).

Data for (N-(Isoquinolinyl-1-carbonyl)-D-Ser-Pip-Gly-Sar-NMe-Val)$_2$ (Serine Hydroxyl) Dilactone (22) as Shown in FIG. 2:

Synthesized according to the general procedure outline above using 23 and 3-benzyloxy-6-methoxyquinoline-2-carboxylic acid except substituting isoquinoline-1-carboxylic acid for 3-benzyloxy-6-methoxyquinoline-2-carboxylic acid: 0.0139 mmol scale; flash chromatography (SiO$_2$, 2×15 cm, 0–5% EtOH—CH$_2$Cl$_2$ gradient) afforded 22 (13.6 mg, 16.5 mg theoretical, 82%) as white powder: R$_f$=0.31 (10% CH$_3$CN-EtOAc); [α]$^{23}$D −74 (c 1.15, CHCl$_3$); $^1$H NMR (CDCl$_3$, 400 MHz) 9.56 (d, 2H, J=1.6, 8.2 Hz, C8'—H), 9.39 (d, 2H, J=6.3 Hz, Ser-NH), 8.51 (d, 2H, J=4.8 Hz, Gly-NH), 8.42 (d, 2H, J=5.4 Hz, C3'—H), 7.83 (dd, 2H, J=2.0, 7.1 Hz, C5'—H), 7.77 (d, 2H, J=5.4 Hz, C4'—H), 7.72–7.65 (m, 4H, C6' and C7'—H), 5.49 (d, 2H, J=5.0 Hz, Pip—CH), 5.47 (d, 2H, J=16.6 Hz, Sar—CH), 5.31 (d, 2H, J=6.3 Hz, Ser—CH), 4.90 (dd, 2H, J=1.6, 11.7 Hz, Ser—CH), 4.85 (d, 2H, J=11.0 Hz, Val—CH), 4.54 (dd, 2H, J=2.8, 11.7 Hz, Ser—CH), 4.43 (dd, 2H, J=5.9, 18.3 Hz, Gly—CH), 4.04 (m, 2H, Pip-G-CH), 4.00 (d, 2H, J=18.3 Hz, Gly—CH), 3.77 (d, 2H, J=13.3 Hz, Pip-G-CH), 3.48 (d, 2H, J=16.6 Hz, Sar—CH), 3.05 (s, 6H, Val-NCH$_3$), 2.92 (s, 6H, Sar-NCH$_3$), 2.07 (d split septet, 2H, J=6.6, 11.0 Hz, Val—CH), 1.80–1.45 (m, 12H, Pip-(CH$_2$)$_3$), 0.94 (d, 6H, J=6.6 Hz, Val—CH$_3$), 0.80 (d, 6H, J=6.6 Hz, Val—CH$_3$); $^{13}$C NMR (CDCl$_3$, 100 MHz) 172.7, 169.4, 169.1, 167.8, 167.0, 165.5, 147.6, 140.5, 137.3, 130.4, 128.6, 127.6, 127.1, 126.8, 124.3, 62.8, 62.1, 52.5, 50.7, 49.3, 43.8, 41.8, 34.9, 30.4, 28.7, 26.4, 24.9, 20.1, 19.5, 18.9; IR $(KBr)_{max}$ 3518, 3325, 2936, 1744, 1668, 1638, 1505, 1490, 1463, 1417, 1287, 1259, 1136, 1017, 837 cm$^{-1}$; FABHRMS (NBA-CsI) m/z 1321.4739 (M+Cs$^+$, $C_{60}H_{76}N_{12}O_{14}$ requires 1321.4658).

Data for (N-(3-Hydroxynaphthyl-2-carbonyl)-D-Ser-Pip-Gly-Sar-NMe-Val)$_2$ (Serine Hydroxyl) Dilactone (5) as Shown in FIG. 2:

Synthesized according to the general procedure outline above using 23 and 3-benzyloxy-6-methoxyquinoline-2-carboxylic acid except substituting 3-hydroxy-3-benzyloxynaphthalene-2-carboxylic acid for 3-benzyloxy-6-methoxy-quinoline-2-carboxylic acid followed by general debenzylation conditions: 0.0112 mmol scale; flash chromatography (SiO$_2$, 2 (15 cm, 40% CH$_3$CN-EtOAc) afforded 5 (11.0 mg, 13.7 mg theoretical, 80%) as a white powder: $R_f$=0.56 (40% CH$_3$CN-EtOAc); $[\alpha]^{23}$D −102 (c 0.26, CHCl$_3$); $^1$H NMR (CDCl$_3$, 400 MHz) 11.60 (s, 2H, OH), 8.58 (d, 2H, J=4.3 Hz, Ser-NH), 8.17 (d, 2H, J=5.2 Hz, Gly-NH), 7.96 (s, 2H, C4—H), 7.71 (d, 2H, J=8.4 Hz, C5—H), 7.68 (d, 2H, J=8.5 Hz, C8—H), 7.47 (dd, 2H, J=7.5, 7.7 Hz, C7—H), 7.31 (s, 2H, C1—H), 7.30 (dd, 2H, J=7.5, 7.7 Hz, C6—H), 5.42 (d, 2H, J=5.8 Hz, Pip—CH), 5.40 (d, 2H, J=16.5 Hz, Sar—CH), 5.26 (br s, 2H, Ser—CH), 4.84 (d, 2H, J=11.0 Hz, Val—CH), 4.80 (d, 2H, J=11.8 Hz, Ser—CH), 4.64 (dd, 2H, J=11.8, 1.2 Hz, Ser—CH), 4.46 (dd, 2H, J=18.4, 5.2 Hz, Gly—CH), 4.07 (d, 2H, J=18.4 Hz, Gly—CH), 4.01 (m, 2H, Pip-G-CH), 3.75 (m, 2H, Pip-G-CH), 3.49 (d, 2H, J=16.5 Hz, Sar—CH), 3.01 (s, 6H, Val-NCH$_3$), 2.96 (s, 6H, Sar-NCH$_3$), 2.07 (d split septet, 2H, J=11.0, 6.5 Hz, Val—CH), 1.80–1.45 (m, 12H, Pip (CH$_2$)$_3$), 0.95 (d, 6H, J=6.5 Hz, Val—CH$_3$), 0.82 (d, 6H, J=6.5 Hz, Val—CH$_3$); $^{13}$C NMR (CDCl$_3$, 100 MHz) 172.4, 169.4, 169.2, 168.9, 167.6, 166.8, 156.8, 137.1, 128.6, 128.5, 127.2, 126.8, 126.3, 123.9, 116.6, 112.4, 62.6, 62.2, 52.8, 51.0, 49.3, 44.0, 41.9, 35.1, 30.1, 28.4, 26.6, 24.7, 20.0, 19.3, 18.9; IR $(KBr)_{max}$ 3321, 2938, 1743, 1667, 1638, 1509, 1463, 1417, 1287, 1232, 1135, 1016, 919, 730 cm$^{-1}$; FABHRMS (NBA) m/z 1219.5640 (M+H$^+$, $C_{62}H_{78}N_{10}O_{16}$ requires 1219.5676).

Data for N-(3-Hydroxypyridyl-2-carbonyl)-D-Ser-Pip-Gly-Sar-NMe-Val)$_2$ (Serine Hydroxyl) Dilactone (8) as Shown in FIG. 2:

Synthesized according to the general procedure outline above using 23 and 3-benzyloxy-6-methoxyquinoline-2-carboxylic acid except substituting 3-hydroxypyridine-2-carboxylic acid for 3-benzyloxy-6-methoxyquinoline-2-carboxylic acid: 0.0062 mmol scale; flash chromatography (SiO$_2$, 1 (16 cm, 0–5% EtOH—CH$_2$Cl$_2$ gradient) afforded 8 (6.6 mg, 7.0 mg theoretical, 94%) as a white powder: $R_f$=0.62 (10% EtOH—CH$_2$Cl$_2$); $[\alpha]^{23}$D −85 (c 0.21, CHCl$_3$); $^1$H NMR (CDCl$_3$, 400 MHz) 11.87 (s, 2H, OH), 9.22 (d, 2H, J=6.2 Hz, Ser-NH), 8.50 (d, 2H, J=5.1 Hz, Gly-NH), 8.01 (dd, 2H, J=3.9, 1.7 Hz, C4—H), 7.33–7.26 (m, 4H, C5—H and C6—H), 5.48 (d, 2H, J=5.8 Hz, Pip—CH), 5.46 (d, 2H, J=16.5 Hz, Sar—CH), 5.19 (d, 2H, J=6.2 Hz, Ser—CH), 4.85 (d, 4H, J=11.0 Hz, Val—CH and Ser—CH), 4.47 (dd, 2H, J=12.1, 2.7 Hz, Ser—CH), 4.42 (dd, 2H, J=18.5, 5.8 Hz, Gly—CH), 4.06–3.98 (m, 4H, Gly—CH and Pip-G-CH), 3.70 (d, 2H, J=13.1 Hz, Pip-G-CH), 3.48 (d, 2H, J=16.5 Hz, Sar—CH), 3.01 (s, 6H, Val-NCH$_3$), 2.92 (s, 6H, Sar-NCH$_3$), 2.07 (d split septet, 2H, J=11.0, 6.5 Hz, Val—CH), 1.80–1.50 (m, 12H, Pip-(CH$_2$)$_3$), 0.95 (d, 6H, J=6.5 Hz, Val—CH$_3$), 0.81 (d, 6H, J=6.5 Hz, Val—CH$_3$); $^{13}$C NMR (CDCl$_3$, 100 MHz) 172.6, 169.4, 169.1, 168.3, 167.7, 166.3, 157.8, 139.8, 131.3, 128.6, 125.9, 62.5, 52.5, 50.3, 49.3, 43.9, 41.8, 34.9, 30.3, 28.7, 26.4, 24.8, 20.1, 19.4, 18.8; IR $(KBr)_{max}$ 3327, 2930, 1744, 1672, 1638, 1519, 1450, 1294, 1135, 1016, 919 cm$^{-1}$; FABHRMS (NBA) m/z 1121.5198 (M+H$^+$, $C_{52}H_{72}N_{12}O_{16}$ requires 1121.5268).

Data for (N-(-3-Hydroxy-6-methylquinolinyl-2-carbonyl)-D-Ser-Pip-Gly-Sar-NMe-Val)$_2$ (Serine Hydroxyl) Dilactone (14) as Shown in FIG. 2:

Synthesized according to the general procedure outline above using 23 and 3-benzyloxy-6-methoxyquinoline-2-carboxylic acid except substituting 3-benzyloxyquinoline-2-carboxylic acid for 3-benzyloxy-6-methoxyquinoline-2-carboxylic acid: 0.0063 mmol scale; flash chromatography (SiO$_2$, 1×16 cm, EtOAc) afforded 14 (7.2 mg, 7.9 mg theoretical, 91%) as a white powder: $R_f$=0.56 (EtOAc); $[\alpha]^{23}$D −153 (c 0.24, CHCl$_3$); $^1$H NMR (CDCl$_3$, 400 MHz) 11.71 (s, 2H, OH), 9.51 (d, 2H, J=5.9 Hz, Ser-NH), 8.52 (d, 2H, J=3.8 Hz, Gly-NH), 7.69 (d, 2H, J=8.7 Hz, C7—H), 7.52 (s, 2H, C4—H), 7.45 (s, 2H, C5—H), 7.32 (d, 2H, J=8.3 Hz, C8—H), 5.56 (d, 2H, J=5.3 Hz, Pip—CH), 5.54 (d, 2H, J=16.5 Hz, Sar—CH), 5.25 (d, 2H, J=5.9 Hz, Ser—CH), 4.97 (d, 2H, J=11.6 Hz, Ser—CH), 4.86 (d, 2H, J=11.0 Hz, Val—CH), 4.43 (m, 4H, Ser—CH and Gly—CH), 4.05 (m, 4H, Gly—CH and Pip-G-CH), 3.73 (m, 2H, Pip-G-CH), 3.55 (d, 2H, J=16.5 Hz, Sar—CH), 3.11 (s, 6H, Val-NCH$_3$), 2.94 (s, 6H, Sar-NCH$_3$), 2.50 (s, 6H, CH$_3$), 2.03 (d split septet, 2H, J=11.0, 6.5 Hz, Val—CH), 1.85–1.50 (m, 12H, Pip(CH$_2$)$_3$), 0.92 (d, 6H, J=6.5 Hz, Val—CH$_3$), 0.78 (d, 6H, J=6.5 Hz, Val—CH$_3$); $^{13}$C NMR (CDCl$_3$, 100 MHz) 172.6, 169.4, 169.2, 167.9, 167.7, 166.3, 153.9, 140.2, 138.8, 133.8, 132.2, 129.7, 129.1, 125.1, 119.5, 62.3, 62.0, 52.5, 50.5, 49.3, 43.9, 41.9, 34.9, 30.3, 28.8, 26.2, 24.9, 21.8, 20.2, 19.4, 18.7; IR $(KBr)_{max}$ 3330, 2934, 1746, 1672, 1640, 1519, 1469, 1416, 1338, 1286, 1191, 1135, 1096, 1016, 909, 820, 734 cm$^{-1}$; FABMS (NBA) m/z 1250 (M+H$^+$).

Data for (N-(7-Chloro-3-hydroxyquinolinyl-2-carbonyl)-D-Ser-Pip-Gly-Sar-NMe-Val)$_2$ (Serine Hydroxyl) Dilactone (16) as Shown in FIG. 2:

Synthesized according to the general procedure outline above using 23 and 3-benzyloxy-6-methoxyquinoline-2-carboxylic acid except substituting 7-chloro-3-hydroxyquinoline-2-carboxylic acid for 3-benzyloxy-6-methoxyquinoline-2-carboxylic acid: 0.0094 mmol scale; flash chromatography (SiO$_2$, 1 (16 cm, EtOAc) afforded 16 (9.4 mg, 12.1 mg theoretical, 78%) as white powder: $R_f$=0.52 (20% CH$_3$CN-EtOAc); $[\alpha]^{23}$D −168 (c 0.6, CHCl$_3$); $^1$H NMR (CDCl$_3$, 400 MHz) 11.82 (s, 2H, OH), 9.51 (br s, 2H, Ser-NH), 8.55 (br s, 2H, Gly-NH), 7.82 (s, 2H, C4—H), 7.66–7.61 (m, 4H, C6 and C8—H), 7.45 (d, 2H, J=8.6 Hz, C5—H), 5.57 (d, 2H, J=4.8 Hz, Pip—CH), 5.53 (d, 2H, J=16.5 Hz, Sar—CH), 5.24 (br s, 2H, Ser—CH), 4.98 (d, 2H, J=11.4 Hz, Ser—CH), 4.87 (d, 2H, J=11.0 Hz, Val—CH), 4.44 (m, 4H, Ser—CH and Gly—CH), 4.05 (m, 4H, Gly—CH and Pip-G-CH), 3.74 (m, 2H, Pip-G-CH), 3.57 (d, 2H, J=16.5 Hz, Sar—CH), 3.10 (s, 6H, Val-NCH$_3$), 2.95 (s, 6H, Sar-NCH$_3$), 2.05 (d split septet, 2H, J=11.0, 6.5 Hz, Val—CH), 1.80–1.50 (m, 12H, Pip-(CH$_2$)$_3$), 0.92 (d, 6H, J=6.5 Hz, Val—CH$_3$), 0.79 (d, 6H, J=6.5 Hz, Val—CH$_3$); $^{13}$C NMR (CDCl$_3$, 100 MHz) 172.6, 169.4, 169.1, 167.8, 167.4, 166.1, 154.1, 141.5, 135.4, 132.8, 130.3, 129.6, 128.0, 127.6, 120.5, 62.2, 61.9, 52.6, 50.7, 49.3, 43.9, 41.9, 34.9, 30.2, 28.8, 26.3, 24.9, 20.2, 19.4, 18.7; IR $(KBr)_{max}$ 3328, 2939, 1745, 1667, 1641, 1519, 1417, 1333, 1287, 1191, 1136, 1094, 1017, 917, 731 cm$^{-1}$; FABHRMS (NBA-CsI) m/z 1421.3715 (M+Cs$^+$, $C_{60}H_{74}Cl_2N_{12}O_{16}$, requires 1421.3777).

Synthesis of Compound 22:

Synthesized according to the general procedure outline above using 23 and 3-benzyloxy-6-methoxyquinoline-2-carboxylic acid except substituting isoquinoline-1-carboxylic acid for 3-benzyloxy-6-methoxyquinoline-2-carboxylic acid.

Boc-Gly-Sar-OMe (200).

A solution of Boc-Gly-OH (2.70 g, 15.4 mmol) and the HCl salt of $H_2N$-Sar-OMe (2.15 g, 15.4 mmol) in $CH_2Cl_2$ (50 mL) was treated sequentially with $Et_3N$ (2.2 mL, 15.8 mmol), DCC (3.20 g, 15.5 mmol), and DMAP (306 mg, 2.5 mmol) and the reaction mixture was stirred at 25° C. for 20 h. A white precipitate formed in the first 10 min and was removed by filtration at the end of the reaction. The filtrate was concentrated in vacuo. Flash chromatography ($SiO_2$, 5×16 cm, 40% EtOAc-hexane eluent) afforded 200 (3.21 g, 4.01 g, theoretical, 80%) as a colorless oil which solidified on standing: mp 72–73° C. (EtOAc-hexane, colorless cubes); $R_f$=0.32 (50% EtOAc-hexane); $^1$H NMR ($CDCl_3$, 400 MHz) 4:1 mixture of two conformers, for the major conformer: 5.44 (s, 1H), 4.14 (s, 2H), 4.02 (d, 2H, J=4.3 Hz), 3.73 (s, 3H), 3.02 (s, 3H), 1.43 (s, 9H); $^{13}$C NMR ($CDCl_3$, 100 MHz) for major conformer: 169.3, 168.7, 155.7, 79.6, 52.2, 49.4, 42.2, 35.2, 28.3; IR $(KBr)_{max}$ 3419, 2978, 2934, 1754, 1715, 1667, 1488, 1424, 1367, 1249, 1208, 1175, 1120, 1051, 952, 871, 764, 712 $cm^{-1}$; FABHRMS (NBA-NaI) m/z 283.1259 ($M+Na^+$, $C_{11}H_{20}N_2O_5$ requires 283.1270).

Anal. Calcd for $C_{11}H_{20}N_2O_5$: C, 50.75; H, 7.74; N, 10.76. Found: C, 50.96; H, 7.62; N, 10.63.

Boc-Gly-Sar-OH (300).

Lithium hydroxide monohydrate (598 mg, 14.3 mmol) was added to a solution of 200 (1.22 g, 4.7 mmol) in 20 mL of THF—$CH_3OH$—$H_2O$ (3:1:1) at 25° C. and the resulting reaction mixture was stirred for 3 h. The reaction mixture was poured onto 3M aqueous HCl (10 mL) and extracted with EtOAc (3×20 mL). The combined organic phases were dried ($Na_2SO_4$), filtered and concentrated in vacuo to give 300 (1.16 g, 1.16 g theoretical, 100%) as a colorless oil. This acid was identical to authentic material[14] and was used directly in the next step without further purification: $^1$H NMR ($CDCl_3$, 400 MHz)[14] 5.76 and 5.66 (two br s, 1H), 4.11, 4.00, and 3.91 (three s, 4H), 2.99 and 2.95 (two s, 3H), 1.38 (s, 9H); IR $(neat)_{max}$ 3348, 2979, 2937, 1717, 1654, 1691, 1409, 1368, 1287, 1252, 1167, 1053, 1030, 954, 866, 782, 736 $cm^{-1}$.

Boc-Gly-Sar-NMe-Val-OMe (600).

A solution of 300 (1.81 g, 7.4 mmol) and the HCl salt of 500 (1.34 g, 7.4 mmol) in $CH_2Cl_2$ (40 mL) was treated sequentially with $Et_3N$ (1.1 mL, 7.9 mmol, 1.05 equiv), DCC (1.52 g, 7.4 mmol), and DMAP (93 mg, 0.76 mmol, 0.1 equiv) and the reaction mixture was stirred at 25° C. for 24 h. A white precipitate formed in the first 15 min and was removed by filtration at the end of the reaction. The filtrate was concentrated in vacuo. Flash chromatography ($SiO_2$, 4×16 cm, 50% EtOAc-hexane eluent) afforded 600 (2.04 g, 2.75 g theoretical, 74%) as a colorless oil: $R_f$=0.22 (66% EtOAc-hexane); [ ]$^3$ –62 (c 2.6, $CHCl_3$); $^1$H NMR ($CDCl_3$, 400 MHz) mixture of multiple conformers, 5.42 (br s, 1H), 4.82 (d, 0.6H, J=10.6 Hz), 4.37–4.00 (m, 4H), 3.79 (d, 0.4 H, J=10.9 Hz), 3.72–3.67 (three s, 3H), 3.00–2.84 (six s, 6H), 2.30–2.10 (m, 1H), 1.41 and 1.40 (two s, 9H), 0.94 and 0.84 (two d, 6H, J=6.6 Hz); IR $(neat)_{max}$ 3421, 2969, 2934, 1740, 1712, 1655, 1485, 1404, 1366, 1291, 1251, 1204, 1170, 1051, 1617, 952, 870, 835, 781 $cm^{-1}$; CIHRMS (isobutane) m/z 374.2303 ($C_{17}H_{31}N_3O_6$ requires 374.2291).

Boc-Gly-Sar-NMe-Val-OBn (2000).

A solution of 300 (4.65 g, 18.9 mmol) and the HCl salt of 1900 (4.87 g, 18.9 mmol) in $CH_2Cl_2$ (100 mL) was treated sequentially with $Et_3N$ (3 mL, 21.5 mmol, 1.1 equiv), DMAP (1.15 g, 9.4 mmol, 0.5 equiv), and DCC (3.90 g, 18.9 mmol) and the reaction mixture was stirred at 25° C. for 24 h. A white precipitate formed during the reaction and was removed by filtration. The filtrate was concentrated in vacuo. Flash chromatography ($SiO_2$, 6×20 cm, 50% EtOAc-hexane eluent) afforded 2000 (7.21 g, 8.49 g theoretical, 85%) as a white crystalline solid which was further recrystallized from EtOAc-hexane; mp 97–99° C.; $R_f$=0.21 (50% EtOAc-hexane); [ ]$^3$ –63 (c 0.8, $CHCl_3$); $^1$H NMR ($CDCl_3$, 400 MHz) 7.32 (m, 5H), 5.43 (br s, 1H), 5.16, 5.15, 5.13 (3s, 2H), 4.88 (d, 0.7H, J=10.4 Hz), 4.41, 4.30, 4.11, 4.05 (4d, 2H, J=16 Hz), 4.00 (dd, 1.3H, J=1.7, 4.3 Hz), 3.96 (d, 0.7H, J=4.3 Hz), 3.84 (d, 0.3H, J=10.4 Hz), 2.98, 2.93, 2.89 (3s, 3H), 2.90, 2.85, 2.83 (3s, 3H), 2.33–2.15 (m, 1H), 1.43, 1.42, 1.41 (3s, 9H), 0.95, 0.91, 0.84 (3d, 6H, J=6.6 Hz); $^{13}$C NMR for the major rotamer ($CDCl_3$, 100 MHz) 170.6, 169.1, 168.3, 155.7, 135.5, 128.5, 128.3, 128.2, 79.5, 66.5, 61.9, 49.6, 42.2, 35.3, 30.6, 28.3, 27.5, 19.6, 19.0; IR $(KBr)_{max}$ 3337, 2973, 1736, 1706, 1664, 1534, 1473, 1394, 1296, 1249, 1186, 1052, 955, 742, 703 $cm^{-1}$.

Anal. Calcd for $C_{23}H_{35}N_3O_6$: C, 61.45; H, 7.85; N, 9.35. Found: C, 61.44; H, 7.81; N, 9.23.

Boc-Gly-Sar-NMe-Val-OH (700).

From 600; Lithium hydroxide monohydrate (249 mg, 5.9 mmol) was added to a solution of 600 (740 mg, 1.98 mmol) in 15 mL of THF—$CH_3OH$—$H_2O$ (3:1:1) at 25° C. and the resulting reaction mixture was stirred for 3 h. The reaction mixture was poured onto 3M aqueous HCl (8 mL) and extracted with EtOAc (3×20 mL). The combined organic phases were dried ($Na_2SO_4$), filtered and concentrated in vacuo to give 7 (638 mg, 712 mg theoretical, 90%) as a white solid which was employed directly in the next reaction without further purification: white foam, mp 57–60° C.; $^1$H NMR ($CDCl_3$, 400 MHz) 5.67 and 5.58 (two s, 1H), 4.63 (d, 1H, J=10.4 Hz), CH), 4.10–3.82 (m, 4H), 3.05, 3.04, 3.01 and 2.88 (four s, 6H), 2.30–2.20 (m, 1H), 1.43 and 1.41 (two s, 9H), 1.04 and 0.88 (two d, 6H, J=6.7 Hz); IR $(KBr)_{max}$ 3421, 2974, 1706, 1656, 1495, 1419, 1367, 1292, 1250, 1171, 1053, 953, 870, 837, 670 $cm^{-1}$.

From 2000:

A solution of 2000 (2.62 g, 5.85 mmol) in 40 mL of $CH_3OH$ was treated with 10% Pd—C (300 mg) and the resulting black suspension was stirred at 25° C. under $H_2$ (1 atm) for 16 h. The catalyst was removed by filtration through Celite and the filtrate was concentrated in vacuo to give 700 (2.14 g, 2.10 g theoretical, 100%) as a white foam: [ ]$^3$ –63.3 (c 1.1, $CHCl_3$); identical in all respects to the material above.

Benzyl L-Pipecolate (1100).

Method A: A solution of 900 (2.96 g, 12.9 mmol) in $CH_2Cl_2$ (60 mL) was treated sequentially with saturated aqueous $NaHCO_3$ (40 mL), $Bu_4NI$ (4.76 g, 12.9 mmol, 1.0 equiv) and benzyl bromide (3.31 g, 19.4 mmol, 1.5 equiv). The resulting mixture was stirred at 25° C. under $N_2$ for 24 h. The reaction mixture was extracted with $CH_2Cl_2$ (3×100 mL). The combined organic layers were dried ($Na_2SO_4$), filtered and concentrated in vacuo. Chromatography ($SiO_2$, 5×18 cm, 1:15 EtOAc-hexane eluent) afforded 1000 (3.71 g, 4.12 g theoretical, 90%) as a white solid: mp 51–53° C.; [ ]$^3$ –48 (c 3.4, $CHCl_3$); $R_f$=0.49 (10% EtAOc-hexane); $^1$H NMR revealed a 1:1 mixture of two conformers, $^1$H NMR ($CDCl_3$, 400 MHz) 7.32 (m, 5H), 5.21 (s, 2H), 4.94 (br s, 0.5H), 4.74 (br s, 0.5H), 4.01 (d, 0.5H, J=12.0 Hz), 3.90 (d, 0.5H, J=12.0 Hz), 2.91 (m, 1H), 2.22 (m, 1H), 1.70–1.10 (m, 5H), 1.44 (s, 4.5H), 1.36 (s, 4.5H); $^{13}$C NMR ($CDCl_3$, 100

MHz) 172.0, 171.8, 156.0, 155.4, 135.8, 128.5, 128.2, 128.1, 127.9, 79.9, 66.6, 54.9, 53.8, 42.1, 41.1, 28.3, 28.2, 26.7, 24.8, 24.5, 20.8, 20.6; IR (KBr)$_{max}$ 2941, 2861, 1734, 1700, 1454, 1364, 1340, 1246, 1154, 1091, 1045, 1002, 930, 873, 783, 752, 697 cm$^{-1}$; FABHRMS (NBA-NaI) m/z 342.1672 (M+Na$^+$, $C_{18}H_{25}NO_4$ requires 342.1681).

Method B: A solution of N-BOC-Pip-OH (900, 1.28 g, 5.6 mmol) and benzyl alcohol (1.05 g, 9.7 mmol, 1.7 equiv) in $CH_2Cl_2$ (20 mL) was cooled to −30° C. and sequentially treated with DMAP (68.3 mg, 0.56 mmol, 0.1 equiv) and DCC (1.16 g, 5.6 mmol, 1.0 equiv). The resulting mixture was stirred at −30° C. under Ar for 20 h. The white precipitate of DCU was removed by filtration and the filtrate was concentrated in vacuo. Chromatography ($SiO_2$, 4×16 cm, 1:15 EtOAc-hexane eluent) afforded 1000 (1.74 g, 1.79 g theoretical, 97%) as a white solid: mp 51–53° C.; [ ]$^3$ −46 (c 2.7, $CHCl_3$); identical in all respects to the material above.

A sample of 1000 (6.73 g, 21.1 mmol) in a 100 mL round-bottom flask was treated with 3M HCl-EtOAc (40 mL, 120 mmol, 5.7 equiv). The resulting mixture was stirred at 25° C. for 30 min. The volatiles were removed in vacuo. The residual HCl was further removed by adding $Et_2O$ (40 mL) to the hydrochloride salt of 1100 followed by its removal in vacuo. After repeating this procedure three times, 5.38 g of the hydrochloride salt of 1100 (5.39 g theoretical, 100%) was obtained. The hydrochloride salt of 1100 was neutralized with saturated aqueous $NaHCO_3$ (50 mL) and extracted with EtOAc (3×100 mL). The combined organic layers was dried ($Na_2SO_4$), filtered and concentrated in vacuo to give 1100 (4.62 g, 4.61 g theoretical, 100%) as white crystalline plates: mp 146–148° C.; [ ]$^3$ −23.3 (c 0.7, $CHCl_3$); $^1$H NMR ($CDCl_3$, 400 MHz) 7.33 (m, 5H), 5.24 (d, 1H, J=12.2 Hz), 5.18 (d, 1H, J=12.2 Hz), 3.97 (dd, 1H, J=4.0, 10.0 Hz), 3.56 (ddd, 1H, J=4.2, 4.5, 12.9 Hz), 3.06 (ddd, 1H, J=3.4, 10.1, 12.9 Hz), 2.27–2.21 (m, 1H), 2.15–2.06 (m, 1H), 2.01–1.97 (m, 1H), 1.84–1.73 (m, 2H), 1.60–1.52 (m, 1H); $^{13}$C NMR ($CDCl_3$, 100 MHz) 168.2, 134.6, 128.7, 128.6, 128.4, 68.0, 56.3, 43.7, 25.6, 21.6, 21.5; IR (KBr)$_{max}$ 3347, 2934, 2853, 1737, 1453, 1257, 1179, 1126, 1052, 749, 698 cm$^{-1}$; FABHRMS (NBA-NaI) m/z 220.1345 (M+H$^+$, $C_{13}H_{17}NO_2$ requires 220.1338).

N-SES-D-Ser-OBn (1200).

Solution of D-serine benzyl ester (4.38 g, 22.4 mmol) and $Et_3N$ (3.2 mL, 23.0 mmol) in 90 mL of degassed anhydrous DMF at −30° C. was treated slowly with trimethylethane-sulfonyl chloride (4.50 g, 22.4 mmol). The reaction mixture was stirred at −30° C. under Ar for 9 h and poured onto 100 mL of $H_2O$ and extracted with EtOAc (3×150 mL). The combined organic layers were washed with saturated aqueous NaCl (150 mL), dried ($Na_2SO_4$), filtered, and concentrated in vacuo. Flash chromatography ($SiO_2$, 5×20 cm, 20–40% EtOAc-hexane gradient) to afford 1200 (6.84 g, 8.05 g theoretical, 85%) as a colorless oil: [ ]$^3$ −2.2 (c 1.5, $CHCl_3$); $R_f$=0.48 ($SiO_2$, 50% EtOAc-hexane); $^1$H NMR ($CDCl_3$, 400 MHz) 7.35 (m, 5H), 5.41 (d, 1H, J=8.5 Hz), 5.22 (s, 2H), 4.24 (dt, 1H, J=11.2, 3.4 Hz), 4.00 (dd, 1H, J=11.2, 3.8 Hz), 3.93 (dd, 1H, J=11.2, 3.4 Hz), 3.00–2.90 (m, 2H), 1.10–0.98 (m, 2H), 0.01 (s, 9H); $^{13}$C NMR ($CDCl_3$, 50 MHz) 171.0, 135.5, 129.2, 129.1, 128.8, 68.1, 64.4, 58.4, 50.4, 10.5, −1.9; IR (neat)$_{max}$ 3504, 3288, 2954, 1742, 1498, 1330, 1252, 1174, 1130, 1070, 966, 894, 862, 842, 738, 698 cm$^{-1}$; FABHRMS (NBA) m/z 359.1220 ($C_{15}H_{25}NO_5SiS$ requires 359.1223).

N-SES-D-Ser-OH (1300).

A solution of 1200 (1.05 g, 2.91 mmol) in $CH_3OH$ (20 mL) was treated with 10% Pd—C (100 mg). The resulting black suspension solution was stirred under $H_2$ (1 atm) at 25° C. for 12 h. The catalyst was removed by filtration through Celite and filtrate was concentrated in vacuo to give 13 (785 mg, 784 mg theoretical, 100%) as a white solid: mp 61–63° C.; [ ]$^3$ −2.1 (c 2.2, $CHCl_3$); $^1$H NMR ($CDCl_3$, 400 MHz) 6.12 (d, 1H, J=8.7 Hz), 5.42 (br s, 2H), 4.20 (d, 1H, J=8.7 Hz), 4.11 (d, 1H, J=10.2 Hz), 3.92 (d, 1H, J=10.2 Hz), 3.05–2.96 (m, 2H), 1.10–0.98 (m, 2H), 0.04 (s, 9H); $^{13}$C NMR ($CDCl_3$, 100 MHz) 173.3, 64.2, 57.7, 50.2, 10.2; IR (KBr)$_{max}$ 3416, 3313, 2956, 1740, 1321, 1252, 1177, 1120, 1023, 843, 759, 741, 700 cm$^{-1}$; FABHRMS (NBA-NaI) m/z 292.0663 (M+Na$^+$, $C_8H_{19}NO_5SiS$ requires 292.0651).

Anal. Calcd for $C_8H_{19}NO_5SiS$: C, 35.67; H, 7.11; N, 5.20; S, 11.90. Found: C, 35.93; H, 6.96; N, 5.39; S, 12.24.

N-SES-D-Ser-Pip-OBn (1400).

A solution of 1100 (1.27 g, 5.77 mmol, 1.3 equiv) and 1300 (1.23 g, 4.58 mmol) in $CH_2Cl_2$ (20 mL) was cooled to 0° C. and sequentially treated with $Et_3N$ (1.90 mL, 13.6 mmol, 3.0 equiv) and bis(2-oxo-3-oxazolidinyl)-phosphinic chloride (BOP-Cl, 1.62 g, 6.36 mmol, 1.40 equiv) and the resulting reaction mixture was stirred at 0° C. for 10 h. The reaction mixture was diluted with $CH_2Cl_2$ (50 mL) and washed sequentially with 10% aqueous HCl (30 mL), $H_2O$ (30 mL), saturated aqueous $NaHCO_3$ (30 mL), and saturated aqueous NaCl (30 mL). The organic layer was dried ($Na_2SO_4$), filtered, and concentrated in vacuo. Flash chromatography ($SiO_2$, 4×16 cm, 40% EtOAc-hexane eluent) afforded 1400 (1.83 g, 2.15 g theoretical, 85%) as a white crystalline solid: mp 105–106° C.; $R_f$=0.35 (50% EtOAc-hexane); [ ]$^3$ −72 (c 1.1, $CH_2Cl_2$); $^1$H NMR ($CDCl_3$, 400 MHz) 7.39–7.31 (m, 5H), 5.55 (d, 1H, J=8.7 Hz), 5.30 (d, 1H, J=5.2 Hz), 5.20 (d, 1H, J=12.3 Hz), 5.09 (d, 1H, J=12.3 Hz), 4.50 (m, 1H), 3.79–3.68 (m, 2H), 3.30 (dt, 1H, J=3.0, 13.1 Hz), 2.95–2.87 (m, 2H), 2.66 (m, 1H), 2.31 (d, 1H, J=14.2 Hz), 1.76–1.18 (m, 6H), 1.06–0.98 (m, 2H), 0.03 (s, 9H); $^{13}$C NMR ($CDCl_3$, 100 MHz) 170.1, 169.9, 135.3, 128.6, 128.4, 128.0, 67.1, 64.3, 55.4, 53.0, 49.5, 43.6, 26.3, 25.0, 20.7, 10.1, −2.1; IR (KBr)$_{max}$ 3466, 3270, 2950, 2860, 1738, 1643, 1418, 1322, 1250, 1162, 1143, 1017, 843, 738, 698 cm$^{-1}$; FABHRMS (NBA) m/z 471.1985 (M$^+$+H, $C_{21}H_{34}N_2O_6SiS$ requires 471.1985).

Anal. Calcd for $C_{21}H_{34}N_2O_6SiS$: C, 53.59; H, 7.28; N, 5.95; S, 6.81. Found: C, 53.68; H, 7.19; N, 6.11; S, 6.83.

N-SES-D-Ser[Boc-Gly-Sar-NMe-Val]-Pip-OBn (1500).

A solution of 1400 (2.76 g, 5.85 mmol) and 700 (2.10 g, 5.86 mmol) in $CH_2Cl_2$ (40 mL) was cooled to 0° C. and sequentially treated with DMAP (0.71 g, 5.86 mmol, 1.0 equiv) and DCC (1.21 g, 5.86 mmol, 1.0 equiv) and the resulting reaction mixture was stirred at 0° C. for 24 h. The white precipitate that formed was removed by filtration and the filtrate was concentrated in vacuo. Flash chromatography ($SiO_2$, 4×16 cm, 50% EtOAc-hexane eluent) afforded 1500 which was separated into two isomers. The major isomer constitutes the desired product 1500 (3.75 g, 79%, typically 79–89%) and the minor isomer constitutes the Val-CH epimerized product (300 mg, 6%). For the major diastereomer 1500: white foam; mp 68–72° C.; $R_f$=0.44 (67% EtOAc-hexane); [ ]$^3$ −110 (c 2.0, $CHCl_3$); $^1$H NMR ($CDCl_3$, 400 MHz) 7.67 (d, 0.4 H, J=9.6 Hz), 7.34–7.27 (m, 5H), 5.69–5.49 (m, 1.6H), 5.29 and 5.22 (two d, 1H, J=6.7 Hz), 5.21–4.90 (m, 3H), 4.79 (d, 1H, J=10.7 Hz), 4.75–4.35 (m, 2H), 4.15–3.55 (m, 4H), 3.35–3.20 (m, 1H), 3.05–2.70 (four s and a set of multiplets, 8H), 2.32–2.15 (m, 2H), 1.75–1.15 (m, 15H), 1.05–0.82 (m and three d, 8H, J=6.4 Hz), −0.05 to −0.08 (several s, 9H); IR (KBr)$_{max}$ 3223, 2956, 1740, 1708, 1658, 1485, 1416, 1325, 1250, 1168, 1018, 841 cm$^{-1}$; FABHRMS (NBA) m/z 812.9362 (M$^+$+H, $C_{37}H_{61}N_5O_{11}SiS$ requires 812.3936).

Anal. Calcd for $C_{37}H_{61}N_5O_{11}SiS$: C, 54.72; H, 7.57; N, 8.62; S, 3.95. Found: C, 55.00; H, 7.65; N, 8.70; S, 4.13.

For the minor isomer: white foam; mp 72–76° C. $R_f$=0.35 (67% EtOAc-hexane); [ ]$^3$ –36 (c 0.15, CHCl$_3$); $^1$H NMR (CDCl$_3$, 400 MHz) 7.35–7.25 (m, 5H), 5.86 (d, 1H, J=9.2 Hz), 5.68–5.61 (m, 1H), 5.28–5.00 (m, 3H), 4.82 (d, 1H, J=10.8 Hz), 4.67 (m, 1H), 4.50–3.80 (m, 6H), 3.31 (m, 1H), 3.04–2.79 (two s and a set of multiplets, 8H), 2.32–2.15 (m, 2H), 1.80–1.35 (m, 15H), 1.05–0.83 (two d and m, 8H, J=6.7 Hz), 0.01 (s, 9H); IR (KBr)$_{max}$ 3421, 3237, 2962, 1741, 1657, 1325, 1250, 1167, 1051, 1017, 972, 842, 742, 700 cm$^{-1}$; FABHRMS (NBA-CsI) m/z 944.2922 (M+Cs$^+$, $C_{37}H_{61}N_5O_{11}SiS$ requires 944.2912).

N-SES-D-Ser[N-SES-D-Ser[(Boc-Gly-Sar-NMe-Val)-Pip-Gly-Sar-NMe-Val]-Pip-OBn (2100).

A solution of 1500 (1.62 g, 2.0 mmol) in CH$_3$OH (30 mL) was treated with 10% Pd—C (160 mg) and the resulting black suspension was stirred at 25° C. under H$_2$ (1 atm) for 12 h. The catalyst was removed by filtration through Celite and the filtrate was concentrated in vacuo to give the crude acid 1700 (1.45 g, 1.45 g theoretical, 100%) which was used directly in the next reaction without further purification.

Another 1.62 g sample of 1500 (2.0 mmol) was treated with 10 mL of 3M HCl-EtOAc and the mixture was stirred at 25° C. for 30 min. The volatiles were removed in vacuo. The residual HCl was removed by adding Et$_2$O (15 mL) to the hydrochloride salt 1600 followed by its removal in vacuo. After repeating this procedure three times, 1.50 g of 1600 (1.49 g theoretical, 100%) was obtained and used directly in the following reaction without further purification.

A solution of 1700 (1.45 g, 2.0 mmol) and the hydrochloride salt 1600 (1.50 g, 2.0 mmol) in DMF (10 mL) was treated sequentially with NaHCO$_3$ (675 mg, 8.0 mmol), HOBt (271 mg, 2.0 mmol), and EDCI (385 mg, 2.0 mmol) and the reaction mixture was stirred at 0° C. (2 h) and 25° C. (24 h). The reaction mixture was poured onto H$_2$O (20 mL) and extracted with EtOAc (3×40 mL). The combined organic phase was washed with saturated aqueous NaCl (20 mL), dried (Na$_2$SO$_4$), filtered and concentrated in vacuo. Flash chromatography (SiO$_2$, 2×16 cm, 80–100% EtOAc-CH$_2$Cl$_2$ gradient elution) afforded 2100 (2.28 g, 2.84 g theoretical, 80%) as a glassy solid; $R_f$=0.6 (5% CH$_3$CN-EtOAc); [ ]$^3$ –124 (c 0.9, CHCl$_3$); $^1$H NMR (CDCl$_3$, 400 MHz) 7.36–7.26 (m, 5H), 5.70–5.50 (m, 2H), 5.30–5.05 (m, 4H), 4.80–3.60 (m, 16H), 3.40–3.20 (m, 2H), 3.10–2.70 (m, 16H), 2.35–2.10 (m, 4H), 1.85–1.20 (m, 21H), 1.05–0.80 (two d and m, 16H, J=6.2 Hz and 6.5 Hz), 0.01 to –0.08 (m, 18H); IR (KBr)$_{max}$ 3240, 2954, 1740, 1655, 1482, 1456, 1415, 1318, 1287, 1250, 1169, 1021, 841, 739 cm$^{-1}$; FABHRMS (NBA-NaI) m/z 1437.6599 (M+Na$^+$, $C_{62}H_{106}N_{10}O_{19}Si_2S_2$ requires 1437.6531).

(N-SES-D-Ser-Pip-Gly-Sar-NMe-Val)$_2$ (Serine Hydroxyl) Dilactone (2400).

A solution of 2100 (1.69 g, 1.14 mmol) in CH$_3$OH (20 mL) was treated with 10% Pd—C (200 mg) and the black suspension was stirred at 25° C. under an atmosphere of H$_2$ (1 atm) for 16 h. The catalyst was removed by filtration through Celite and the filtrate was concentrated in vacuo to give crude 22 (1.47 g, 1.51 g theoretical, 97%). Crude 1900 was treated with 3M HCl-EtOAc (10 mL) and the mixture was stirred at 25° C. for 30 min. The volatiles were removed in vacuo and the excess HCl was removed by suspending the hydrochloride salt in Et$_2$O (30 mL) followed by its removal in vacuo. After repeating this procedure three times, 1.41 g (1.40 g theoretical, 100%) of the hydrochloride salt 2300 was obtained and used in the next step without further purification.

A solution of the hydrochloride salt 2300 (1.41 g, 1.11 mmol) in degassed DMF (370 mL) cooled to 0° C. and sequentially treated with NaHCO$_3$ (933 mg, 11.1 mmol, 10 equiv) and diphenyl phosphorazidate (DPPA, 0.86 mL, 4.45 mmol, 4.0 equiv) and the reaction mixture was stirred at 0° C. for 72 h. The mixture was concentrated in vacuo and the residue was diluted with EtOAc (100 mL). The organic phase was washed with 10% aqueous HCl (50 mL), H$_2$O (50 mL), saturated aqueous NaHCO$_3$ (50 mL) and saturated aqueous NaCl (50 mL), dried (Na$_2$SO$_4$), filtered and concentrated in vacuo. Flash chromatography (SiO$_2$, 2×16 cm, 10% CH$_3$CN-EtOAc eluent) afforded 2400 (1.21 g, 1.36 g theoretical, 89%, typically 85–90%) as a white powder: mp 185–188° C. (dec); $R_f$=0.5 (5% CH$_3$CN-EtOAc); [ ]$^3$ –88 (c 0.85, CHCl$_3$); $^1$H NMR (CDCl$_3$, 400 MHz) 8.38 (d, 2H, J=4.5 Hz, Gly-NH), 5.79 (d, 2H, J=6.7 Hz, D-Ser-NH), 5.30 (d, 2H, J=16.7 Hz, Sar- —CH), 5.25 (d, 2H, J=4.6 Hz, Pip- —CH), 4.78 (d, 2H, J=10.9 Hz, Val- —CH), 4.63 (d, 4H, J=8.6 Hz, D-Ser- —CH and —CH), 4.40 (d, 2H, J=10.4 Hz, D-Ser- —CH), 4.38 (dd, 2H, J=5.6, 18.0 Hz, Gly- —CH), 3.99 (d, 2H, J=18 Hz, Gly- —CH), 3.90 (dd, 2H, J=10.8, 12.6 Hz, Pip- —CH), 3.55 (d, 2H, J=13.4 Hz, Pip- —CH), 3.42 (d, 2H, J=16.7 Hz, Sar- —CH), 2.94 (s, 6H, NCH$_3$), 2.91 (s, 6H, NCH$_3$), 2.98–2.82 (m, 4H, SO$_2$CH$_2$), 2.16–2.07 (d split septet, 2H, J=10.3, 6.7 Hz, Val- —CH), 1.76–1.36 (m, 12H, Pip-(CH$_2$)$_3$), 1.04–0.94 (m, 4H, SO$_2$CH$_2$CH$_2$), 0.95 (d, 6H, J=6.7 Hz, Val- —CH$_3$), 0.84 (d, 6H, J=6.7 Hz, Val- —CH$_3$), 0.03 (s, 18H, SiMe$_3$); $^{13}$C NMR (CDCl$_3$, 100 MHz) 172.2, 169.3, 169.2, 167.7, 166.6, 65.2, 62.3, 53.7, 52,9, 49.5, 49.3, 44.0, 41.9, 35.0, 30.3, 28.4, 26.8, 24.6, 20.0, 19.3, 19.1, 10.2, –2.0; IR (KBr)$_{max}$ 3330, 2953, 2871, 1743, 1644, 1460, 1418, 1288, 1251, 1171, 1136, 1108, 844, 738, 699 cm$^{-1}$; FABHRMS (NBA-CsI) m/z 1207.5535 (M+H$^+$, $C_{50}H_{90}N_{10}O_{16}S_2Si_2$ requires 1207.5595).

(N-BOC-D-Ser-Pip-Gly-Sar-NMe-Val)$_2$ (Serine Hydroxyl) Dilactone (23).

A solution of 2400 (120 mg, 0.10 mmol) in THF (3 mL) was treated sequentially with (BOC)$_2$O (0.7 mL, 3.05 mmol, 30 equiv) and 1.0 M BU$_4$NF—THF (1.0 mL, 1.0 mmol, 10 equiv) and the resulting mixture was stirred at 25° C. for 48 h. The reaction mixture was diluted with EtOAc (30 mL), washed with H$_2$O (20 mL), saturated aqueous NaCl (20 mL), dried (Na$_2$SO$_4$), filtered, and concentrated in vacuo. Flash chromatography (SiO$_2$, 2×16 cm, 5% EtOH—CH$_2$Cl$_2$ eluent) afforded 23 (78 mg, 107 mg theoretical, 73%, 70–73%) as a white powder: mp 245–247° C. (EtOAc, plates); $R_f$=0.43 (10% CH$_3$CN-EtOAc); [ ]$^3$ –53 (c 0.15, CHCl$_3$); $^1$H NMR (CDCl$_3$, 400 MHz) Table 2; $^{13}$C NMR (CDCl$_3$, 100 MHz) 172.7, 169.31, 169.26, 167.7, 167.3, 155.1, 79.8, 63.4, 62.3, 52.6, 51.3, 49.2, 43.8, 41.8, 34.9, 30.4, 28.5, 28.4, 26.7, 24.7, 20.1, 19.5, 19.0; IR (KBr)$_{max}$ 3422, 3333, 2964, 2937, 2862, 1742, 1713, 1647, 1491, 1458, 1368, 1290, 1250, 1167, 1014, 849, 780 cm$^{-1}$; FABHRMS (NBA-CsI) m/z 1211.4985 (M+Cs$^+$, $C_{50}H_{82}N_{10}O_{16}$ requires 1211.4965).

The structure of 23 was established unambiguously in a single-crystal X-ray structure determination conducted on plates grown from EtOAc.

Sandramycin Bis-O-benzyl Ether (2700).

A solution 23 (48 mg, 0.044 mmol) in 3M HCl-EtOAc (2 mL) at 25° C. was stirred for 30 min. The solvent was removed in vacuo to afford the hydrochloride salt 25 (43.3 mg, 42.3 mg theoretical, 100%) as a white powder which was used directly in next reaction.

A solution of the hydrochloride salt 25 (43.3 mg, 0.044 mmol) and 2800 (50.0 mg, 0.179 mmol, 4.0 equiv) in DMF (4 mL) was treated sequentially with NaHCO$_3$ (37.5 mg, 0.45 mmol, 10.2 equiv), HOBt (36.2 mg, 0.268 mmol, 6.0 equiv), and EDCI (34.3 mg, 0.178 mmol, 4.0 equiv) and the reaction mixture was stirred at 25° C. for 72 h. The reaction mixture was diluted with EtOAc (20 mL) and washed with $H_2O$ (10 mL), saturated aqueous NaCl (10 mL), dried ($Na_2SO_4$), filtered, and concentrated in vacuo. Flash chromatography ($SiO_2$, 1×15 cm, 5% EtOH—$CH_2Cl_2$ eluent) afforded 27 (56.8 mg, 62.3 mg theoretical, 91%) as a white powder: mp 270–273° C.; $R_f$=0.42 (30% $CH_3CN$-EtOAc); [ ]$^3$ –107 (c. 0.29, CHCl$_3$); $^1H$ NMR (CDCl$_3$, 400 MHz) 9.01 (d, 2H, J=6.3 Hz), 8.48 (d, 2H, J=4.3 Hz), 7.92 (d, 2H, J=7.8 Hz), 7.70 (d, 2H, J=8.5 Hz), 7.59 (s, 2H), 7.54 (m, 8H), 7.39 (t, 4H, J=7.5 Hz), 7.30 (t, 2H, J=7.4 Hz), 5.46 (d, 2H, J=4.8 Hz), 5.44 (d, 2H, J=16.6 Hz), 5.34 (m, 6H), 4.87 (dd, 2H, J=2.0, 11.5 Hz), 4.83 (d, 2H, J=11 Hz), 4.58 (dd, 2H, J=2.0, 11.5 Hz), 4.42 (dd, 2H, J=5.7, 17.4 Hz), 4.03 (d, 2H, J=17.4 Hz), 4.01 (m, 2H), 3.76 (d, 2H, J=13.3 Hz), 3.47 (d, 2H, J=16.6 Hz), 3.08 (s, 6H), 2.92 (s, 6H), 2.05 (d split septet, 2H, J=11, 6.5 Hz), 1.80–1.40 (m, 12H), 0.95 (d, 6H, J=6.5 Hz), 0.81 (d, 6H, J=6.5 Hz); $^{13}C$ NMR (CDCl$_3$, 100 MHz) 172.7, 169.2, 167.8, 167.0, 163.5, 151.7, 142.6, 141.6, 136.0, 130.2, 129.5, 128.7, 128.4, 127.9, 127.5, 126.9, 126.4, 117.2, 70.7, 62.8, 62.3, 52.5, 50.8, 49.3, 43.8, 41.9, 34.9, 30.4, 29.7, 28.7, 26.5, 24.8, 20.2, 19.4, 19.0; IR (KBr)$_{max}$ 3366, 2934, 2862, 1744, 1641, 1492, 1456, 1420, 1344, 1323, 1287, 1256, 1215, 1184, 1133, 1092, 1010, 918, 841, 774, 733, 697 cm$^{-1}$; FABHRMS (NBA-CsI) m/z 1533.5490 (M+Cs$^+$, $C_{74}H_{88}N_{12}O_{16}$ requires 1533.5496).

Sandramycin (1).

A sample of 10% Pd—C (3 mg) was added to a solution of 2700 (6.2 mg, 0.0044 mmol) in EtOAc (4 mL) and the black suspension was stirred at 25° C. under an atmosphere of $H_2$ (1 atm) for 12 h. The catalyst was removed by filtration through Celite and the filtrate was concentrated in vacuo. Chromatography (SiO$_2$, 0.5×6 cm, EtOAc eluent) afforded 1 (4.2 mg, 5.4 mg theoretical, 78%) as a white powder identical in all respects with a sample of natural material: white powder, mp 206–209° C., lit$^1$ mp 208–212° C.; $R_f$=0.4 (SiO$_2$, 5% CH$_3$OH—CHCl$_3$), lit$^1$ $R_f$=0.4 (SiO$_2$, 5% CH$_3$OH—CHCl$_3$); [ ]$^3$ –153 (c 0.17, CHCl$_3$); $^1H$ NMR (CDCl$_3$, 400 MHz) 11.74 (s, 2H, OH), 9.56 (d, 2H, J=5.7 Hz, Ser-NH), 8.52 (d, 2H, J=4.4 Hz, Gly-NH), 7.81 (m, 2H, C5'—H), 7.71 (dd, 2H, J=4.4, 5.4 Hz, C8'—H), 7.63 (s, 2H, C4'—H), 7.50 (dd, 4H, J=4.1, 5.3 Hz, C6' and C7'—H), 5.57 (d, 2H, J=6.4 Hz, Pip- —CH), 5.54 (d, 2H, J=16.6 Hz, Sar- —CH), 5.26 (d, 2H, J=5.0 Hz, Ser- —CH), 4.99 (d, 2H, J=11.7 Hz, Ser- —CH), 4.87 (d, 2H, J=11.0 Hz, Val- —CH), 4.43 (d, 4H, J=11.7 Hz, Ser- —CH and Gly- —CH), 4.10 (m, 2H, Pip- —CH), 4.06 (m, 2H, Gly- —CH), 3.74 (d, J=14.5 Hz, Pip- —CH), 3.55 (d, 2H, J=16.6 Hz, Sar- —CH), 3.12 (s, 6H, Val-NCH$_3$), 2.94 (s, 6H, Sar-NCH$_3$), 2.04 (d split septet, 2H, J=11.0, 6.4 Hz, Val- —CH), 1.85–1.50 (m, 12H, Pip-(CH$_2$)$_3$), 0.92 (d, 6H, J=6.4 Hz, Val- —CH$_3$), 0.78 (d, 6H, J=6.4 Hz, Val- —CH$_3$); $^{13}C$ NMR (CDCl$_3$, 100 MHz) 172.6, 169.4, 169.2, 167.8, 167.7, 166.2, 153.8, 141.4, 134.6, 132.0, 129.4, 128.5, 127.1, 126.4, 120.3, 62.2, 61.9, 52.5, 50.6, 49.3, 43.9, 41.9, 34.9, 30.3, 28.8, 26.2, 24.9, 20.2, 19.4, 18.7; IR (KBr)$_{max}$ 3487, 3329, 2932, 1744, 1662, 1637, 1518, 1466, 1418, 1333, 1285, 1191, 1135, 1016, 887, 734 cm$^{-1}$; UV (CH$_3$OH)$_{max}$ 217 (62000), 229 (60000), 300 (8070), 356 nm (7840); lit$^1$ UV (CH$_3$OH)$_{max}$ 217 (63700), 229 (62800), 356 nm (8100); FABHRMS (NBA) m/z 1221.5565 (M+H$^+$, $C_{60}H_{76}N_{12}O_{16}$ requires 1221.5581).

$N^1$-SES,$N^6$-Boc-(D-Ser-Pip-Gly-Sar-NMe-Val)$_2$ (Serine Hydroxyl) Dilactone (2900).

A solution of 2400 (58.2 mg, 0.048 mmol) in 5 mL of THF was treated sequentially with (BOC)$_2$O (110 μL, 0.48 mmol, 10 equiv) and 1.0 M Bu$_4$NF in THF (192 μL, 0.192 mmol, 4 equiv). The mixture was stirred at 25° C. under N$_2$ for 24 h. The reaction mixture was diluted with 40 mL of EtOAc and washed with H$_2$O (20 mL) and saturated aqueous NaCl (20 mL). The organic layer was dried (Na$_2$SO$_4$), filtered, and concentrated in vacuo. Chromatography (SiO$_2$, 2×18 cm, 10% CH$_3$CN-EtOAc) gave 2900 (18.2 mg, 55.1 mg theoretical, 33%) as a white solid along with recovered 2400 (6.2 mg, 11%) and 23 (14 mg, 27%). For 2900: $R_f$=0.6 (30% CH$_3$CN-EtOAc); [ ]$^3$ –74 (c 0.4, CHCl$_3$); $^1H$ NMR (CDCl$_3$, 400 MHz) 8.43 (d, 1H, J=5.7 Hz), 8.42 (d, 1H, J=6.0 Hz), 5.84 (d, 1H, J=6.1 Hz), 5.80 (d, 1H, J=7.2 Hz), 5.35 (d, 1H, J=16.2 Hz), 5.31 (d, 1H, J=16.2 Hz), 5.26 (m, 2H), 4.83 (m, 1H), 4.80 (d, 1H, J=11.0 Hz), 4.79 (d, 1H, J=11.0 Hz), 4.66–4.60 (m, 2H), 4.48–4.30 (m, 5H), 4.02 (d, 1H, J=17.3 Hz), 4.00 (d, 1H, J=17.5 Hz), 3.91 (m, 2H), 3.62 (d, 1H, J=12.1 Hz), 3.55 (d, 1H, J=12.8 Hz), 3.42 (d, 2H, J=16.2 Hz), 2.95 (s, 3H), 2.94 (s, 3H), 2.92 (s, 3H), 2.91 (s, 3H), 2.93–2.83 (m, 2H), 2.16–2.10 (m, 2H), 1.70–1.40 (m, 12H), 1.43 (s, 9H), 1.05–0.94 (m, 2H), 0.98 (d, 3H, J=6.5 Hz), 0.97 (d, 3H, J=6.5 Hz), 0.85 (d, 3H, J=6.5 Hz), 0.84 (d, 3H, J=6.5 Hz), 0.03 (s, 9H); $^{13}C$ NMR (CDCl$_3$, 100 MHz) 172.7, 172.1, 169.4, 169.3, 169.2, 169.1, 167.7, 167.6, 167.3, 166.6, 155.0, 79.8, 65.2, 63.9, 62.3, 53.7, 52.9, 52.5, 51.2, 49.5, 49.2, 44.0, 43.8, 41.9, 41.8, 35.0, 34.9, 30.4, 30.3, 29.7, 29.6, 28.5, 28.4, 28.3, 26.8, 26.6, 24.7, 24.6, 20.0, 19.9, 19.4, 19.3, 19.1, 19.0, 10.2, –1.99; IR (KBr)$_{max}$ 3324, 2939, 1743, 1672, 1641, 1487, 1456, 1416, 1287, 1251, 1169, 1135, 1016, 849, 732 cm$^{-1}$; FABHRMS (NBA-CsI) m/z 1275.4716 (M+Cs$^+$, $C_{50}H_{86}N_{10}O_{16}$SiS: requires 1275.4768).

$N^1$-SES,$N^6$-(3-benzyloxyquinoline-2-carbonyl) (D-Ser-Pip-Gly-Sar-NMe-Val)$_2$ (Serine Hydroxyl) Dilactone (3100).

A solution of 2900 (17.5 mg, 0.015 mmol) in 3 M HCl-EtOAc (1 mL) at 25° C. was stirred for 30 min. The solvent was removed in vacuo to afford the hydrochloride salt 3000 (16.5 mg, 16.5 mg theoretical, 100%) as a white powder which was used directly in the next reaction.

A solution of the hydrochloride salt 3000 (16.5 mg, 0.015 mmol) and 2800 (17.1 mg, 0.06 mmol, 4 equiv) in DMF (1 mL) was treated sequentially with NaHCO$_3$ (14.0 mg, 0.16 mmol, 11 equiv), HOBt (13.1 mg, 0.97 mmol, 6.5 equiv), and EDCI (11.7 mg, 0.06 mmol, 4 equiv) and the reaction mixture was stirred at 25° C. for 48 h. The mixture was diluted with EtOAc (20 mL) and washed with H$_2$O (10 mL), saturated aqueous NaCl (10 mL), dried (Na$_2$SO$_4$), filtered, and concentrated in vacuo. Flash chromatography (SiO$_2$, 1×15 cm, 5% EtOH—CH$_2$Cl$_2$) afforded 3100 (12.6 mg, 20 mg theoretical, 63%) as a white powder: $R_f$ 0.51 (20% CH$_3$CN-EtOAc); [ ]$^3$ –84 (c 0.3, CHCl$_3$); $^1H$ NMR (CDCl$_3$, 400 MHz) 9.00 (d, 1H, J=6.3 Hz), 8.45 (d, 1H, J=5.7 Hz), 8.43 (d, 1H, J=5.7 Hz), 7.93 (d, 1H, J=7.5 Hz), 7.69 (d, 1H, J=7.6 Hz), 7.60 (s, 1H), 7.58–7.52 (m, 4H), 7.39 (m, 2H), 7.30 (m, 1H), 5.81 (d, 1H, J=7.0 Hz), 5.45 (d, 1H, J=16.6 Hz), 5.44 (d, 1H, J=5.8 Hz), 5.37–5.26 (m, 6H), 4.86 (dd, 1H, J=2.0, 12.0 Hz), 4.82 (d, 1H, J=11.0 Hz), 4.79 (d, 1H, J=11.0 Hz), 4.67–4.61 (m, 2H), 4.59 (dd, 1H, J=2.7, 12.0 Hz), 4.46–4.35 (m, 3H), 4.04–3.98 (m, 3H), 3.93–3.87 (m, 1H), 3.76 (d, 1H, J=13.3 Hz), 3.56 (d, 1H, J=14.3 Hz), 3.48 (d, 1H, J=16.6 Hz), 3.42 (d, 1H, J=16.6 Hz), 3.08 (s, 3H), 2.94 (s, 3H), 2.93 (s, 3H), 2.92 (s, 3H), 2.95–2.83 (m, 2H), 2.15–2.04 (m, 2H), 1.75–1.35 (m, 12H), 0.97 (d, 3H, J=6.6 Hz), 0.95 (d, 3H, J=6.6 Hz), 0.84 (d, 3H, J=6.6 Hz), 0.81 (d, 3H, J=6.6 Hz), 0.04 (s, 9H); $^{13}C$ NMR (CDCl$_3$, 100 MHz) 172.7, 172.1, 169.4, 169.2, 169.1, 167.8, 167.7, 167.0, 166.6, 163.5, 151.7, 142.6, 141.6, 136.0, 130.2, 129.5, 128.7, 128.4, 128.0, 127.5, 126.9, 126.4, 117.2, 70.9, 65.2, 62.8, 62.3, 62.2, 53.7, 53.0, 52.4, 50.7, 49.5, 49.3, 49.2, 44.0, 43.8, 41.9, 41.8, 35.0, 34.9, 30.4, 30.3, 29.7, 28.7, 28.4, 26.8, 26.5, 24.8, 24.6, 20.1, 20.0, 19.4, 19.3, 19.1, 19.0, 10.2, −2.0; IR (KBr)$_{max}$ 3322, 2936, 1742, 1668, 1639, 1491, 1462, 1285, 1255, 1135, 1015, 874, 734 cm$^{-1}$; FABHRMS (NBA-CsI) m/z 1436.6084 (M+Cs$^+$, $C_{62}H_{89}N_{11}O_{16}SiS$ requires 1436.5033).

$N^1$-SES,$N^6$-(3-hydroxylquinoline-2-carbonyl) (D-Ser-Pip-Gly-Sar-NMe-Val)$_2$ (Serine Hydroxyl) Dilactone (3200).

A solution of 3100 (10 mg, 0.0077 mmol) in 5 mL of EtOAc was treated with 10% Pd—C (4 mg) and the resulting black suspension was stirred at 25° C. under an atmosphere of H$_2$ (1 atm) for 14 h. The catalyst was removed by filtration through Celite and the filtrate was concentrated in vacuo. Flash chromatography (SiO$_2$ 1×10 cm, 10% CH$_3$CN-EtOAc) afforded 3200 (8.0 mg, 9.3 mg theoretical, 86%) as a white powder: R$_f$ 0.7 (20% CH$_3$CN-EtOAc); [ ]$^2$D$^3$ −105 (c 0.3, CHCl$_3$); $^1$H NMR (CDCl$_3$, 400 MHz) 11.74 (s, 1H, OH), 9.55 (d, 1H, J=6.4 Hz, Ser$^6$-NH), 8.50 (d, 1H, J=5.0 Hz, Gly$^8$-NH), 8.44 (d, 1H, J=5.0 Hz, Gly$^3$-NH), 7.81 (m, 1H, C5′—H), 7.70 (m, 1H, C8′—H), 7.63 (s, 1H, C4′—H), 7.50 (m, 2H, C6′ and C7′—H), 5.81 (d, 1H, J=7.0 Hz, Ser$^1$-NH), 5.55 (d, 1H, Sar$^9$- —CH), 5.54 (d, 1H, J=5.1 Hz, Pip$^7$- —CH), 5.30 (d, 1H, J=16.6 Hz, Sar$^4$- —CH), 5.28 (d, 1H, J=4.6 Hz, Pip$^2$- —CH), 5.25 (d, 1H, J=6.4 Hz, Ser$^6$- —CH), 4.98 (d, 1H, J=11.0 Hz, Ser$^6$- —CH), 4.86 (d, 1H, J=11.0 Hz, Val$^{10}$- —CH), 4.79 (d, 1H, J=11.0 Hz, Val$^5$- —CH), 4.64 (m, 2H, Ser$^1$- and —CH), 4.45–4.35 (m, 4H, Ser$^1$- —CH, Gly$^3$- —CH, Ser$^6$- —CH, and Gly$^8$- —CH), 4.10–3.99 (m, 3H, Gly$^3$- —CH, Gly$^8$- —CH, and Pip$^7$- —CH), 3.90 (m, 1H, Pip$^2$- —CH), 3.72 (d, 1H, J=13.0 Hz, Pip$^7$- —CH), 3.56 (d, 1H, J=13.0 Hz, Pip$^2$- —CH), 3.55 (d, 1H, J=16.6 Hz, Sar$^9$- —CH), 3.43 (d, 1H, J=16.6 Hz, Sar$^4$- —CH), 3.11 (s, 3H, Val$^{10}$-NCH$_3$), 2.95 (s, 3H, Val$^5$-NCH$_3$), 2.94 (s, 3H, Sar$^9$-NCH$_3$), 2.92 (s, 3H, Sar$^4$-NCH$_3$), 2.89 (m, 2H, SO$_2$CH$_2$), 2.12 (d split septet, 1H, J=11.0, 6.5 Hz, Val$^5$- —CH), 2.04 (d split septet, J=11.0, 6.5 Hz, Val$^{10}$- —CH), 1.85–1.45 (m, 12H, Pip$^2$- and Pip$^7$-(CH$_2$)$_3$), 1.01 (m, 2H, CH$_2$TMS), 0.97 (d, 3H, J=6.5 Hz, Val$^5$- —CH$_3$), 0.92 (d, 3H, J=6.5 Hz, Val$^{10}$- —CH$_3$), 0.85 (d, 3H, J=6.5 Hz, Val$^5$- —CH$_3$), 0.79 (d, 3H, J=6.5 Hz, Val$^{10}$- —CH$_3$), 0.05 (s, 9H, Si(CH$_3$)$_3$); $^{13}$C NMR (CDCl$_3$, 100 MHz) 172.6, 172.2, 169.4, 169.3, 169.2, 169.1, 167.8, 167.7, 167.6, 166.5, 166.2, 153.8, 141.5, 134.6, 132.1, 129.4, 128.5, 127.1, 126.4, 120.3, 65.2, 63.3, 62.2, 61.9, 53.7, 53.0, 52.4, 50.6, 49.5, 49.3, 49.2, 44.0, 43.9, 41.9, 41.8, 35.0, 34.9, 30.3, 30.2, 28.7, 28.5, 26.8, 26.2, 24.9, 24.6, 20.1, 20.0, 19.5, 19.3, 19.1, 18.7, 10.2, −2.0; IR (KBr)$_{max}$ 3329, 2936, 1744, 1639, 1518, 1462, 1413, 1287, 1255, 1135, 1015, 843, 754 cm$^{-1}$; UV (CH$_3$OH)$_{max}$ 202 (43000), 229 (30000), 300 (4000), 356 nm (3400); FABHRMS (NBA) m/z 1214.5671 (M+H$^+$, $C_{55}H_{83}N_{11}O_{16}SiS$ requires 1214.5588).

NMR Measurements.

All samples were degassed by six freeze-pump-thaw cycles and all spectra were recorded at 296° K. All 2D spectra were recorded with quadrature detection in both dimensions, TPPI[46] was used in F$_1$. The 2D spectra were processed and analyzed with the Felix program (version 2.3.0, BIOSYM Technologies) on a Silicon Graphics Personal IRIS Workstation. The parameters of the individual NMR experiments are given in the following experimentals.

(1) 1D $^1$H Spectrum. Pulse length: P1=5.0 μs; relaxation delay: d1=1.0 s; 128 acquisitions.

(2) 1D $^1$H—$^1$H Decoupling Spectrum (Homo-Decoupler Mode): Pulse length: P1=10.0 μs; relaxation delays: D1=1 s, D11=1 ms; the power set for the decoupled nucleus (DEC); dL0=50 dB; 64 acquisitions.

(3) 2D $^1$H—$^1$H NOESY Spectrum: D$_1$ −90°-t$_1$ 90°-$_{mix}$ 90°-t$_2$. Pulse length (90°): P1=18 μs; delays: d0=3 μs, d1=2 s, d8=450 ms; sweep width in F1 and F2: SWH=4424.779 Hz; 32 acquisitions; 512 increments.

(4) 2D $^1$H—$^1$H ROESY Spectrum: Sequence D$_1$ −90°-t$_1$ −90°-$_{mix}$ 90°-t$_2$. Pulse lengths: P1 (90° transmitter high power pulse)=18 μs; P15 (CW pulse for ROESY spinlock)=400 ms; delays: d0 (incremented delay)=3 μs, d1 (relaxation delay)=2 s, d12 (delay for power switching)=20 μs, d13 (short delay)=3 μs; powers: hl1 (ecoupler high power)=3 dB, hl4 (ecoupler low power)=17 dB; sweep width in F1 and F2: SWH=4424.79 Hz; 32 acquisitions; 512 increments.

DNA Binding Constant Measurements.

All fluorescence measurements were conducted on a JASCO FP-777 Spectrofluorometer equipped with a Fisons Haake D8 circulated water cooling system. The temperature was maintained at 24° C. throughout the experimental work. A 4 mL quartz cuvette equipped with a Teflon-coated magnetic stir bar was used in all experiments. Calf thymus DNA (Sigma) and dissolved in 10 mM Tris-HCl (pH 7.4) buffer solution containing 75 mM NaCl. The DNA concentration (320 μM in base-pair) was determined by UV ($_{260}$= 12824 M$^{-1}$ in base-pair). The excitation and emission spectra were recorded with a sample (2 mL) containing 10 mM Tris-HCl (pH 7.4), 75 mM NaCl buffer and 20 μL of a DMSO stock solution of agent with a 10 nm slit width in excitation and emission.

The final concentration for sandramycin, luzopeptin A, or 32 was 10 μM. For sandramycin (1), the fluorescence emission spectra exhibited a maximum at 530 nm and the excitation spectrum showed a sharp band at 260 nm and two broad bands at 300 nm and 360 nm, respectively. When excited at 360 nm, only the band at 530 nm was observed in the emission spectrum, and this excitation wavelength was chosen so that the absorbance of DNA would not interfere with that of agent. For the determination of the DNA binding constant of sandramycin (1), a 2 mL of sample containing 10 μM sandramycin (1) was titrated with 20 μL of calf thymus DNA (320 μM) solution. The quenching of fluorescence was measured 5 min after each addition of DNA to allow binding equilibration with 360 nm excitation and 530 nm fluorescence.

Similar titrations of solutions of luzopeptin A (10 μM) and 32 (10 μM) with calf thymus DNA (320 μM) were conducted with 340 nm excitation/520 nm fluorescence and 400 nm excitation/510 nm fluorescence, respectively.

DNA Binding Constant Determination for 23. Method A: Calf thymus DNA (1.0×10$^{-5}$ M in base-pair) was mixed with ethidium bromide (5.0×10$^{-6}$ M) resulting in a 2:1 ratio of base-pair:ethidium in a 10 mM Tris-HCl (pH 7.4), 75 mM NaCl buffer solution (2 mL). The fluorescence was calibrated at 24° C. to 100% F and 0% F with a DNA-ethidium buffer solution and ethidium buffer solution, respectively. The premixed DNA-ethidium solution was titrated with small aliquots of 23 (20 to 40 μL of 3 mM 25 in DMSO) and incubated at 24° C. for 30 min prior to each fluorescence measurement. The fluorescence was measured with 545 nm excitation and 595 nm emission with a slit width of 10 nm. The absolute binding constant from three such titrations were determined at 50% ethidium bromide displacement as measured by a drop in fluorescence to 50%. The binding constant of ethidium bromide employed to calculate the absolute binding constant with a competitive or noncompetitive binding model[39] was 4.5×10$^5$ M$^{-1}$ and the results are summarized in Table 4.

Method B:

A 2 mL of sample containing 400 μL of calf thymus DNA (320 μM in base-pair) with or without the presence of 40 μL of 23 (3.2×10$^{-3}$ M in DMSO) in 10 mM Tris-HCl (pH 7.4), 75 mM NaCl buffer solution was titrated with small aliquots of sandramycin (1 μL, 1.0×10$^{-3}$ M in DMSO). The quenching of fluorescence was measured 5 min after each addition of sandramycin with 360 nm excitation and 530 nm fluorescence.

General Procedure for Agarose Gel Electrophoresis.

Due to the low solubility of the agents in water, all agents were dissolved in DMSO as stock solutions, stored at −20° C. in the dark, and were diluted to the working concentrations in DMSO prior to addition to the DNA solution. A buffered DNA solution containing 0.25 μg of supercoiled X174 RF I DNA (1.0×10$^{-8}$ M) in 9 μL 50 mM Tris-HCl buffer solution (pH 8) was treated with 1 μL of agent in DMSO (the control DNA was treated with 1 μL of DMSO). The [agent] to [DNA] base-pair ratios were 0.022 (lane 1), 0.033 (2), 0.044 (3), 0.11 (4), 0.22 (5) for luzopeptin A, 0 (6 control DNA), 0.011 (7), 0.022 (8), 0.033 (9), 0.044 (10), 0.066 (11), 0.11 (12) for sandramycin in gel 5A; 0.011 (1), 0.033 (2), 0.066 (3), 0.11 (4) for sandramycin, 0 (5, control DNA), 0.022 (6), 0.11 (7), 0.22 (8), 0.44 (9), 0.88 (10), 1.74 (11), 2.2 (12) for compound 32 in gel 5B. The reactions were incubated at 25° C. for 1 h and 5 h for gel A and B, respectively, and quenched with 5 μL of loading buffer formed by mixing Keller buffer (0.4 M Tris-HCl, 0.05 M NaOAc, 0.0125 M EDTA, pH 7.9) with glycerol (40%), sodium dodecyl sulfate (0.4%), and bromophenol blue (0.3%). Electrophoresis was conducted on a 0.9% agarose gel at 90V for 3 h. The gel was stained with 0.1 μg/mL ethidium bromide, visualized on a UV transilluminator and photographed using Polaroid T667 black and white instant film and directly recorded on a Millipore Biolmage 60S RFLP system.

DNase I Footprinting.

The DNase I footprinting system was obtained from BRL (Life Technologies, Inc.). The $^{32}$P 5'-end-labeled w794 DNA was prepared as previously described.[43] Stock solutions of sandramycin were prepared in DMSO. The solutions were stored in the dark at −20° C. and were diluted to working conditions with buffer (10 mM Tris-HCl, pH 7.0; 10 mM KCl; 10 mM MgCl$_2$; 5 mM CaCl$_2$) immediately prior to use. The final concentration of DMSO did not exceed 2%.[6b] A buffered DNA solution (7 μL) containing the $^{32}$P 5'-end-labeled w794 DNA (5,000 cpm) in 10 mM Tri-HCl (pH 7.0), 10 mM KCl, 10 mM MgCl$_2$, and 5 mM CaCl$_2$ was treated with 2 μL of a freshly prepared sandramycin solution and H$_2$O (1 μL). The final concentrations of sandramycin were 2 μM, 10 μM, and 20 μM as indicated. The DNA reaction solutions were incubated at 25° C. for 30 min. The DNA cleavage reactions were initiated by the addition of 1 μL a stock solution of DNase I (0.1 μg/mL) containing 1 mM of dithiothreitol and allowed to proceed for 1 min at 25° C. The reactions were stopped by addition of 3 M NH$_4$OAc containing 250 mM EDTA followed by EtOH precipitation and isolation of the DNA. The DNA was resuspended in 8 μL of TE buffer, and formamide dye (6 μL) was added to the supernatant. Prior to electrophoresis, the samples were warmed at 100° C. for 5 min, placed in an ice bath, and centrifuged and the supernatant was loaded onto the gel. Sanger dideoxynucleotide sequencing reactions were run as standards adjacent to the treated DNA. Gel electrophoresis was conducted using a denaturing 8% sequencing gel (19:1 acrylamide-N,N-methylenebisacrylamide, 8 M urea). Formamide dye contained xylene cyanol FF (0.03%), bromophenol blue (0.3%), and aqueous Na$_2$EDTA (8.7%, 250 mM). Electrophoresis running buffer (TBE) contained Tris base (100 mM), boric acid (100 mM), and Na$_2$EDTA-H$_2$O (0.2 mM). The gel was prerun for 30 min with formamide dye prior to loading the samples. Autoradiography of the dried gel was carried out at −78° C. using Kodak X-Omat AR film and a Picker Spectra intensifying screen.

DNA Binding Studies. Analog Solution Preparation:

The analogs were dissolved in DMOS to a concentration of 1(10$^{-3}$ M. These solutions were stored under Ar at −78° C. and the integrity of the agents was checked periodically by $^1$H NMR in 10% DMSO-d$_6$/CDCl$_3$. In most cases, a final cuvette concentration of 1 (10$^{-5}$ M in a 2 mL aqueous buffer containing 10 mM NaCl, 75 mM Tris-HCl (pH 7.4) was achieved by adding 20 L of the analog solution to the buffer. An additional 20 L DMSO was added to promote dissolution of the analogs in the aqueous buffer.

Calf Thymus DNA:

Type I calf thymus DNA (Sigma) was dissolved in aqueous buffer containing 10 mM NaCl, 75 mM Tris-HCl (pH 7.4). The concentration in base-pairs, was obtained by UV spectroscopy at 24° C. based on a base-pair extinction coefficient of 12824 M$^{-1}$ cm$^{-1}$ at 260 nm. The purity was checked by assuring that the absorbance ratio at 260:280 nm was greater than 1.8 (Dienes et al. *Bioorg. Med. Chem. Lett.* 1995, 5, 547; Maniatis et al. *Mol. Cloning: A Laboratory Manual*; Cold Spring Harbor: N.Y., 1982; pp. 468–469).

Deoxyoligonucleotides:

The following self-complementary deoxyoligonucleotides: 5'-d(GCATGC)$_2$, 5'-d(GCTAGC)$_2$, 5'-d(GCGCGC)$_2$, 5'-d(GCCGGC)$_2$, and 5'-d(CGTACG)$_2$, were prepared on-site (The Scripps Research Institute Core Facility) or by Biosource Intl (Camarillo, Calif.) and were purified by isopropanol precipitation. Quantitation of the DNA concentration was established by UV absorbance (260 nm) of the single-strand DNA (75° C.) and the concentrations were established using the calculated extinction coefficients of 55200, 55800, 51000, 51600, and 57600 M$^{-1}$cm$^{-1}$, respectively (Richards, E. G. *In Handbook of Biochemistry and Molecular Biology: Nucleic Acids*; Fasman, G. D., Ed.; CRC: Cleveland, 3rd ed., 1975; Vol. 1, 597. Borer, P. N. *In Handbook of Biochemistry and Molecular Biology: Nucleic Acids*; Fasman, G. D., Ed.; CRC: Cleveland, 3rd ed., 1975; Vol. 1, 589). The results for 5'-d(GCATGC)$_2$ were compared with concentrations established by $^1$H NMR where the thymine methyl signal was integrated against an internal standard of deuterated trimethylsilyl sodium propionate. Concentrations obtained by both methods were in agreement.

DNA Binding Constant Measurements by Fluorescence Quenching.

A 20 L aliquot of a 1 mM DMSO solution of the agent was added to 1960 L of aqueous buffer (10 mM Tris-HCl, pH 7.4, 75 mM NaCl) in a 4 mL quartz cuvette equipped with a Teflon coated stir bar to achieve a final concentration of 10 M. An additional 20 L of DMSO was added to the cuvette to increase solubility of the agent and the solutions were shielded from light. After 5 min of stirring, an initial fluorescence reading was taken with minimum exposure to the excitation beam. At this point, aliquots of the DNA solution (5–30 L depending on amount necessary to maximize titration points in the high affinity binding region of the Scatchard plot) were added and the solution was allowed to equilibrate 15 min before the subsequent readings were taken. The excitation and emission wavelengths used for each analog varied and can be found in FIG. 6. The results of the titration were analyzed by Scatchard analysis. The linear portion of the Scatchard plot was used to determine the high affinity binding constants. In the case of the deoxyoligonucleotide study, a non-linear fit of the curve as described in the text was also used to determine the high affinity binding constant (Feldman, H. A. *Anal. Biochem.* 1972, 48, 317).

Inhibition of HIV-1 Reverse Transcriptase.

The assay was performed according to an available procedure (Goldman, M. E.; Salituro, G. S.; Bowen, J. A.; Williamson, J. M.; Zink, D. L.; Schleif, W. A.; Emini, E. A. *Mol. Pharmacol.* 1990, 38, 20) with slight modification. A 45 L solution of reaction buffer containing 55 mM Tris·HCl, pH 8.2, 80 mM potassium chloride, 12 mM $MgCl_2$, 1 mM DTT, 50 M EGTA, 2.5 g/mL rA·dT, 0.5 Ci of [$^3$H]TTP, 10 M TTP, 1 mg/mL BSA, and 0.01% Triton X-100 was added to a well in a filter cluster plate (Millipore MAHV N45). The reverse transcription reaction was initiated upon addition of the reverse transcriptase (1 unit; 1 unit=10 pmol of [$^3$H]TMP incorporated/60 min at 37° C.). The plate was incubated at 37° C. for 90 min. The plate was then placed on ice and 200 L of 13% trichloroacetic acid and 10 mM sodium pyrophosphate was added to each well. The plate was chilled for 2 h and the liquid vacuumed out through the filter using a Millipore manifold (Millipore MAVM 09601). The precipitate was washed with 1 M and 10 mM sodium pyrophosphate twice. The filter was punched out and placed in a scintillation vial. 4 mL of cocktail was added. Radioactivity was determined by liquid scintillation counting.

The effects of sandramycin and its analogs on HIV-1 reverse transcriptase were determined by incubating the agents and the rA·dT containing buffer at 25° C. for 30 min prior to addition of the reverse transcriptase. Reactions containing no agents were used as controls, and those lacking the transcriptase were used as blanks.

Preparation of Liposomes Encapsulating Beneficial Compounds for Treating Melanoma, and Liposome Compositions A beneficial liposome composition of the invention is typically provided in one or more of a variety of compositional forms suitable for the contemplated use. Although proteins, nucleic acids or other compounds for use in a liposome generally retain biological activity in a variety of buffers and solutions, it is preferred to be formulated in a phospholipid composition. Particularly preferred are phospholipid compositions which afford maximum stability and biological activity of the beneficial compound in the composition. Such phospholipid compositions are preferably formulated to form liposome compositions, as are generally well known in the art. Typically, the composition contains an amount of biologically active beneficial compound suitable for its contemplated use.

The preparation of liposomes, and their use in drug therapy has been previously described. See, for example, U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference. Exemplary methods for the entrapment of nucleic acids into liposomes is described in U.S. Pat. No. 5,223,263.

Preferred and exemplary methods for preparing beneficial compound-encapsulated liposomes for use in the present methods are described in the Examples. In particular, the encapsulation of melanin, protein or nucleic acid, each for delivery to hair follicles as a beneficial compound, are described herein.

The liposome compositions of the present invention typically comprise about 0.1 mg to about 3 mg of sandramycin analog, or about 0.1 ug to about 0.5 mg sandramycin analog, per mg of phospholipid mixture.

The ratio of active compound to phospholipid mixture may determine the sensitivity of the resulting reagent. Thus, use of a ratio of about 1 to 2 mg sandramycin analog per mg—also phospholipid mixture may be suitable for a protein reagent having a International Sensitivity Index ("ISI") of about 1.0. Use of a ratio of about 0.25 to about 0.5 mg protein per mg phospholipid mixture may be suitable to prepare a composition having an ISI of about 1.6 to about 2.0.

Preferred are compositions that additionally comprise from about 0.5 to about 1.5% (w/v) glycine. Where it is desired to be able to lyophilize the liposome composition to allow storage and later reconstitution, the reagent preferably includes a cryopreservative, preferably a carbohydrate preservative, most preferably trehalose.

The lipid bilayer of the liposomes comprises phospholipids, preferably, phosphoglycerides. Exemplary liposome compositions include phosphatidylcholine (PC) liposomes, particularly egg PC (EPC) and dipalmitoyl PC (DPPC). Additional candidate liposome compositions are prepared according to the teachings of U.S. Pat. No. 4,394,488, the teachings of which are incorporated by reference, particularly the descriptions of liposomes comprising phosphotidylethanolamine (PE), phosphotidylserine (PS), sphingolipids, phosphotidylglycerol (PG), phosphatidic acid (PA), cholesterol, spingomyelin cardiolipin, various cationicphospholipids glycolipids, gangliosides, cerebrosides and the like, used either singularly or in combination.

"Phospholipid" refers to an organic molecule derived from either glycerol (most commonly) or sphingosine. Phospholipids derived from glycerol (or phosphoglycerides) comprise a glycerol backbone, two fatty acid chains esterified to the first and second carbons of the glycerol and phosphoric acid esterified to the third carbon. Optionally, an alcohol moiety is esterified to the phosphoric acid.

Suitable phospholipids for use in the liposome compositions of the present invention include those which contain fatty acids having twelve to twenty carbon atoms; said fatty acids may be either saturated or unsaturated. The phospholipids may come from any natural source and the phospholipids, as such, may be comprised of molecules with differing fatty acids. Phospholipid mixtures comprising phospholipids from different sources may be used. For example, PC, PG and PE may be obtained from egg yolk; PS may be obtained from animal brain or spinal chord. These phospholipids may come from synthetic sources as well.

Phospholipid (PL) mixtures having a varied ratio of individual PLs may be used. However, although the phospholipids may be used in varied ratios, mixtures of phospholipids having preselected amounts of individual phospholipids result in liposome compositions having advantageous activity and stability of activity. Thus although a wide range of ratios of individual phospholipids may be used, for advantageous activity and stability of the resulting liposome composition, certain phospholipid compositions are preferred.

The phospholipids are conveniently combined in the appropriate ratios to provide the PL mixture for use in preparing the liposome composition of the present invention.

Liposomes are preferably prepared using one or more phospolipids including (N-(1-(2,3-dioleolyoxy)propyl)-N, N,N-trimehtyl ammonium chloride) (DOTMA), dioleoylphosphatidylethanolamine (DOPE), dioleoylphosphatidylcholine (DOPC), phosphatidylethanolamine (PE), egg PC (EPC), phosphatidylcholine (PC), dipalmitoyl PC (DPPC), cholesterol and the like phospholipids. Phospholipids can be obtained from a variety of sources, including Avanti (Birmingham, Ala.), GIBCO BRL (Gaithersburg, Md.) and Aldrich (Milwaulkee, Wis.), or can be prepared from available materials, as is well known.

Preferred liposomes comprise PC, EPC, or DPPC homogeneously. Further preferred liposome compositions comprise a combination of a PC-type phospholipid (such as PC, EPC, DOPC, DPPC and the like) combined with a PE-type phospholipid (PE, DOPE and the like) in a molar ratio of from about 2:5 to about 5:2, more preferably about 5:2 PC:PE. A preferred liposome composition comprises PC:PE:Chol in a molar ratio of 5:2:3.

A preferred liposome for use in the present invention additionally includes cationic phospholipids. One preferred cationic phospholipid is a monocationic phospholipid having two identical alkyl side chains.

Preferred cationic phospholipids are also generally available from a variety of sources, including the above recited sources. Particularly preferred cationic phospholipids include cationic phospholipids such as D282, D378, D383, D3886, D3897 and D3899, obtainable from Molecular Probes (Eugene, Oreg.), the structure and synthesis of which is well known and described in Handbook of Fluorescent Probes and Research Chemicals, ed. by R.P. Haugland, Molecular Probes, publisher, Eugene, Oreg. (1989–1991, and 1992–1993). The structures of cationic phospholipids D282, D378, D383, D3886, D3897 and D3899 are shown in FIG. 8.

D282 is also known as 1,1'-dioctadecyl-3,3,3',3'-tetramethylindocarbocyanine perchlorate; D378 is also known as 3,3'-diheptyloxacarbocyanine iodide; D383 is also known as 1,1'-didodecyl-3,3,3',3'-tetramethylindocarbocyanine perchlorate; D3886 is also known as 1,1'-dioleyl-3,3,3',3'-tetramethylindocarbocyanine methanesulfonate; D3897 is also known as N-4-(4-dilinoleylaminostyryl)-N-methylpyridinium iodide; and D3899 is also known as 1,1-dilinoleyl-3,3,3',3'-tetramethylindocarbocyanine perchlorate.

In one embodiment, the liposome composition of this invention contains one or more of the above cationic phospholipids. Preferably, a liposome composition of this invention comprises a formulation of phospholipids comprising a mixture of (a) one or more of the phospholipidis PC, EPC, DOPC, DPPC, PE, DOPE, cholesterol and the like phospholipids, and (b) one or more of the cationic phospholipids D282, D378, D383, D3886, D3897, D3899 and the like. A particularly preferred liposome composition comprises a mixture of phospholipid (a) and cationic phospholipid (b) in a ratio of about 0.5 to 2.0 moles of phospholipid (a) to about 0.5 to 1.5 moles of phospholipid (b), and more preferably about 1.0–1.2 moles of phospholipid (a) to 0.8 moles of cationic phospholipid (b). A preferred phospholipid composition in this embodiment comprises a mixture of DOPC or DOPE with one or more of the above cationic phospholipids in a ratio of about 0.8 moles to about 1.0–1.2 moles.

In another embodiment, the invention comprises a liposome composition comprising one or more phospholipids selected from the group consisting of PC, EPC, DOPC, DPPC, PE, DOPE and cholesterol, combined with one or more phospholipids to form pH-sensitive liposomes. pH-sensitive liposomes are generally well known and their preparation has been described by Straubinger et al., FEBS Letts., 179:148–154 (1985). A preferred pH sensitive liposome comprises oleic acid (OA) and PE at a mole ratio of 3:7. OA is available from a variety of commercial sources, including Sigma (St. Louis, Mo.).

The preferential targetting of a liposome composition of this invention to the skin can be optimized by the choice of phospholipids in the liposome composition, and may depend additionally on the included beneficial compound.

Particularly preferred parameters for targeting beneficial compounds to skin include the combined use of liposomes that have both cationic lipids and are pH-sensitive.

Where the liposome composition will be lyophilized prior to storage for later use, it is preferred to include a carbohydrate or carbohydrates as cryopreservative(s) to protect the integrity of liposomes in the resulting liposome composition during lyophilization and subsequent rehydration.

Cryopreservation relates to preserving the integrity of delicate substances when liquids containing them are frozen and dehydrated. The use of a carbohydrate as a cryopreservative of liposome integrity upon freezing and subsequent lyophilization has been reported. Racker, E., Membrane Biol., 10: 221–235 (1972); Sreter, F. et al., Biochim. Biophys. Acta., 203: 254–257 (1970); Crowe et al., Biochem. J., 242: 1–10 (1987); Crowe et al., Biochim. Biophys. Acta., 987: 367–384 (1988).

Suitable carbohydrate cryopreservatives include trehalose, maltose, lactose, glucose and mannitol. According to a preferred aspect of the present invention, trehalose is included in aqueous buffer solution used in the preparation of a liposome composition of the present invention (prior to lyophilization), preferably at a concentration in the range of about 50 mM to about 250 mM.

The phospholipids, which may be obtained from the manufacturer in an organic solvent, are mixed together in the appropriate ratios to yield the specified composition. An antioxidant can also be added to reduce alkyl chain peroxidation of the fatty acid portions of the phospholipids, and the organic solvent, if present, is removed by evaporation. One suitable antioxidant is butyrated hydroxy toluene. Preferably about 0.1% (by weight) of antioxidant is used.

The dried (evaporated) phospholipid mixture is then redissolved with an aqueous detergent solution. Suitable detergents include those which have a relatively high critical micelle concentration (CMC). Womack et al., Biochim. Biophys. Acta, 733: 210 (1983). Such detergents include detergents having a CMC of greater than approximately 2 mM. Preferred are those detergents having a CMC of between approximately 2 to 25 mM. Such preferred detergents include 3-[(3-cholamidopropyl)-dimethylammonio]-1-propanesulfonate (CHAPS) and alkylglucopyranosides such as octyl beta-D-glucopyranoside, octyl beta-D-thioglucopyranoside and the like. Optionally, the detergent solution may include other components. These components may include buffer salts such as HEPES, Tris, phosphate, and the like; various other salts such as NaCl, KCl, and the like; a carbohydrate cryopreservative such as trehalose, maltose, glucose, and the like; and glycine.

According to a preferred embodiment of the present invention, the detergent solution comprises 20 mM Tris, pH 7.5, 150 mM NaCl, (TBS) containing 100 mM CHAPS, 150 mM trehalose and 0.8% glycine. According to this preferred embodiment, the phospholipids are redissolved in this solution to give a final concentration of about 20 mg/ml.

Sandramycin analogs for use in a liposome, together with carrier protein, are combined with the redissolved phospholipids and the volume of the resulting mixture is adjusted with a buffer as described above, preferably containing cryopreservative (most preferably trehalose) and glycine but no detergent. Sandramycin analog is admixed with carrier protein, such as bovine gamma globulin, and sufficient buffer is added to adjust the final concentrations of active protein to 10 mg/ml, bovine gamma globulin to 1 mg/ml, phospholipid to 4 mg/ml and detergent to 20 mM. Suitable buffers include TBS containing 150 mm trehalose and 0.8% glycine.

The resulting clear, colorless solution requires no vortexing or sonicating to ensure co-solubilization.

The detergent in the phospholipid admixture can be removed by a number of methods resulting in a stable liposome composition having a sandraymicin analgog associated with and inserted through the lipid bilayer. Suitable methods of removal of detergent include dialysis, tangential flow diafiltration, cross flow hollow fiber filtration, treatment with hydrophobic chromatography resin, and simple dilution.

One preferred method of detergent removal from the phospholipid admixture utilizes dialysis for at least 30 hours at room temperature in dialysis membrane tubing against a buffer such as TBS containing 150 mM trehalose, 0.8% glycine and 0.05% $NaN_3$ to remove the detergent. Another preferred method of detergent removal utilizes resin treatment. Suitable resins include hydrophobic chromatographic resins such as Amberlite XAD-2 (Rohm and Haas Co. in Philadelphia, Pa.) or Bio-Beads SM-2 (BioRad in Richmond, Calif.). The resins may be used to remove the detergent, either by direct contact with the phospholipid solution admixture or separated from it by a dialysis membrane. The rate of removal of detergent from the phospholipid admixture is proportional to the weight ratio of the detergent in solution and the chromatographic resin beads.

The liposome solution resulting from the detergent removal step is then made to 5 mM $CaCl_2$. According to one preferred aspect, the liposome composition which contains the fully active compound is diluted to a concentration of 50 mM Tris, pH 7.5, 75 mM trehalose, 0.8% glycine and 10 to 15 mM $CaCl_2$ before use. Alternatively, the diluted reagent may be lyophilized for long term preservation of its biological performance characteristics and then later reconstituted by suspension in water before use.

Another preferred method of detergent removal avoids the use of either dialysis or resin treatment and yet provides for preparation of active reagent. According to this method, detergent solubilized phospholipid compositions containing protein or nucleic acids are diluted into a buffer without detergent to produce mixed micelles containing the beneficial compound which remain capable of being fully activated by $CaCl_2$. According to this aspect of the invention, phospholipids are dissolved to 20 mg/ml in a buffer containing detergent, preferably an alkyl glucopyranoside. A suitable buffer-detergent solution comprises 20 mM HEPES (pH 6) containing 50 mM octyl beta-D-thioglucopyranoside (OTG) and 150 mM NaCl. Carrier protein, active analog, and $CaCl_2$ are then added and the mixture diluted further with buffer without detergent, such as 20 mM HEPES (pH 6) containing 150 mM NaCl, to yield final concentrations of active analog at about 10 mg/ml, carrier protein (bovine gamma globulin) at 1 mg/ml, $CaCl_2$ at 5mM, phospholipids at 4 mg/ml, and OTG at 10 mM. The reagent may be lyophilized for storage as described above, or diluted as described above before use.

According to another aspect of the present invention, this reagent may be prepared by following methods for the preparation of vesicles and detergent-phospholipid mixed micelles from phospholipids by methods based on mechanical means, by removal of organic solvents, by detergent removal, and by size transformation as has been described by Lichtenberg, D. and Barenholz, Y., Methods of Biochemical Analysis, 33: 337–462 (1988), and the disclosures of which are incorporated herein by reference.

Incorporation of a beneficial compound is conducted by incorporation of the compound in the liposome either during liposome formation, or after formation by combining the liposome with the compound. Methods of introducing the compound into the liposome can vary, and are not intended to be limiting. Preferred methods are described in the Examples above.

What is claimed is:

1. A sandramycin analog represented by the following structure:

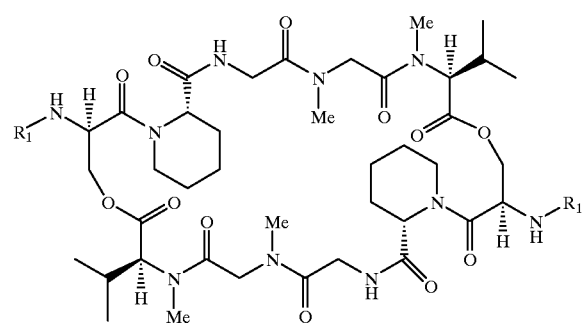

wherein $R_1$ is a radical selected from a group consisting of one of the following structures:

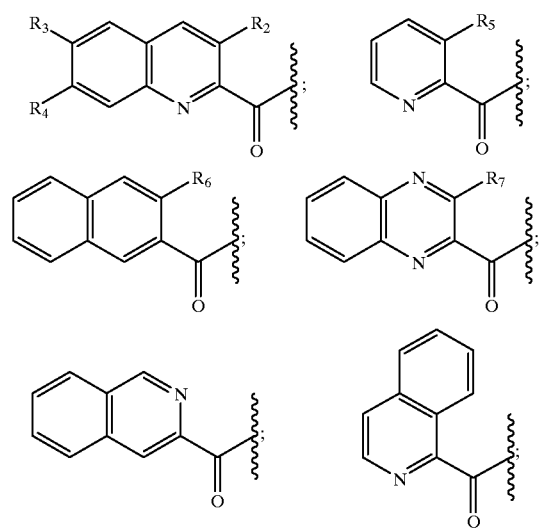

wherein $R_2$ is a radical selected from a group consisting of hydrogen, —OH, —OBenzyl, and —OMethyl; $R_3$ is a radical selected from a group consisting of hydrogen, —OMethyl, and Methyl; $R_4$ is a radical selected from a group consisting of hydrogen, and —Cl; $R_5$ is a radical selected from a group consisting of hydrogen, —OH, -and O-Benzyl; $R_6$ is a radical selected from a group consisting of hydrogen, —OH, -and O-Benzyl; $R_7$ is a radical selected from a group consisting of hydrogen, —OH, -and O-Benzyl, with a proviso that, if $R_2$ is —OH, then $R_3$ and $R_4$ can not both be hydrogen.

2. A sandramycin analog as described in claim 1 represented by the following structure:

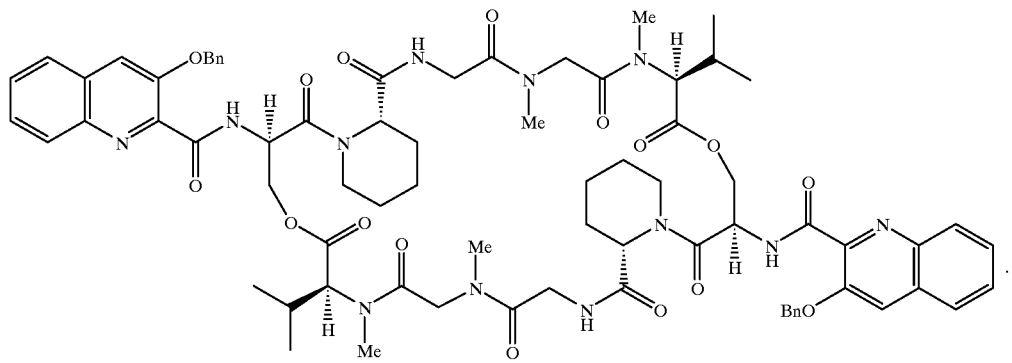
3. A sandramycin analog as described in claim 1 represented by the following structure:
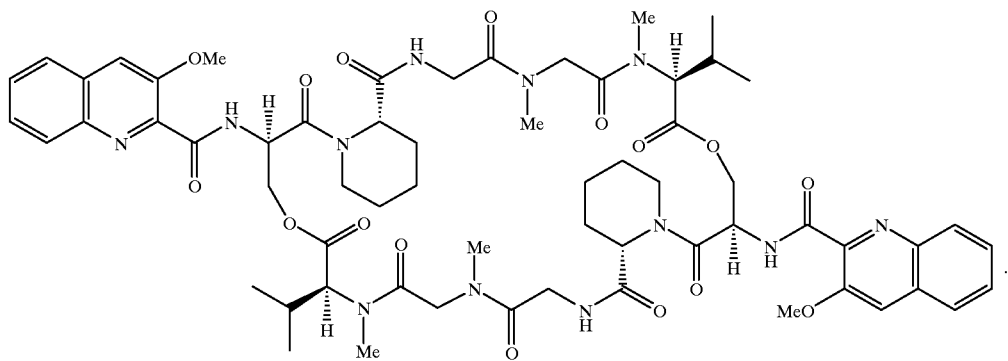
4. A sandramycin analog as described in claim 1 represented by the following structure:
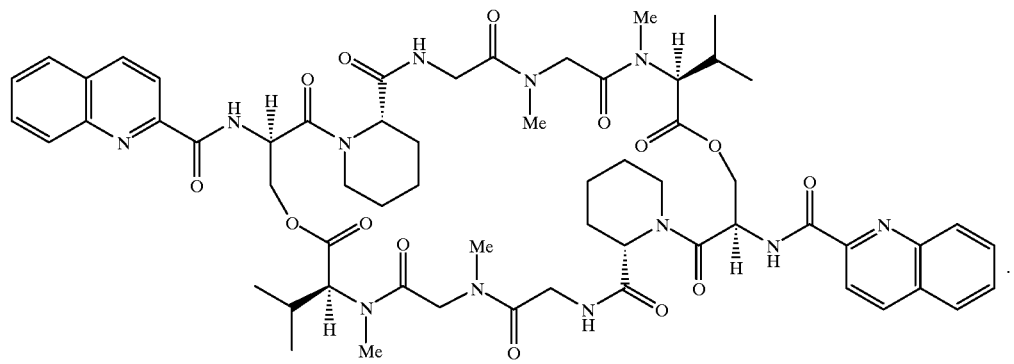
5. A sandramycin analog as described in claim 1 represented the following structure:

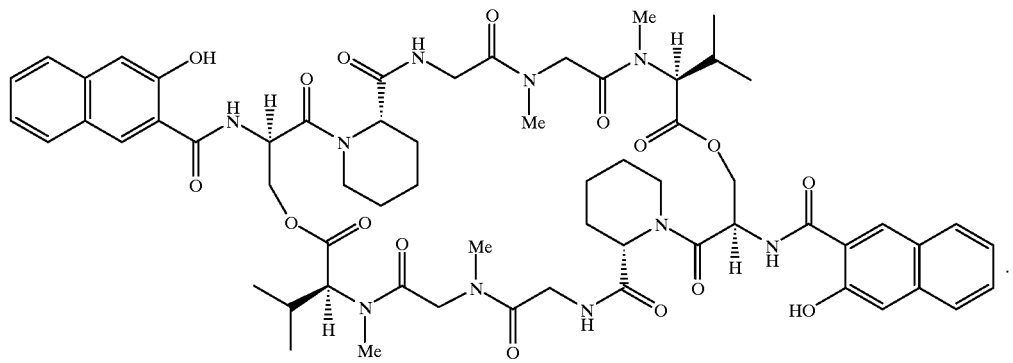
6. A sandramycin analog as described in claim 1 represented by the following structure:
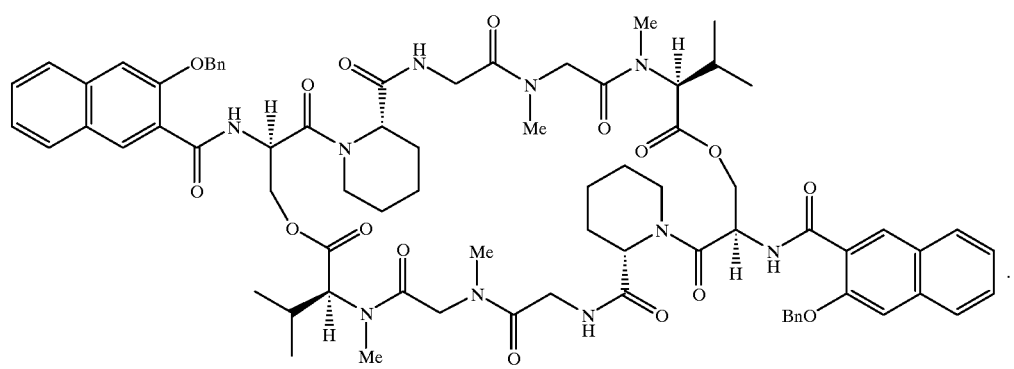
7. A sandramycin analog as described in claim 1 represented by the following structure:
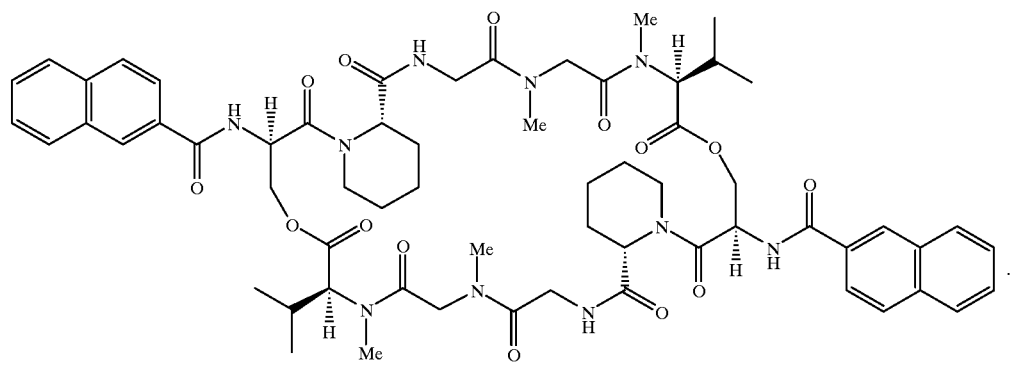
8. A sandramycin analog as described in claim 1 represented by the following structure:

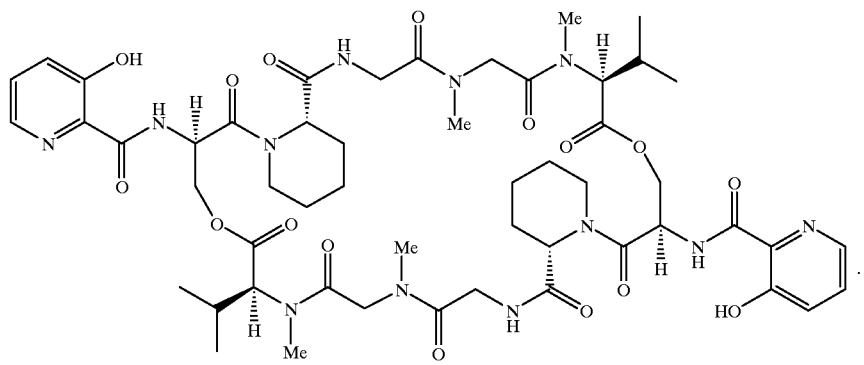
8
9. A sandramycin analog as described in claim 1 represented by the following structure:
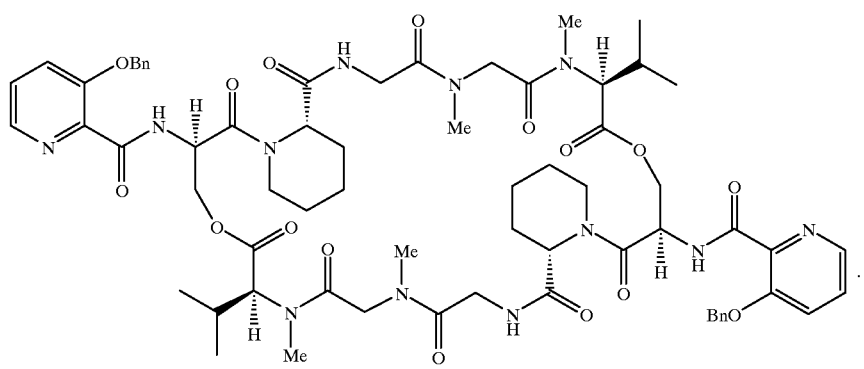
9
10. A sandramycin analog as described in claim 1 represented by the following structure:
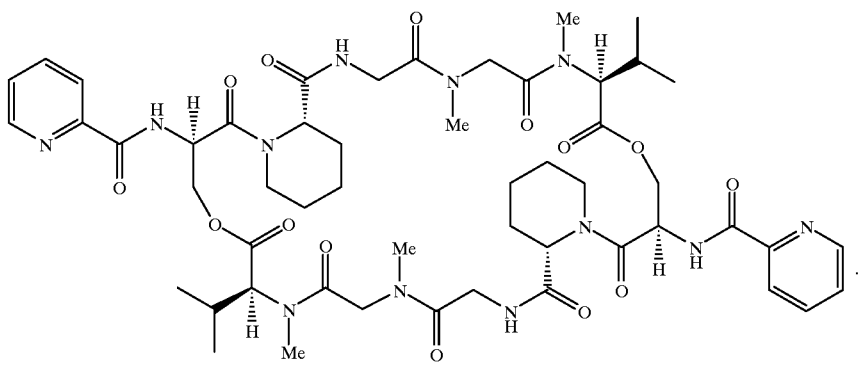
10
11. A sandramycin analog as described in claim 1 represented by the following structure:

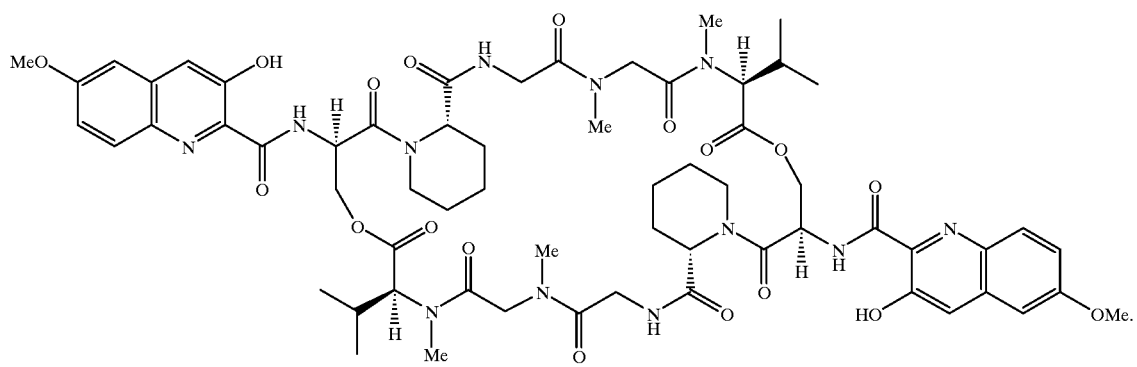
11
12. A sandramycin analog as described in claim 1 represented by the following structure:
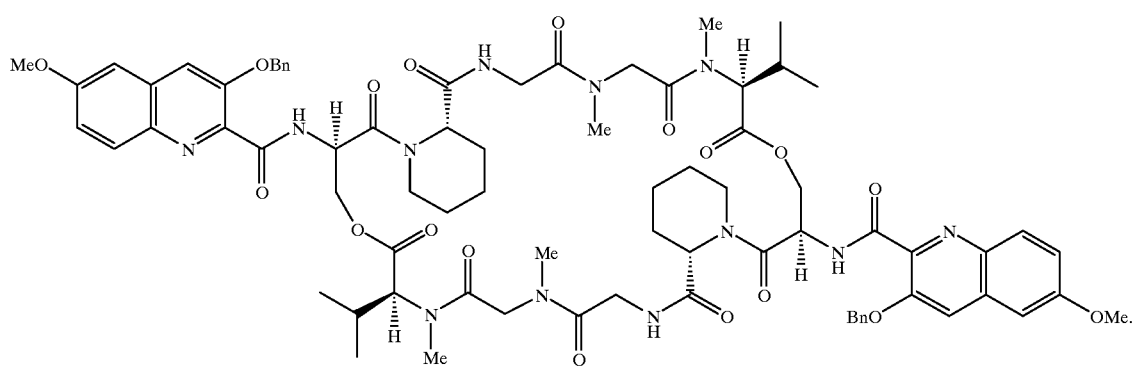
12
13. A sandramycin analog as described in claim 1 represented by the following structure:
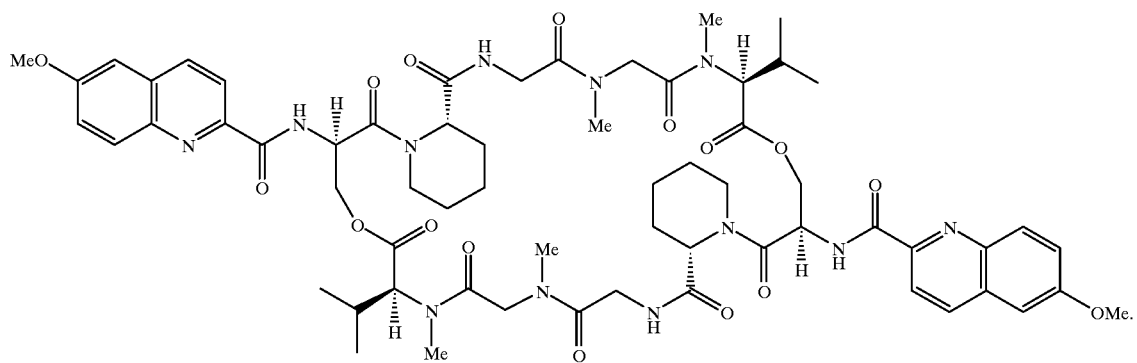
13
14. A sandramycin analog as described in claim 1 represented by the following structure:

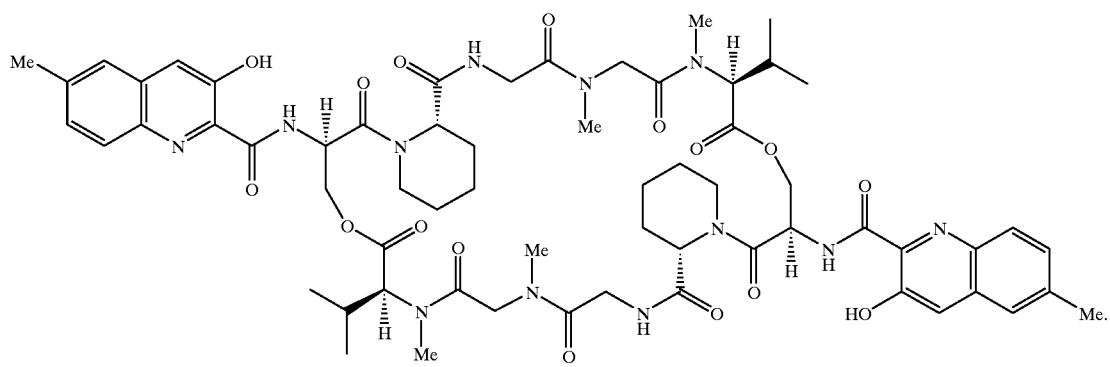
14
15. A sandramycin analog as described in claim 1 represented by the following structure:
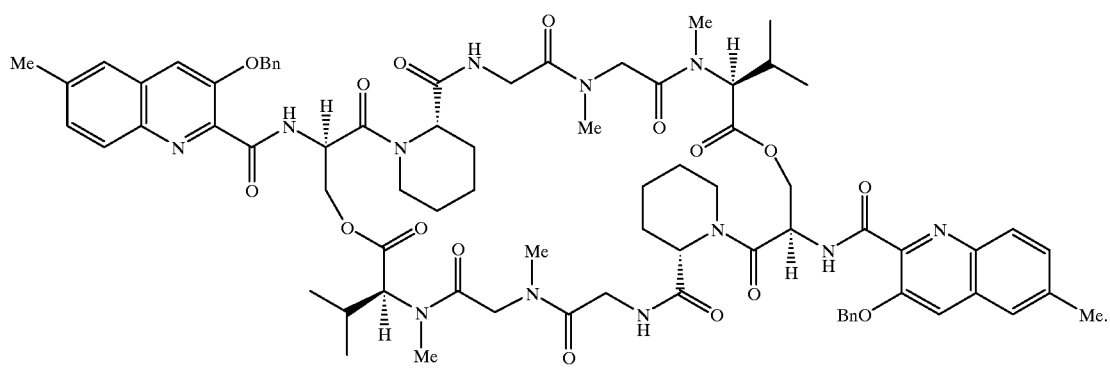
15
16. A sandramycin analog as described in claim 1 represented by the following structure:
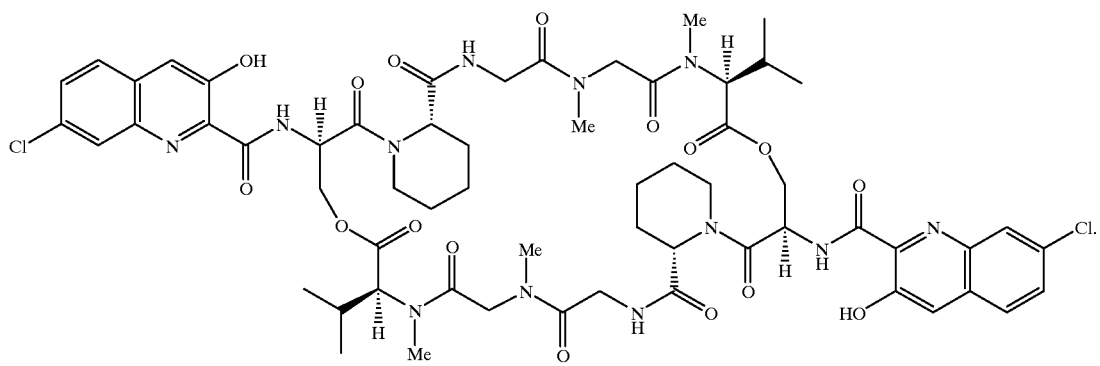
16
17. A sandramycin analog as described in claim 1 represented by the following structure:

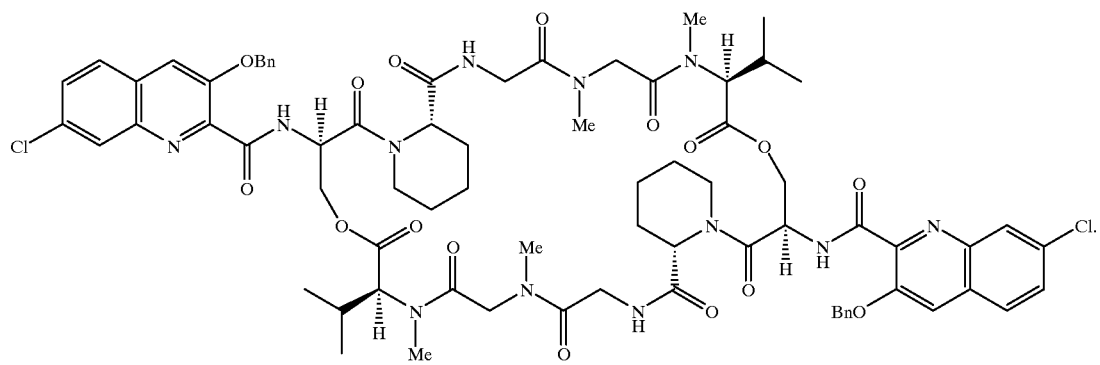
17
18. A sandramycin analog as described in claim 1 represented by the following structure:
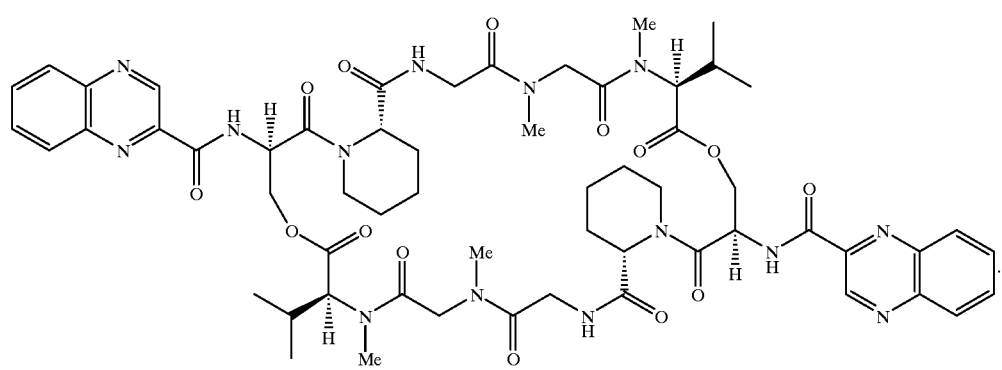
18
19. A sandramycin analog as described in claim 1 represented by the following structure:
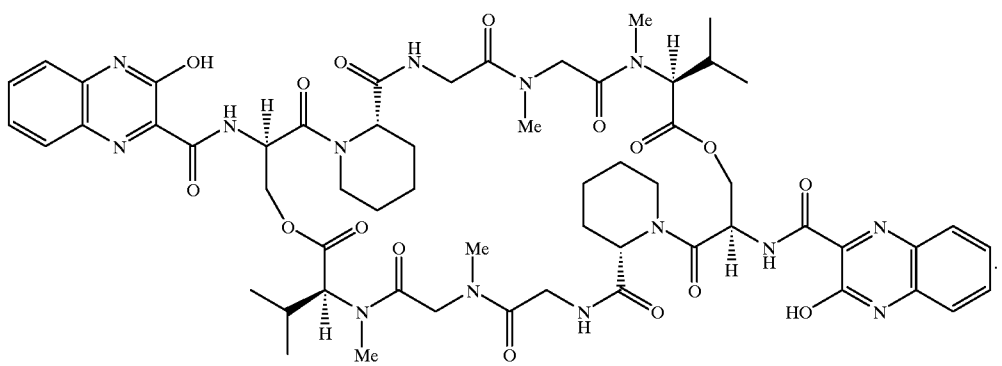
19
20. A sandramycin analog as described in claim 1 represented by the following structure:

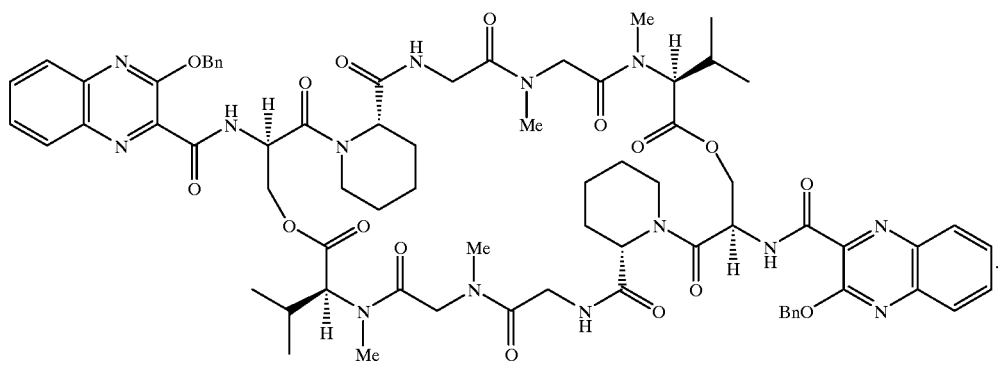

20

21. A sandramycin analog as described in claim 1 represented by the following structure:

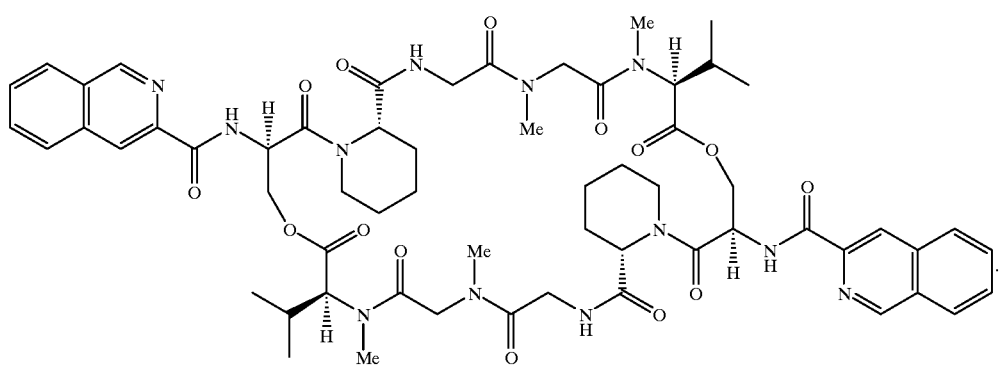

21

22. A sandramycin analog as described in claim 1 represented by the following structure:

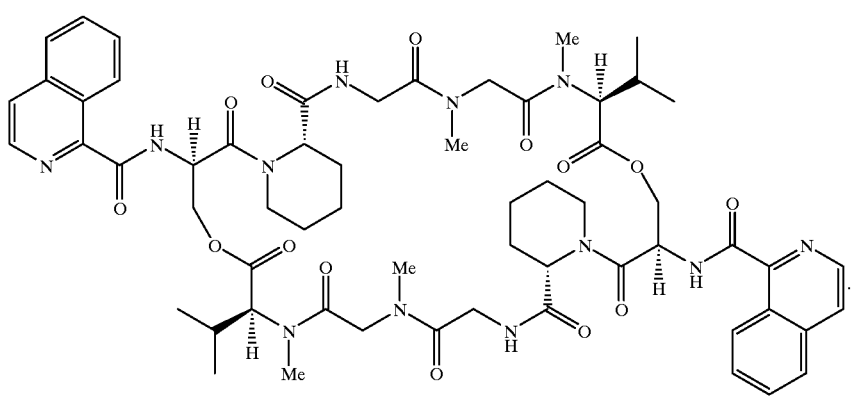

22

23. A topical formulation comprising a therapeutically effective concentration of sandramycin or of a sandramycin analog having cytotoxic activity, said sandramycin or sandramycin analog being admixed with a pharmaceutically acceptable carrier employable for topical administration, therein said sandramycin or sandramycin analog is represented by the following structure:

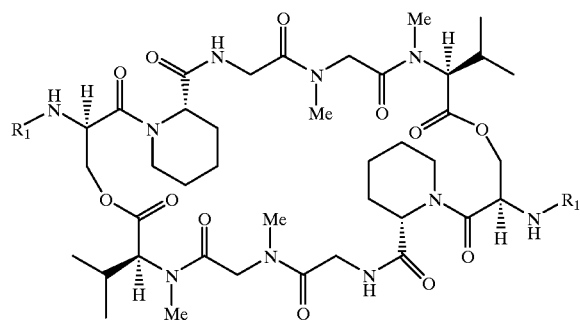

wherein $R_1$ is a radical selected from a group consisting of one of the following structures:

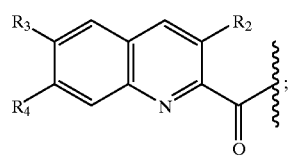 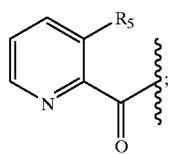

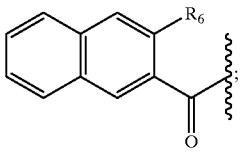 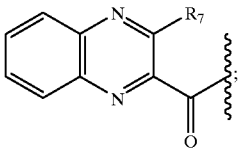

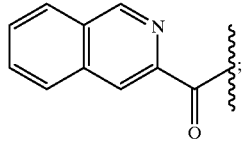 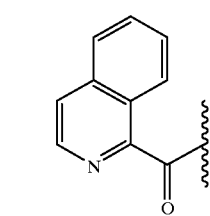

wherein $R_2$ is a radical selected from a group consisting of hydrogen, —OH, —OBenzyl, and —OMethyl; $R_3$ is a radical selected from a group consisting of hydrogen, —OMethyl, and Methyl; $R_4$ is a radical selected from a group consisting of hydrogen, and —Cl; $R_5$ is a radical selected from a group consisting of hydrogen, —OH, -and O-Benzyl; $R_6$ is a radical selected from a group consisting of hydrogen, —OH, -and O-Benzyl; $R_7$ is a radical selected from a group consisting of hydrogen, —OH, -and O-Benzyl.

24. A topical formulation described in claim 23 wherein the sandramycin analog is represented by the following structure:

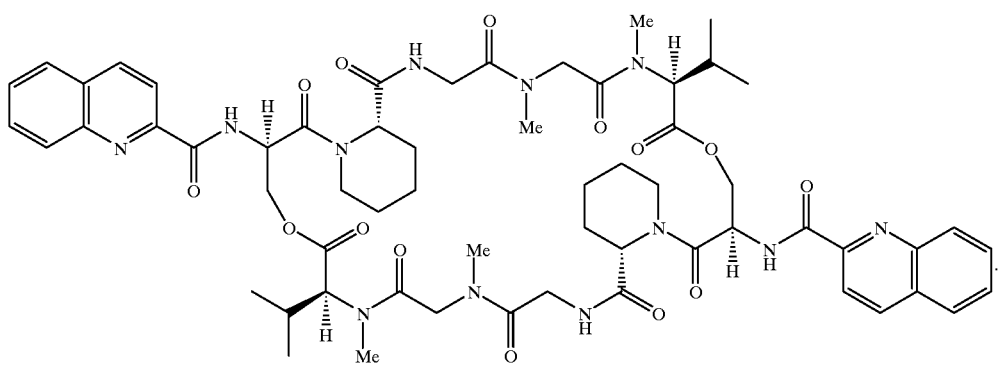

25. A topical formulation according to claim 23 wherein the topical formulation is employable for treating melanoma and the sandramycin analog is selected from the structures represented in claim 2 or 3 or 4 or 5 or 6 or 7 or 8 or 9 or 10 or 11 or 12 or 13 or 14 or 15 or 16 or 17 or 18 or 19 or 20 or 21 or 22.

26. The topical formulation according to claim 25 wherein the pharmaceutically acceptable carrier includes a hydrophobic ointment base.

27. The topical formulation according to claim 26 wherein the hydrophobic ointment base is selected from a group consisting of mineral oil and polyethylene; an emollient cream consisting of white petrolatum USP, purified water USP, isopropyl myristate NF, lanolin alcohols NF, mineral oil USP, cetostearyl alcohol NF, aluminum stearate and magnesium stearate; white petrolatum USP; and a liposome.

28. The topical formulation according to claim 23 wherein the pharmaceutically acceptable carrier includes a hydrophobic ointment base.

29. The topical formulation according to claim 23 wherein the hydrophobic ointment base is selected from a group consisting of mineral oil and polyethylene; an emollient cream consisting of white petrolatum USP, purified water USP, isopropyl myristate NF, lanolin alcohols NF, mineral oil USP, cetostearyl alcohol NF, aluminum stearate and magnesium stearate; white petrolatum USP; and a liposome.

30. A method for treating a subject having a melanoma, the method comprising the step of applying a topical formulation to the melanoma of said subject, wherein the topical formulation includes a therapeutically effective amount of sandramycin or of a sandramycin analog having cytotoxic activity with respect to the melanoma, said sandramycin or sandramycin analog being admixed with a pharmaceutically acceptable carrier for treating the melanoma, therein said sandramycin or sandramycin analog is represented by the following structure:

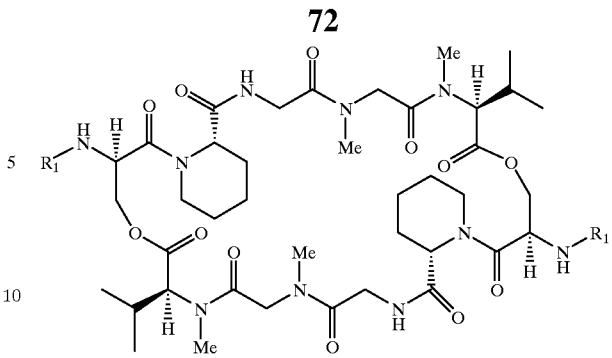

wherein $R_1$ is a radical selected from a group consisting of one of the following structures:

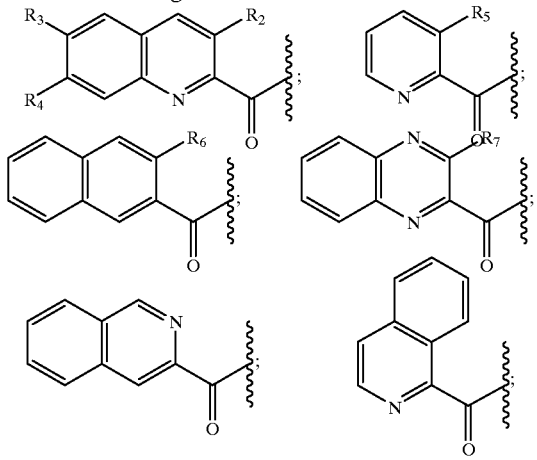

wherein $R_2$ is a radical selected from a group consisting of hydrogen, —OH, —OBenzyl, and —OMethyl; $R_3$ is a radical selected from a group consisting of hydrogen, —OMethyl, and Methyl; $R_4$ is a radical selected from a group consisting of hydrogen, and —Cl; $R_5$ is a radical selected from a group consisting of hydrogen, —OH, -and O-Benzyl; $R_6$ is a radical selected from a group consisting of hydrogen, —OH, -and O-Benzy; $R_7$ is a radical selected from a group consisting of hydrogen, —OH, -and O-Benzyl.

31. A method for treating melanoma as described in claim 30 wherein the sandramycin analog is represented by the following structure:

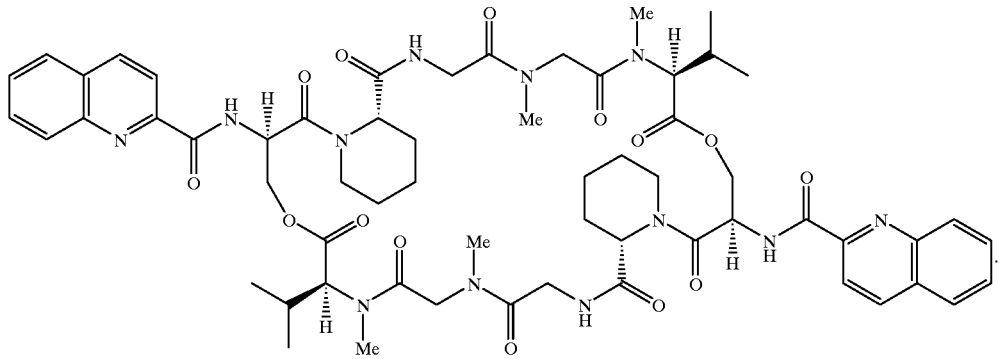

32. A method according to claim 30 wherein the pharmaceutically acceptable carrier includes a hydrophobic ointment base.

33. A method according to claim 32 wherein the hydrophobic ointment base is selected from a group consisting of mineral oil and polyethylene; an emollient cream consisting of white petrolatum USP, purified water USP, isopropyl myristate NF, lanolin alcohols NF, mineral oil USP, cetostearyl alcohol NF, aluminum stearate and magnesium, stearate; white petrolatum USP; and a liposome.

* * * * *

UNITED STATES PATENT AND TRADEMARK OFFICE
CERTIFICATE OF CORRECTION

PATENT NO. : 6,329,497 B1
DATED : December 11, 2001
INVENTOR(S) : Dale L. Boger

It is certified that error appears in the above-identified patent and that said Letters Patent is hereby corrected as shown below:

Column 1,
Line 8, insert -- This invention was made with government support under Contract No. CA 41101 by the National Institutes of Health. The government has certain rights in the invention. --

Signed and Sealed this

Seventh Day of May, 2002

Attest:

Attesting Officer

JAMES E. ROGAN
Director of the United States Patent and Trademark Office